(12) United States Patent
Steger et al.

(10) Patent No.: US 10,150,982 B2
(45) Date of Patent: Dec. 11, 2018

(54) MICROBIAL ECOLOGY SHIFT ASSAY

(71) Applicant: Second Genome, Inc., South San Francisco, CA (US)

(72) Inventors: Rachel Steger, Sunnyvale, CA (US); Peter DiStefano, Southborough, MA (US); Nadir Mahmood, San Francisco, CA (US)

(73) Assignee: Second Genome, Inc., South San Francisco, CA (US)

( * ) Notice: Subject to any disclaimer, the term of this patent is extended or adjusted under 35 U.S.C. 154(b) by 186 days.

(21) Appl. No.: 14/775,722

(22) PCT Filed: Mar. 10, 2014

(86) PCT No.: PCT/US2014/022844
§ 371 (c)(1),
(2) Date: Sep. 14, 2015

(87) PCT Pub. No.: WO2014/159287
PCT Pub. Date: Oct. 2, 2014

(65) Prior Publication Data
US 2016/0145670 A1    May 26, 2016

Related U.S. Application Data

(60) Provisional application No. 61/784,629, filed on Mar. 14, 2013.

(51) Int. Cl.
*C12Q 1/06* (2006.01)
*G01N 33/569* (2006.01)

(52) U.S. Cl.
CPC ............ *C12Q 1/06* (2013.01); *G01N 33/569* (2013.01); *G01N 2500/10* (2013.01)

(58) Field of Classification Search
None
See application file for complete search history.

(56) References Cited

U.S. PATENT DOCUMENTS

| | | |
|---|---|---|
| 6,090,573 A | 7/2000 | Laine et al. |
| 2002/0037516 A1 | 3/2002 | Murchie et al. |
| 2006/0275816 A1 | 12/2006 | Henderson et al. |
| 2009/0291858 A1 | 11/2009 | Andersen et al. |
| 2012/0045826 A1 | 2/2012 | Yantz et al. |
| 2012/0165215 A1 | 6/2012 | Andersen et al. |

FOREIGN PATENT DOCUMENTS

| | | |
|---|---|---|
| WO | WO99004043 A1 | 1/1999 |
| WO | WO2007039319 A2 | 4/2007 |
| WO | WO2009/102844 A2 | 8/2009 |
| WO | WO2014159287 A1 | 10/2014 |

OTHER PUBLICATIONS

Arboleya, S., et al., Assessment of intestinal microbiota modulation ability of Bifidobacterium strains in in vitro fecal patch cultures from preterm neonates, Anaerobe 19:9-16, 2013.

*Primary Examiner* — David W Berke-Schlessel
(74) *Attorney, Agent, or Firm* — Jill A. Jacobson; FisherBroyles, LLP

(57) ABSTRACT

The disclosure provides assay methods for characterizing the effects of an agent on a microbiome of a subject. Moreover, the disclosure provides methods for practical applications of assay results. The biological sample is extracted and the microbial population is enumerated by using signals or markers specific to the microbial species. The enumerated population is subjected to the action of one or many therapeutic agents and the efficiency is assessed by deriving a score based on the effects in the individual samples and in the population of samples.

21 Claims, 17 Drawing Sheets

- ■ k__Bacteria:p__Bacterioidetes:c__Bacteroidia:o__Bacteroidales:
  f:__Bacteroidaceae:g__Bacteroides:s__unclassified
- □ k__Bacteria:p__Firmicutes:c__Clostridia:o__Clostridiales:
  f:__Lachnospiraceae:g__unclassified:s__unclassified
- ▨ k__Bacteria:p__Firmicutes:c__Clostridia:o__Clostridiales:
  f:__Ruminococcaceae:g__unclassified:s__unclassified
- ▧ k__Bacteria:p__Firmicutes:c__Clostridia:o__Clostridiales:
  f:__Lachnospiraceae:g__Blautia:s__unclassified
- ▨ k__Bacteria:p__Firmicutes:c__Clostridia:o__Clostridiales:
  f:__Lachnospiraceae:g__Clostridium:s__unclassified
- ≡ k__Bacteria:p__Firmicutes:c__Clostridia:o__Clostridiales:
  f:__Ruminococcaceae:g__Faecalibacterium:s__unclassified
- ▦ k__Bacteria:p__Proteobacteria:c__Gammaproteobacteria:o__Enterobacteriales:
  f:__Enterobacteriaceae:g__Escherichia:s__unclassified
- ▨ k__Bacteria:p__Firmicutes:c__Clostridia:o__Clostridiales:
  f:__Lachnospiraceae:g__Roseburia:s__unclassified
- ▨ k__Bacteria:p__Firmicutes:c__Clostridia:o__Clostridiales:
  f:__Lachnospiraceae:g__Coprococcus:s__unclassified
- ≣ Other

*FIG. 8 (continued)*

MICROBIAL ECOLOGY SHIFT ASSAY

CROSS-REFERENCE

This application is a U.S. National Phase Application under 35 U.S.C. § 371 of PCT/US2014/022844, filed on Mar. 10, 2014, which claims the benefit of U.S. Provisional Patent Application No. 61/784,629, filed Mar. 14, 2013, said application is incorporated herein by reference in its entirety for all purposes.

BACKGROUND

Various microbiota found in a living organism provide many crucial contributions to its host, including, for example, aiding digestion, aiding in the development of immune systems, and/or imparting resistance to pathogenic colonization. Even a slight fluctuation in the symbiotic balance between microbiota and its host may be deleterious to the host, possibly leading to a pathological condition. For example, perturbations in the human gut may lead to conditions such as *Clostridium difficile* infection or inflammatory bowel disease (IBD). The composition of a microbial community can undergo changes as a result of interactions between the microbiota and a host's immune and metabolic systems, and/or interactions between the microbiota and exogenous agents. In one example, human exposure to antibiotics is known to have both short-term and long-term effects on the composition of various host microbiota, including those of the gut. The ability to monitor various degrees of change in the microbiome is of utility in diagnosing and treating disease.

SUMMARY

This disclosure provides in vitro assay methods for determining the effects of an agent on the microbiota of a given subject. Moreover, this disclosure provides methods for interpreting and/or utilizing the results of an assay described herein.

An aspect of the disclosure is a method for providing counseling to a subject comprising obtaining a sample from a first subject; contacting the sample with an agent in a reaction mixture; obtaining an enumeration of the abundance of one or more microbial taxa or taxon-identifying chemical species in the reaction mixture after contacting the sample with the agent; and providing counseling regarding the exposure of the agent to the first subject and/or one or more additional subjects using the enumeration or a manipulation of the enumeration.

The method may include the selection of the first subject and/or the additional subjects for use of the agent. In some cases, the first subject and/or the additional subjects have a condition. The condition may be selected from the group consisting of: *Clostridium difficile* infection, inflammatory bowel disease (IBD), a condition of the gut, Crohn's Disease (CD), irritable bowel syndrome (IBS), stomach ulcers, colitis, neonatal necrotizing enterocolitis, or gastroesophageal reflux disease (GERD), cystic fibrosis, chronic obstructive pulmonary disease, rhinitis, atopy, asthma, acne, a food allergy, obesity, periodontal disease, diarrhea, constipation, functional bloating, gastritis, lactose intolerance, visceral hyperalgesia, colic, pouchitis, diverticulitis, allergies, asthma, sinusitis, chronic obstructive pulmonary disorder (COPD), depression, attention deficit hyperactivity disorder (ADHD), autism, Alzheimers, migraines, multiple sclerosis (MS), Lupus, arthritis, Type 2 diabetes, obesity, non alcoholic steato hepatitis (NASH), non alcoholic fatty liver disease (NAFLD), risk of infarction/cardiovascular risk, heart failure, cancer, dental caries, gingivitis, oral cancer, oral mucositis, bacterial vaginosis, fertility, sinusitis, allergies, cystic fibrosis, lung cancer, psoriasis, atopic dermatis, methicillin-resistant *staphylococcus aureus* (MRSA), colorectal cancer, vancomycin resistant *enterococcus*, and combinations thereof. In some cases, the agent may be used to treat the condition in the first subject and/or the additional subjects.

Moreover, the agent may be a drug. In some cases, the drug is selected from the group consisting of: an approved drug, a drug available on the market, a withdrawn, a drug in pre-clinical development, a drug in clinical development, a drug under regulatory review, an unapproved drug, and combinations thereof. Additionally, the drug may be an antibiotic.

Counseling can include a variety of types of information. In some cases, counseling includes information selected from the group consisting of: the enumeration, information regarding the efficacy of the agent, information regarding the safety of the agent, information regarding the safety of the agent when administered with one or more different agents, information regarding the efficacy of the agent when administered with one or more different agents, a recommendation to use the agent, a recommendation to continue to use of the agent, a recommendation to not use the agent, a recommendation to discontinue use of the agent, providing a ranked list of possible agents or combination of agents for use or continued use, a recommendation for the addition of one or more different agents to a regimen comprising the agent, a recommendation for monitoring use of the agent over time, a recommendation for a dose of the agent, a recommendation regarding the propensity of an agent to cause a condition, and combinations thereof.

The first subject may be a pet or subject under the care or ownership of another subject.

Counseling may include the generation of a report.

In some cases, counseling may be provided by any of the following: a person, a company, a representative of a health-care organization, a health-care organization, a government official, a government office, a public health organization, a consultant, via a subscription service, via an online vendor, via a printed publication, via live audio, via an audio recording, via postal mail, via email, via telephone, via the internet, and combinations thereof.

It may be the case that first subject is of a different type of species than the additional subjects.

The first subject may be selected from the group consisting of a species of a mammal, a species of a rodent, a species of a mouse, a species of a rat, a species of a dog, a species of a cat, a species of a hamster, a species of a monkey, a species of a pig, a species of a squirrel, a species a guinea pig, a species of a gerbil, a species of a bird, a species of a hydra, a species of a rabbit, a species of a fish, a species of a frog, a species of a cow, a species of a lamb, a species of a chicken, a species of *Drosphilia*, a species of *Xenopus*, a species of horse, and a human.

The additional subjects may be selected from the group consisting of a species of a mammal, a species of a rodent, a species of a mouse, a species of a rat, a species of a dog, a species of a cat, a species of a hamster, a species of a monkey, a species of a pig, a species of a squirrel, a species a guinea pig, a species of a gerbil, a species of a bird, a species of a hydra, a species of a rabbit, a species of a fish, a species of a frog, a species of a cow, a species of a lamb, a species of a chicken, a species of *Drosphilia*, a species of *Xenopus*, a species of horse, and a human.

In some examples, the agent is a food, such, as a component of a diet.

In some examples, the agent is selected from the group consisting of a microbe, a virus, a fecal transplant, a drug, an antibiotic, a food, a beverage, a beauty care product, makeup, hairspray, lotion, a cosmetic, lip balm, sunscreen, a fragrance, a personal hygiene product, shampoo, soap, shower gel, conditioner, chemically treated wipes, hand sanitizer, an allergen, a household chemical, bleach, ammonia, a caustic, fertilizer, a gardening chemical, paint, paint thinner, a stain repellant, a water repellant, a wound dressing, a bandage, a liquid bandage, a wound antiseptic, hydrogen peroxide, an industrial chemical, a solvent, an acid, a hazardous chemical, water, an environmental sample, a soil sample, an aerosol that may be inhaled via the nose or throat, a topical pain reliever, an Epsom salt, a material used to make clothing, a polynucleotide, deoxyribonucleic acid (DNA), ribonucleic acid (RNA), RNA capable of RNA-interference (RNAi), a polypeptide, a protein, a recombinant protein, a lipid, cells conditioned to secrete a chemical substance, microbial metabolites, metabolites, detergents, surfactants, liposomes, drug delivery vehicles, and combinations thereof.

Additionally, the volume of the reaction mixture can vary. In some cases the volume of the reaction mixture may be at most 1 mL or at most 0.5 mL.

Counseling may include the use of a reference enumeration. The reference enumeration may be generated from samples obtained from a subject of a different species than the first subject.

Furthermore, the additional subjects may be a population. For example, the first subject may be a human and the population may be the human population.

In some cases, counseling may be completed with the aid of a computer.

Another aspect of the disclosure provides a method comprising: obtaining a sample from a first subject; contacting the sample with an agent in a reaction mixture, wherein the agent is selected from the group consisting of: a microbe, a virus, a fecal transplant, a drug, an antibiotic, a food, a beverage, a beauty care product, makeup, hairspray, lotion, a cosmetic, lip balm, sunscreen, a fragrance, a personal hygiene product, shampoo, soap, shower gel, conditioner, chemically treated wipes, hand sanitizer, an allergen, a household chemical, bleach, ammonia, a caustic, fertilizer, a gardening chemical, paint, paint thinner, a stain repellant, a water repellant, a wound dressing, a bandage, a liquid bandages, a wound antiseptic, hydrogen peroxide, an industrial chemical, a solvent, an acid, a hazardous chemical, water, an environmental sample, a soil sample, an aerosol that may be inhaled via the nose or throat, a topical pain reliever, an Epsom salt, a material used to make clothing, a polynucleotide, deoxyribonucleic acid (DNA), ribonucleic acid (RNA), RNA capable of RNA-interference (RNAi), a polypeptide, a protein, a recombinant protein, a lipid, cells conditioned to secrete a chemical substance, microbial metabolites, metabolites, detergents, surfactants, liposomes, drug delivery vehicles, and combinations thereof; and obtaining an enumeration of the abundance of one or more microbial taxa or taxon-identifying chemical species in the reaction mixture after contacting the sample with the agent. The enumeration or a numerical manipulation of the enumeration is used for the selection of the first subject and/or additional subjects for use of the agent. The first subject may be of a different type of species than the additional subjects.

The first subject may be selected from the group consisting of a species of a mammal, a species of a rodent, a species of a mouse, a species of a rat, a species of a dog, a species of a cat, a species of a hamster, a species of a monkey, a species of a pig, a species of a squirrel, a species a guinea pig, a species of a gerbil, a species of a bird, a species of a hydra, a species of a rabbit, a species of a fish, a species of a frog, a species of a cow, a species of a lamb, a species of a chicken, a species of *Drosphilia*, a species of *Xenopus*, a species of horse, and a human.

The additional subjects may be selected from the group consisting of a species of a mammal, a species of a rodent, a species of a mouse, a species of a rat, a species of a dog, a species of a cat, a species of a hamster, a species of a monkey, a species of a pig, a species of a squirrel, a species a guinea pig, a species of a gerbil, a species of a bird, a species of a hydra, a species of a rabbit, a species of a fish, a species of a frog, a species of a cow, a species of a lamb, a species of a chicken, a species of *Drosphilia*, a species of *Xenopus*, a species of horse, and a human.

The first subject and/or the additional subjects may have a condition, such as, for example any of the following: *Clostridium difficile* infection, inflammatory bowel disease (IBD), a condition of the gut, Crohn's Disease (CD), irritable bowel syndrome (IBS), stomach ulcers, colitis, neonatal necrotizing enterocolitis, or gastroesophageal reflux disease (GERD), cystic fibrosis, chronic obstructive pulmonary disease, rhinitis, atopy, asthma, acne, a food allergy, obesity, periodontal disease, diarrhea, constipation, functional bloating, gastritis, lactose intolerance, visceral hyperalgesia, colic, pouchitis, diverticulitis, allergies, asthma, sinusitis, chronic obstructive pulmonary disorder (COPD), depression, attention deficit hyperactivity disorder (ADHD), autism, Alzheimers, migraines, multiple sclerosis (MS), Lupus, arthritis, Type 2 diabetes, obesity, non alcoholic steato hepatitis (NASH), non alcoholic fatty liver disease (NAFLD), risk of infarction/cardiovascular risk, heart failure, cancer, dental caries, gingivitis, oral cancer, oral mucositis, bacterial vaginosis, fertility, sinusitis, allergies, cystic fibrosis, lung cancer, psoriasis, atopic dermatis, methicillin-resistant *staphylococcus aureus* (MRSA), colorectal cancer, vancomycin resistant *enterococcus*, and combinations thereof.

Moreover, the agent may be used to treat the condition in the first subject and/or the additional subjects. In some cases, the agent is a drug selected, for example, from the group consisting of an approved drug, a drug available on the market, a withdrawn, a drug in pre-clinical development, a drug in clinical development, a drug under regulatory review, an unapproved drug, and combinations thereof. The drug may be an antibiotic.

Furthermore, the method may be used to make a decision regarding the utility of the agent. The utility may include the efficacy and/or safety or the agent. The method may also include determining the propensity of the agent to cause a condition, such as, for example, any of the following: *Clostridium difficile* infection, inflammatory bowel disease (IBD), a condition of the gut, Crohn's Disease (CD), irritable bowel syndrome (IBS), stomach ulcers, colitis, neonatal necrotizing enterocolitis, or gastroesophageal reflux disease (GERD), cystic fibrosis, chronic obstructive pulmonary disease, rhinitis, atopy, asthma, acne, a food allergy, obesity, periodontal disease, diarrhea, constipation, functional bloating, gastritis, lactose intolerance, visceral hyperalgesia, colic, pouchitis, diverticulitis, allergies, asthma, sinusitis, chronic obstructive pulmonary disorder (COPD), depression, attention deficit hyperactivity disorder (ADHD), autism, Alzheimers, migraines, multiple sclerosis (MS), Lupus, arthritis, Type 2 diabetes, obesity, non alcoholic steato hepatitis (NASH), non alcoholic fatty liver disease (NAFLD), risk of infarction/cardiovascular risk, heart failure, cancer, dental caries, gingivitis, oral cancer, oral mucositis, bacterial vaginosis, fertility, sinusitis, allergies, cystic fibrosis, lung cancer, psoriasis, atopic dermatis, methicillin-resistant *staphylococcus aureus* (MRSA), colorectal cancer, vancomycin resistant *enterococcus*, and combinations thereof.

In other cases, the method may be used to make a decision regarding the utility of a drug or a food, including food that is a component of a diet.

The first subject may be a pet or subject under the care or ownership of another subject.

Moreover, the method may be used to generate a list of preferred agents.

Additionally, the method may include the use of a reference enumeration that may be, for example, generated from samples obtained from a subject of a different species than the first subject.

It may be the case that the additional subjects are a population. For example, the first subject may be a human and the population may be the human population.

A method may be completed with the aid of a computer and the internet.

A further aspect of the disclosure provides a method comprising: obtaining a sample from a first subject; contacting the sample with an agent in a reaction mixture; obtaining an enumeration of the abundance of at least 60 microbial taxa or taxon-identifying chemical species in the reaction mixture after contacting the sample with the agent. The enumeration or a numerical manipulation of the enumeration may be used for the selection of the first subject and/or additional subjects for use of the agent. In some cases, the first subject may be of a different type of species than the additional subjects.

The first subject may be selected from the group consisting of a species of a mammal, a species of a rodent, a species of a mouse, a species of a rat, a species of a dog, a species of a cat, a species of a hamster, a species of a monkey, a species of a pig, a species of a squirrel, a species a guinea pig, a species of a gerbil, a species of a bird, a species of a hydra, a species of a rabbit, a species of a fish, a species of a frog, a species of a cow, a species of a lamb, a species of a chicken, a species of *Drosphilia*, a species of *Xenopus*, a species of horse, and a human.

The additional subjects may be selected from the group consisting of a species of a mammal, a species of a rodent, a species of a mouse, a species of a rat, a species of a dog, a species of a cat, a species of a hamster, a species of a monkey, a species of a pig, a species of a squirrel, a species a guinea pig, a species of a gerbil, a species of a bird, a species of a hydra, a species of a rabbit, a species of a fish, a species of a frog, a species of a cow, a species of a lamb, a species of a chicken, a species of *Drosphilia*, a species of *Xenopus*, a species of horse, and a human.

In some cases, the first subject and/or the additional subjects have a condition. The condition may be, for example, *Clostridium difficile* infection, inflammatory bowel disease (IBD), a condition of the gut, Crohn's Disease (CD), irritable bowel syndrome (IBS), stomach ulcers, colitis, neonatal necrotizing enterocolitis, or gastroesophageal reflux disease (GERD), cystic fibrosis, chronic obstructive pulmonary disease, rhinitis, atopy, asthma, acne, a food allergy, obesity, periodontal disease, diarrhea, constipation, functional bloating, gastritis, lactose intolerance, visceral hyperalgesia, colic, pouchitis, diverticulitis, allergies, asthma, sinusitis, chronic obstructive pulmonary disorder (COPD), depression, attention deficit hyperactivity disorder (ADHD), autism, Alzheimers, migraines, multiple sclerosis (MS), Lupus, arthritis, Type 2 diabetes, obesity, non alcoholic steato hepatitis (NASH), non alcoholic fatty liver disease (NAFLD), risk of infarction/cardiovascular risk, heart failure, cancer, dental caries, gingivitis, oral cancer, oral mucositis, bacterial vaginosis, fertility, sinusitis, allergies, cystic fibrosis, lung cancer, psoriasis, atopic dermatis, methicillin-resistant *staphylococcus aureus* (MRSA), colorectal cancer, vancomycin resistant *enterococcus*, and combinations thereof.

In some cases, the agent may be used to treat the condition in the first subject and/or the additional subjects.

In some cases, the agent is a drug, selected, for example, from the group consisting of: an approved drug, a drug available on the market, a withdrawn, a drug in pre-clinical development, a drug in clinical development, a drug under regulatory review, an unapproved drug, and combinations thereof. It may be that the drug is an antibiotic.

The method may be used to make a decision regarding the utility of the agent, wherein the utility may include the efficacy and/or safety or the agent.

The method may also include determining the propensity of the agent to cause a condition, such as, for example, any of the following: *Clostridium difficile* infection, inflammatory bowel disease (IBD), a condition of the gut, Crohn's Disease (CD), irritable bowel syndrome (IBS), stomach ulcers, colitis, neonatal necrotizing enterocolitis, or gastroesophageal reflux disease (GERD), cystic fibrosis, chronic obstructive pulmonary disease, rhinitis, atopy, asthma, acne, a food allergy, obesity, periodontal disease, diarrhea, constipation, functional bloating, gastritis, lactose intolerance, visceral hyperalgesia, colic, pouchitis, diverticulitis, allergies, asthma, sinusitis, chronic obstructive pulmonary disorder (COPD), depression, attention deficit hyperactivity disorder (ADHD), autism, Alzheimers, migraines, multiple sclerosis (MS), Lupus, arthritis, Type 2 diabetes, obesity, non alcoholic steato hepatitis (NASH), non alcoholic fatty liver disease (NAFLD), risk of infarction/cardiovascular risk, heart failure, cancer, dental caries, gingivitis, oral cancer, oral mucositis, bacterial vaginosis, fertility, sinusitis, allergies, cystic fibrosis, lung cancer, psoriasis, atopic dermatis, methicillin-resistant *staphylococcus aureus* (MRSA), colorectal cancer, vancomycin resistant *enterococcus*, and combinations thereof.

Additionally, the method may be used to make a decision regarding the utility of a drug or food, including a food that is a component of a diet.

Moreover, the first subject may be a pet or subject under the care or ownership of another subject.

In some cases, the method is used to generate a list of preferred agents and/or may include the use of a reference enumeration. The reference enumeration may be generated from samples obtained from a subject of a different species than the first subject.

In one example, the additional subjects are a population. In another example, the first subject is a human and the population is the human population.

A method may be completed with the aid of a computer and/or the internet.

It may be that at least 10000, 1000, 100, or 10 microbial taxa or taxon-identifying chemical species are enumerated.

Another aspect of the disclosure is a method comprising: obtaining a sample from a first subject; contacting the sample with an agent in a reaction mixture; obtaining an enumeration of the abundance of one or more microbial taxa or taxon-identifying chemical species in the reaction mixture after contacting the sample with the agent, wherein the volume of the reaction mixture is at most 1 milliliter (mL). In some cases, the enumeration or a numerical manipulation of the enumeration is used for the selection of the first subject and/or additional subjects for use of the agent. The first subject may be of a different type of species than the additional subjects.

The first subject may be selected from the group consisting of a species of a mammal, a species of a rodent, a species of a mouse, a species of a rat, a species of a dog, a species of a cat, a species of a hamster, a species of a monkey, a species of a pig, a species of a squirrel, a species a guinea pig, a species of a gerbil, a species of a bird, a species of a hydra, a species of a rabbit, a species of a fish, a species of a frog, a species of a cow, a species of a lamb, a species of a chicken, a species of *Drosphilia*, a species of *Xenopus*, a species of horse, and a human.

The additional subjects is selected from the group consisting of a species of a mammal, a species of a rodent, a species of a mouse, a species of a rat, a species of a dog, a species of a cat, a species of a hamster, a species of a monkey, a species of a pig, a species of a squirrel, a species a guinea pig, a species of a gerbil, a species of a bird, a species of a hydra, a species of a rabbit, a species of a fish, a species of a frog, a species of a cow, a species of a lamb, a species of a chicken, a species of *Drosphilia*, a species of *Xenopus*, a species of horse, and a human.

Moreover, the first subject and/or the additional subjects may have a condition, such as, for example, *Clostridium difficile* infection, inflammatory bowel disease (IBD), a condition of the gut, Crohn's Disease (CD), irritable bowel syndrome (IBS), stomach ulcers, colitis, neonatal necrotizing enterocolitis, or gastroesophageal reflux disease (GERD), cystic fibrosis, chronic obstructive pulmonary disease, rhinitis, atopy, asthma, acne, a food allergy, obesity, periodontal disease, diarrhea, constipation, functional bloating, gastritis, lactose intolerance, visceral hyperalgesia, colic, pouchitis, diverticulitis, allergies, asthma, sinusitis, chronic obstructive pulmonary disorder (COPD), depression, attention deficit hyperactivity disorder (ADHD), autism, Alzheimers, migraines, multiple sclerosis (MS), Lupus, arthritis, Type 2 diabetes, obesity, non alcoholic steato hepatitis (NASH), non alcoholic fatty liver disease (NAFLD), risk of infarction/cardiovascular risk, heart failure, cancer, dental caries, gingivitis, oral cancer, oral mucositis, bacterial vaginosis, fertility, sinusitis, allergies, cystic fibrosis, lung cancer, psoriasis, atopic dermatis, methicillin-resistant *staphylococcus aureus* (MRSA), colorectal cancer, vancomycin resistant *enterococcus*, and combinations thereof.

In some cases, the agent may be used to treat the condition in the first subject and/or the additional subjects. For example, the agent may be drug that is, for example, selected from the group consisting of: an approved drug, a drug available on the market, a withdrawn, a drug in pre-clinical development, a drug in clinical development, a drug under regulatory review, an unapproved drug, and combinations thereof. It may be that the drug is an antibiotic.

The method may be used to make a decision regarding the utility of the agent, including the efficacy and/or safety or the agent. Also, the method may include determining the propensity of the agent to cause a condition, such, as for example, any of the following: *Clostridium difficile* infection, inflammatory bowel disease (IBD), a condition of the gut, Crohn's Disease (CD), irritable bowel syndrome (IBS), stomach ulcers, colitis, neonatal necrotizing enterocolitis, or gastroesophageal reflux disease (GERD), cystic fibrosis, chronic obstructive pulmonary disease, rhinitis, atopy, asthma, acne, a food allergy, obesity, periodontal disease, diarrhea, constipation, functional bloating, gastritis, lactose intolerance, visceral hyperalgesia, colic, pouchitis, diverticulitis, allergies, asthma, sinusitis, chronic obstructive pulmonary disorder (COPD), depression, attention deficit hyperactivity disorder (ADHD), autism, Alzheimers, migraines, multiple sclerosis (MS), Lupus, arthritis, Type 2 diabetes, obesity, non alcoholic steato hepatitis (NASH), non alcoholic fatty liver disease (NAFLD), risk of infarction/cardiovascular risk, heart failure, cancer, dental caries, gingivitis, oral cancer, oral mucositis, bacterial vaginosis, fertility, sinusitis, allergies, cystic fibrosis, lung cancer, psoriasis, atopic dermatis, methicillin-resistant *staphylococcus aureus* (MRSA), colorectal cancer, vancomycin resistant *enterococcus*, and combinations thereof.

The method may be used to make a decision regarding the utility of a drug or food, including a food that is a component of a diet.

The first subject may be a pet or subject under the care or ownership of another subject.

Moreover, the method may be used to generate a list of preferred agents and/or may include the use of a reference enumeration. The reference enumeration may be generated from samples obtained from a subject of a different species than the first subject.

In some cases, the additional subjects are a population. In one instance, the first subject is a human and the population is the human population.

The method may be completed with the aid of a computer and the internet. In some cases, the volume of the reaction mixture is at most 1 mL, at most 0.75 mL, or at most 0.5 mL.

Another aspect of the disclosure provides a method comprising: obtaining a set of agents comprising at least 10 chemically distinct agents; obtaining a sample from a first subject; contacting an aliquot of the sample with each of the at least ten agents in an individual reaction mixture; obtaining an enumeration of the abundance of one or more microbial taxa or taxon-identifying chemical species in each the individual reaction mixture after the separately contacting an aliquot of the sample with each of the at least ten agents; and making a decision regarding the utility of each of the at least ten agents to be used as a drug based upon the enumerating.

The set may comprise at least 100, at least 1000, at least 10000, or at least 50000 chemically distinct agents.

The decision may include deciding to initiate or continue development of the agents of the set into drugs, deciding to begin a clinical-trial using one or more of the agents of the set, determining the safety of the agents of the set to be used as drugs, determining the efficacy of the agents of the set to be used as drugs to treat a condition. The condition, for example, may be *Clostridium difficile* infection, inflammatory bowel disease (IBD), a condition of the gut, Crohn's Disease (CD), irritable bowel syndrome (IBS), stomach ulcers, colitis, neonatal necrotizing enterocolitis, or gastroesophageal reflux disease (GERD), cystic fibrosis, chronic obstructive pulmonary disease, rhinitis, atopy, asthma, acne, a food allergy, obesity, periodontal disease, diarrhea, constipation, functional bloating, gastritis, lactose intolerance, visceral hyperalgesia, colic, pouchitis, diverticulitis, allergies, asthma, sinusitis, chronic obstructive pulmonary disorder (COPD), depression, attention deficit hyperactivity disorder (ADHD), autism, Alzheimers, migraines, multiple sclerosis (MS), Lupus, arthritis, Type 2 diabetes, obesity, non alcoholic steato hepatitis (NASH), non alcoholic fatty liver disease (NAFLD), risk of infarction/cardiovascular risk, heart failure, cancer, dental caries, gingivitis, oral cancer, oral mucositis, bacterial vaginosis, fertility, sinusitis, allergies, cystic fibrosis, lung cancer, psoriasis, atopic dermatis, methicillin-resistant *staphylococcus aureus* (MRSA), colorectal cancer, vancomycin resistant *enterococcus*, and combinations thereof.

The decision may be made, for example, by a drug-research organization or regulatory agency.

Another aspect of the disclosure provides a method comprising: obtaining a first sample from a first subject; contacting the first sample with an agent in a first reaction mixture; obtaining a first enumeration of the abundance of one or more microbial taxa or taxon-identifying chemical species in the first reaction mixture after the contacting the first sample with the one or more agents, wherein the volume of the first reaction mixture is less than about 1 mL; obtaining a second sample from a second subject; contacting the second sample with the agent to form a second reaction mixture; obtaining a second enumeration of the abundance of the microbial taxa or taxon-identifying chemical species in the second reaction mixture after the contacting the second sample with the one or more agents, wherein the volume of the second reaction mixture is less than about 1 mL; and comparing the second enumeration of the microbial taxa or taxon-identifying chemical species in the second reaction mixture with the first enumeration of the microbial taxa or taxon-identifying chemical species in the first reaction mixture.

Another aspect of the disclosure provides a method comprising: obtaining a first fecal sample from a first subject, wherein the first subject has a condition; contacting the first fecal sample with an agent in a first reaction mixture; obtaining a first enumeration of the abundance of one or more microbial taxa or taxon-identifying chemical species in the first reaction mixture after the contacting the first fecal sample with the one or more agents, wherein the volume of the first reaction mixture is less than about 1 mL; obtaining a second sample from a second subject; contacting the second sample with the agent to form a second reaction mixture; obtaining a second enumeration of the abundance of the microbial taxa or taxon-identifying chemical species in the second reaction mixture after the contacting the second sample with the one or more agents, wherein the volume of the second reaction mixture is less than about 1 mL; and comparing the second enumeration of the microbial taxa or taxon-identifying chemical species in the second reaction mixture with the first enumeration of the microbial taxa or taxon-identifying chemical species in the first reaction mixture; and making a decision regarding the suitability of the agent to be used as a therapeutic drug based upon the comparing.

The condition may be, for example, any of the following: *Clostridium difficile* infection, inflammatory bowel disease (IBD), a condition of the gut, Crohn's Disease (CD), irritable bowel syndrome (IBS), stomach ulcers, colitis, neonatal necrotizing enterocolitis, or gastroesophageal reflux disease (GERD), cystic fibrosis, chronic obstructive pulmonary disease, rhinitis, atopy, asthma, acne, a food allergy, obesity, periodontal disease, diarrhea, constipation, functional bloating, gastritis, lactose intolerance, visceral hyperalgesia, colic, pouchitis, diverticulitis, allergies, asthma, sinusitis, chronic obstructive pulmonary disorder (COPD), depression, attention deficit hyperactivity disorder (ADHD), autism, Alzheimers, migraines, multiple sclerosis (MS), Lupus, arthritis, Type 2 diabetes, obesity, non alcoholic steato hepatitis (NASH), non alcoholic fatty liver disease (NAFLD), risk of infarction/cardiovascular risk, heart failure, cancer, dental caries, gingivitis, oral cancer, oral mucositis, bacterial vaginosis, fertility, sinusitis, allergies, cystic fibrosis, lung cancer, psoriasis, atopic dermatis, methicillin-resistant *staphylococcus aureus* (MRSA), colorectal cancer, vancomycin resistant *enterococcus*, and combinations thereof.

A sample used in a method described herein may be, for example, earwax, sweat, breast milk, hair, blood, bile, cerebrospinal fluid, lymphatic fluid, semen, vaginal discharge, menstrual fluid, feces, sputum, urine, saliva, secretions from open wounds, secretions from the eye, skin tissue (e.g., a skin biopsy), subcutaneous tissue, muscle tissue, adipose tissue, and a combination thereof.

Furthermore, a sample may be obtained from, for example, the gut, the vagina, the penis, a testicle, the cervix, the respiratory system, the ear, the skin, the rectum, the kidney, the liver, the spleen, the lung, the pancreas, the small intestine, the gallbladder, the lymph nodes, the colon, a nasal passage, the central nervous system, an oral cavity, a sinus, a nare, the urogenital tract, an udder, an auditory canal, a breast, an open wound, the eye, fat, muscle, and combinations thereof.

In some instances, microbial taxa evaluated in a method may be operational taxonomic units (OTUs). OTUs may be formed by clustering nucleic acid sequences of microbial organisms based on gene sequence homology. In some cases, the gene is a 16S ribosomal ribonucleic acid (rRNA). OTUs may be characterized by microbes having at least 80% 16S RNA sequence homology.

In other instances, microbial taxa evaluated in a method may be domains, kingdoms, phyla, classes, orders, families, genera, and single species. Microbial taxa may or may not be derived from parsimonious phylogenetic trees.

Additionally, an enumeration of the abundance of one or more microbial taxa or taxon-identifying chemical species in a method may be completed by detecting, for example, a nucleic acid, a lipid, a carbohydrate, a protein, a peptide, a small molecule, and combinations thereof. The nucleic acid may be, for example, deoxyribonucleic acid (DNA), ribonucleic acid (RNA), or a combination of RNA and DNA. In some examples, the nucleic acid is all or a portion of a 16S ribosomal RNA (rRNA) gene or the 16S rRNA product of the gene.

The detecting may be completed using nucleic acid sequencing methods such as, for example, shotgun sequencing, polymerase chain reaction, real-time polymerase chain reaction, ligase chain reaction, single-molecule real-time sequencing, ion torrent sequencing, pyrosequencing, sequencing by synthesis, sequencing by ligation, chain termination sequencing, massively parallel signature sequencing, polony sequencing, SOLiD sequencing, DNA nanoball sequencing, heliscope single molecule sequencing, single molecule real time sequencing, nanopore sequencing, mass spectrometry sequencing, microfluidic sequencing, high-throughput sequencing, Illumina sequencing, HiSeq sequencing, MiSeq sequencing, and combinations thereof.

In some examples, detecting is completed by using one or more sequence-specific oligonucleotide probes that may be arranged, for example, in a nucleic acid array or arranged on microbeads.

In some examples, detecting may be completed using nucleic acid barcoding.

Moreover, it may be that a nucleic acid is the V1, V2, V3, V4, V5, V6, V7, V8, and/or V9 region of a 16S rRNA gene.

In some cases, the enumeration of the abundance of at least one microbial taxa or taxon-identifying chemical species in a method is completed by analyzing a proteome, a transcriptome, a metabolome, a metagenome, and combinations thereof.

Furthermore, a method may include a sample that is processed into a slurry.

A reaction mixture of a method may be incubated at a temperature of about 34° C. to about 42° C. In some cases, the reaction mixture is incubated at a temperature of about 37° C.

A reaction mixture may be incubated from about 1 day to about 5 days. In some examples, the reaction mixture is incubated for about 1 day.

A reaction mixture may be incubated in an anaerobic incubation atmosphere.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION

Figure 1:
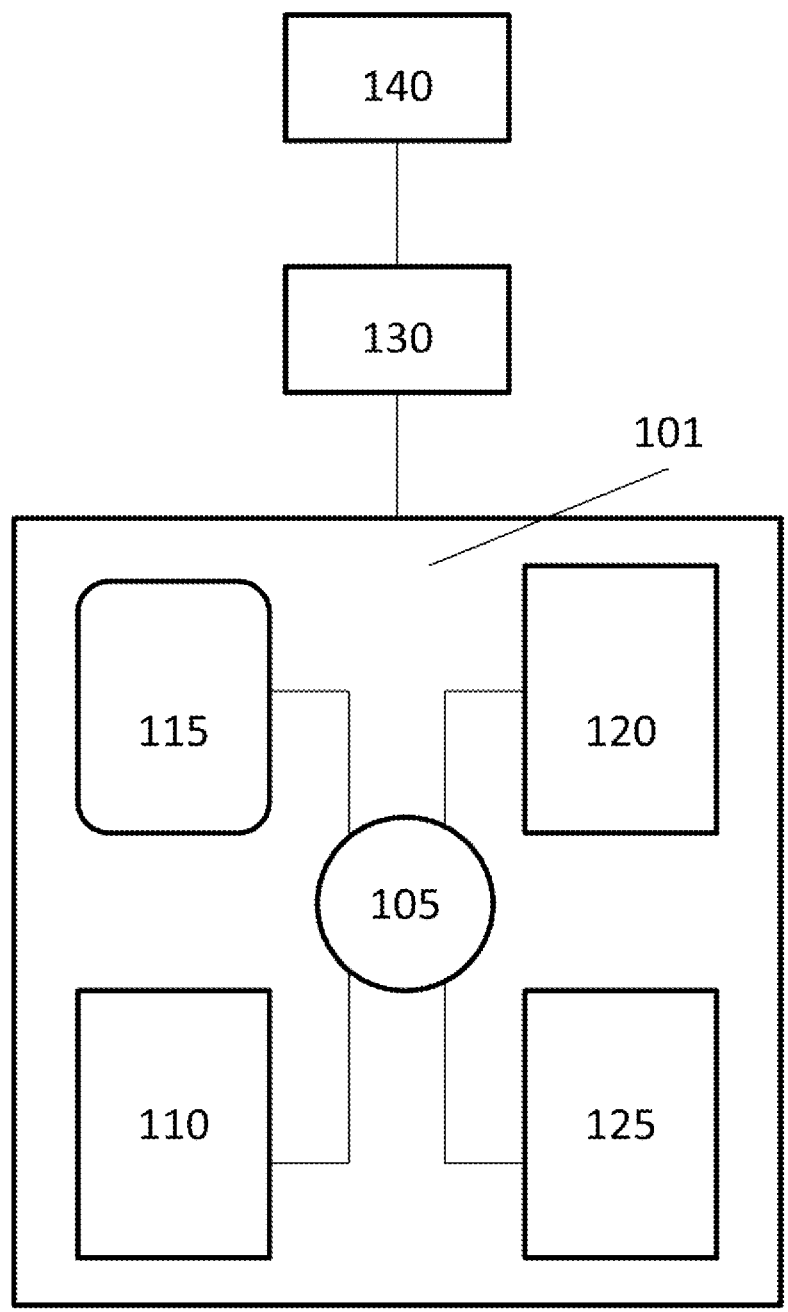
FIG. 1 is a schematic depicting an example system for executing methods of the disclosure.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

As used herein, the singular forms "a," "an," and "the" are intended to include the plural forms as well, unless the context clearly indicates otherwise. Furthermore, to the extent that the terms "including", "includes", "having", "has", "with", "such as", or variants thereof, are used in either the specification and/or the claims, such terms are not limiting and are intended to be inclusive in a manner similar to the term "comprising".

The term "about," as used herein, generally refers to a range that is 15% greater than or less than a stated numerical value within the context of the particular usage. For example, "about 10" would include a range from 8.5 to 11.5.

The term "agent," as used herein, generally refers to any material evaluated for its effect on a microbiome.

The term "condition," as used herein, generally refers to any abnormal physical and/or mental state of a living organism.

The term "microbiome," as used herein, generally refers to the totality, or a subset of the totality, of microbes, their genetic elements (genomes), and interactions with a particular environment. Such an environment, for example, may be a region of a living organism.

The term "microbiota," as used herein, generally refers to the microflora and/or microfauna in an ecosystem. Such an ecosystem, for example, may be in a host living organism, or a particular region within a host living organism.

The term "taxon-identifying chemical species," as used herein, generally refers to any chemical species whose detection may be used to identify an associated microbial taxa. In some cases, the detection of a taxon-identifying chemical species may indicate the abundance of an associated microbial taxon in a microbial community. In other cases, or in parallel, a taxon-identifying chemical species may indicate the functionality of an associated microbial taxon within a microbial community. Non-limiting examples of a taxon-identifying chemical species include a product of microbe gene expression, a product of microbe metabolism (e.g., a metabolite), a chemical component of a microbe's structure, a chemical species secreted by a microbe, and a product of microbe respiration.

The term "sample," as used herein, generally refers to a specimen, or a portion of a specimen, obtained from a subject.

The terms "taxa," or "taxon," as used herein, generally refers to a group of microbes adjudged to be a unit. Microbes may be classified into taxa by a host of different types of characteristics. Several example classification schemes are described below.

The microbiota of a living organism may be altered when exposed to exogenous agents without consideration to how such agents may affect the microbiota. The impact of an agent on the composition and/or functionality of a subject's microbiota may not be thoroughly considered during the development of an agent, including the case of a therapeutic drug, such as an antibiotic. Indeed, complications with the consumption of or exposure to a particular agent may be due to unfavorable disruption of microbiota.

Additionally, an agent may be useful for treating a condition related to an abnormal state of the microbiota of a living organism. An agent may be used as a therapeutic, for example, to shift the composition and/or function of the microbiota of a condition-afflicted subject toward the composition and/or function of a normal (i.e., healthy) subject. Indeed, both in vivo and in vitro assays may be useful in assessing the suitability of an agent for use as a therapeutic.

Shortcomings to assessing the impact of an agent on microbiota may be due to the lack of available, reproducible, and standardized methods for assessing the differential impact of an agent on the composition and functionality of various microbial communities within a living organism. In one aspect, the successful development of such methods requires that various challenges be overcome including the fact that many microbial communities are often characterized by intrinsic variations, including across host species, subjects of a species, and across time. In another aspect, safety regulations regarding agent use in subjects may make it difficult to assess the differential impact of unapproved and/or potentially harmful agents. As a result, reliance upon in vitro or ex vivo assays may be desirable and/or necessary. Nevertheless, the successful development of reliable methods that enable accurate, reproducible assessment of the potential of an agent to alter microbial communities of a living organism could offer an important tool for assessing the impact and/or therapeutic utility of an agent.

Recognized herein is a need for methods for reproducible assessment of the differential impact of an agent on the composition and functionality of microbial communities in a host living organism. "Composition" as used herein may generally refer to the makeup of a microbial community and may include either or both of the number of microbes and types of microbes of the particular microbial community. "Functionality" as used herein may generally refer to the capability of a microbial community to exercise its regular homeostatic activities with non-limiting examples that include metabolism, respiration, and gene expression.

This disclosure provides methods and systems for characterizing the effects of one or more agents on at least one microbial organism of a subject host. In one aspect, the disclosure provides methods for in vitro assays that may be used to characterize the effects of an agent on the microbiota of a given subject. Methods generally rely on the enumeration of microbial taxa found in samples obtained from subjects, when the samples are contacted with one or more agents of interest.

Enumerations may be made directly such that microbial taxa are enumerated or may be made indirectly such that an enumeration of a taxon-identifying chemical species associated with a taxon of interest is completed. In some cases, both types of enumerations are made. Enumerating taxon-identifying chemical species may be useful in assessing changes to either or both of abundance and functionality with respect to a microbial taxon. Enumerations may be completed at one or more time points prior to, during, and/or after contacting samples with the agent of interest.

In another aspect, this disclosure provides methods for estimating the effects of an agent on the microbiota of a first subject, using samples taken from a second subject. The first subject may be of the same species as the second subject or may be of a different species. More specifically, such methods generally include contacting a sample obtained from the second subject with an agent of interest and enumerating microbial taxa of interest in the sample in order to estimate the effects of the agent on the microbial taxa in the first subject.

In yet another aspect, this disclosure provides methods for both interpreting the results of an in vitro assay described herein and enabling practical use of such results in a variety of applications.

This disclosure also provides systems that may be useful in executing and/or interpreting any method described herein.

Microbial Ecology Shift Assay (MESA)

This disclosure provides in vitro assay methods for determining the effects of an agent on the microbiota of a given subject. Generally speaking, a method comprises the steps of: (a) obtaining a sample from a first subject; (b) contacting the sample with an agent in a reaction mixture; and (c) enumerating the abundance of one or more microbial taxa or taxon-identifying chemical species in the reaction mixture, after contacting the sample with the agent. Enumerations of microbial taxa may be direct such that microbial taxa of interest are directly enumerated, may be indirect such that taxon-identifying chemical species are enumerated, or may be a combination of both direct and indirect methods. Detection of taxon-identifying chemical species associated with microbial taxa of interest may also quantitatively measure the functionality of the microbial taxa of interest.

Subjects and Samples

Assays may be used to determine the effects of an agent on microbiota in a variety of different types of subjects. A subject may be any entity capable of hosting a microbiome and for which a microbiome may be identified. Non-limiting examples of different types of subjects include a species of a mammal, a species of a rodent, a species of a mouse, a species of a rat, a species of a dog, a species of a cat, a species of a hamster, a species of a monkey, a species of a pig, a species of a squirrel, a species a guinea pig, a species of a gerbil, a species of a bird, a species of a hydra, a species of a rabbit, a species of a fish, a species of a frog, a species of a cow, a species of a lamb, a species of a chicken, a species of *Drosphilia*, a species of *Xenopus*, a species of horse and a human. In some examples, a subject may be a species of a common laboratory animal, such as a species of mouse or rat. Moreover, a subject may be a wild-type species or may be a genetically-modified species. Furthermore, a subject may be gnotobiotic. A gnotobiotic subject may be, for example, a subject of a murine species lacking microbiota that is transplanted with human microbiota.

The type of sample used in an assay may vary depending on, for example, the subject of interest, the ease of obtaining the sample from the subject of interest, the amount of sample that may be obtained from a subject, the relationship between the microbial taxa of interest and a condition of interest, the site from which a sample is obtained, and combinations thereof. A sample may be any form of matter that comprises microbiota of the subject from which the sample is obtained, including, for example, a biological fluid or solid matter of biological origin. Non-limiting examples of types of samples include earwax, sweat, breast milk, hair, blood, bile, cerebrospinal fluid, lymphatic fluid, semen, vaginal discharge, menstrual fluid, feces, sputum, urine, saliva, secretions from open wounds, secretions from the eye, skin tissue (e.g., a skin biopsy), subcutaneous tissue, muscle tissue, adipose tissue, cells obtained from tissues, and combinations thereof.

Moreover, samples may be obtained from a variety of sources, including both internal environments, external surfaces, and body cavities. Non-limiting examples of sample sources include the gut, the vagina, the penis, a testicle, the cervix, the respiratory system, the ear, the skin, the rectum, the kidney, the liver, the spleen, the lung, the pancreas, the small intestine, the gallbladder, the lymph nodes, the colon, the cecum, a nasal passage, the central nervous system, an oral cavity, a sinus, a nare, the urogenital tract, an udder, an auditory canal, a breast, an open wound, the eye, muscle, fat, and combinations thereof. In some examples, samples may be obtained to indirectly represent microbial communities in other parts of a subject from which they were obtained. For example, fecal samples may be studied to assess the effect of an agent on microbial communities of the gut. Moreover, surgical means may be used to obtain samples from internal tissues, such, as, for example, the gut.

A solid sample obtained from a subject may be suspended in a liquid or a mixture of liquids to form a slurry. An aliquot of the slurry may then be used in an assay. A slurry may be useful, for example, in minimizing the abundance variability of appropriate microbial taxa between replicate aliquots of a solid sample, aiding in the preparation of a solid sample for a reaction mixture, preserving a solid sample, and combinations thereof. Additionally, a slurry may be in the form of a sample homogenate, wherein the size of the sample has been substantially reduced by mechanical (e.g., milling, sonication) and/or chemical means (e.g., treatment in concentrated acid, caustic) in the liquid comprising the slurry.

The concentration (referring to the percentage weight of sample per unit volume (w:v) slurry) of a slurry formed from a sample may vary depending upon, for example, the availability of sample, the availability of liquid(s) in which solid material is suspended, the size of a vessel in which a sample slurry is incubated with an agent, the particle size of the sample in the slurry, and combinations thereof. The concentration of a slurry used in an assay may be, for example, from about 0.01% to about 30%. In other examples, the concentration of a slurry used in an assay may be from about 0.1% to about 10%. In other examples, the concentration of a slurry used in an assay may be from about 3% to about 10%. In other examples, the concentration of a slurry used in an assay may be from about 1% to about 3%. In other examples, the concentration of a slurry used in an assay may be from about 0.1% to about 1%. In still other examples, the concentration of a slurry used in an assay may be about 0.01%, 0.01%, 1%, 2%, 3%, 4%, 5%, 6%, 7%, 8%, 9%, 10%, 20%, 30% or more.

In some examples, the concentration of a slurry used in an assay may be at least 0.01%. In other examples, the concentration of a slurry used in an assay may be at least 0.1%. In other examples, the concentration of a slurry used in an assay may be at least 1%. In other examples, the concentration of a slurry used in an assay may be at least 3%. In other examples, the concentration of a slurry used in an assay may be at least 10%. In still other examples, the concentration of a slurry used in an assay may be at least 0.01%, 0.01%, 1%, 2%, 3%, 4%, 5%, 6%, 7%, 8%, 9%, 10%, 20%, or 30%.

The type of liquid that may be used to form a sample slurry may vary, depending on, for example, the compatibility (i.e., degree to which liquid does not interfere with the sample) of the liquid with the sample, the necessary ionic strength or pH of the slurry, the compatibility of the liquid with other components (e.g., an agent of interest), temperature, level of oxygen in the liquid, level of nitrogen in the liquid, level of carbon dioxide in the liquid, and combinations thereof. Non-limiting examples of liquids that may be used to form a sample slurry include water, a buffer (e.g., phosphate buffered saline (PBS)), cell culture media, minimal media, conditioned media, serum, broth, blood broth, liquid agar, and combinations thereof.

Liquid samples obtained from a subject may be diluted with another liquid or a mixture of other liquids. An aliquot of the dilution may then be used in an assay. Dilution may be necessary, for example, to aid in sufficiently detecting microbial taxa, ensuring an appropriate proper sample-to-agent (or other reaction mixture component) ratio in reaction mixtures, preserving a sample after it is obtained from a subject, and combinations thereof. Non-limiting examples of liquids used for dilution include water, a buffer (e.g., phosphate buffered saline (PBS)), cell culture media, minimal media, conditioned media, serum, broth, blood broth, liquid agar, and combinations thereof.

Samples may be used immediately after acquisition from a subject, immediately after pre-processing (e.g., forming a sample slurry, diluting a liquid sample), or may be stored, either after receipt from a subject or after pre-processing, in a storage medium composition (e.g., storage medium comprising 1-20% ethanol, 1-10% glycerol, a buffer (e.g., phosphate buffered saline (PBS), and/or 1-10% dimethylsulfoxide (DMSO)), at reduced temperatures (for example, at or above −80° C.), and/or under anaerobic conditions.

A sample may be obtained from a single subject or samples may be obtained from multiple subjects of a group (e.g., a group of subjects all afflicted with a particular condition, a group of normal (i.e., healthy subjects), or multiple subjects of different groups. In the cases where samples are obtained from multiple subjects of a group, a pooled sample, to be used in an assay, may be generated from samples obtained from one or more subjects in the group. Alternatively, samples obtained from each subject in a group may be used in an assay separately.

Agents

The type of agent used in an assay may vary. An agent may be virtually any chemical species or combination of chemical species capable of being incubated with a given sample in a given reaction mixture. Non-limiting examples of agents that may be evaluated in an assay include a microbe (e.g., including bacteria), a virus, a prebiotic, a probiotic, a synbiotic, feces, cecal contents, a fecal transplant, a fecal slurry, a supernatant obtained from a fecal slurry, a cecal contents slurry, a supernatant obtained from a cecal contents slurry, a drug, an antibiotic, a food, a beverage, a nutraceutical, a supplement, a beauty care product (e.g., makeup, hairspray, lotion, cosmetics, lip balm, sunscreen, fragrances), personal hygiene product (e.g., shampoo, soap, shower gel, conditioner, chemically treated wipes, hand sanitizer), an allergen, a household chemical (e.g., bleach, ammonia, caustic household cleaning mixtures, fertilizer, gardening chemicals, paint, paint thinner, stain/water repellant (e.g., Scotchguard™)), wound dressings (e.g., bandages, liquid bandages), wound antiseptics (e.g., hydrogen peroxide), an industrial chemical (e.g., solvents, caustics, acids), a hazardous chemical, water from a municipal water source, an environmental sample (e.g., soil samples, water samples from natural sources), aerosols that may be inhaled via the nose or throat, topical pain relievers (e.g., Epsom salts), materials used to make clothing, a polynucleotide (e.g., deoxyribonucleic acid (DNA), ribonucleic acid (RNA), and combinations thereof), RNA capable of RNA-interference (RNAi), a polypeptide, a protein, a recombinant protein, a lipid, a carbohydrate, a sugar, a cell conditioned to secrete a chemical species, a microbial metabolite, a non-microbial metabolite, a detergent, a surfactant, a liposome, a drug delivery vehicle, a nanoparticle, and combinations thereof.

An agent may be a drug. The drug may be an approved drug already available in the marketplace, a drug previously available in the marketplace but subsequently withdrawn, a drug in development, an unapproved drug, or a chemical entity not already indicated as a drug. Comprehensive listings of drugs that may be agents in an assay can be found in reference materials such as the U.S. Food and Drug Administration Orange Book or the Merck Index, which are both incorporated herein in entirety by reference. Moreover, an agent may be formulated in a pharmaceutical composition that comprises the agent and, optionally, other desired species such as, for example, an excipient, stabilizer, carrier, or other agent included for sufficient agent delivery to its site of action and/or agent efficacy. Such a pharmaceutical composition may be used in an assay.

An agent may be evaluated in the absence of other agents or may be evaluated in combination with one or more other agents. In cases where a combination of agents is evaluated in an assay, the number of agents evaluated in combination may vary. In some examples, the number of agents evaluated in combination is from 2 agents to 100 agents. In other examples, the number of agents evaluated in combination is from 2 agents to 10 agents. In other examples, the number of agents evaluated in combination is from 2 agents to 5 agents. In still other examples, the number of agents evaluated in combination is 2, 3, 4, 5, 6, 7, 8, 9, 10, 11, 12, 13, 14, 15, 16, 17, 18, 19, 20, 30, 40, 50, 60, 70, 80, 90, 100, or more agents.

In some examples, the number of agents evaluated in combination is at least 2 agents. In other examples, the number of agents evaluated in combination is at least 10 agents. In other examples, the number of agents evaluated in combination is at least 50 agents. In still other examples, the number of agents evaluated in combination is at least 2, 3, 4, 5, 6, 7, 8, 9, 10, 11, 12, 13, 14, 15, 16, 17, 18, 19, 20, 30, 40, 50, 60, 70, 80, 90, 100, or more agents A set of related, chemically distinct agents may be evaluated in an assay, including a portion of a set. All agents in a set may be evaluated at once, a subset of agents in the set may be evaluated at once, or each agent in the set may be evaluated separately from the others. Non-limiting examples of a set of agents may be various diets of a food, a set of related drugs (e.g., a set of HMG-CoA reductase inhibitors, a set of drugs in development, a set of beta-blockers, a set of carbamazepines, etc., a set of drugs used in combination therapy, a set of compounds in a drug development pipeline, a set of approved drugs), a set of common household cleaners, a set of probiotics, a set of prebiotics, a set of medical foods, a set of natural products, a set of compounds generally recognized as safe (GRAS), a set of any of the agent types described herein, and combinations thereof.

The number of agents in a set may vary, depending upon, for example, the relationship between the agents of a set. For example, the number of agents in a set may be at least 2 agents. In other examples, the number of agents in a set may be at least 10 agents. In other examples, the number of agents in a set may be at least 1,000 agents. In other examples, the number of agents in a set may be at least 10,000 agents. In other examples, the number of agents in a set may be at least 100,000 agents. In other examples, the number of agents in a set may be at least 1,000,000 agents. In still other examples, the number of agents in a set may be at least 2, 10, 100, 1,000, 10,000, 100,000, or 1,000,000 agents.

In some examples, the number of agents in a set may be from 1 agent to 1,000,000 agents. In other examples, the number of agents in a set may be from 1 agent to 100,000 agents. In other examples, the number of agents in a set may be from 1 agent to 10,000 agents. In other examples, the number of agents in a set may be from 1 agent to 1,000 agents. In other examples, the number of agents in a set may be from 1 agent to 100 agents. In other examples, the number of agents in a set may be from 1 agent to 1000. In still other examples, the number of agents in a set may be 2, 10, 100, 1,000, 10,000, 100,000, or 1,000,000 agents.

An agent may be in any physical phase, including solid, liquid, or gas. Additionally, an agent may be dissolved in a liquid or mixture of liquids such that a solution of the agent is formed. Alternatively, an agent may not be readily soluble in a liquid or mixture of liquids, and instead forms a suspension when introduced into a liquid or mixture of liquids.

Reaction Mixtures

In general, a sample may be combined with one or more agents of interest and any additional reagents to form a reaction mixture that is then subjected to the appropriate incubation conditions. In one example, control reaction mixtures do not comprise the agent of interest. Additional reagents may be necessary, for example, to preserve the sample; to dilute a sample; to maintain the appropriate pH of the reaction mixture; to slurry a sample; to solubilize a sample; to maintain the appropriate ionic strength of a reaction mixture; to improve the dispersion of a sample that has been slurried; to maintain appropriate conditions for resident microbiota; to solubilize an agent, to bring a reaction mixture up to appropriate volume, to improve detection of signals, to improve the differentiation of different signals during detection, to detect one or more specific signals, to query a particular readout, and combinations thereof. Non-limiting examples of additional reagents that are comprised in a reaction mixture include culture media, water, buffer (e.g., phosphate buffered saline (PBS)), glycerol, DMSO, Triton-X-100, adenosine triphosphate (ATP), vitamins, stearic acid, lithocholic acid, bile salts, cysteine, hemin, Tween-80, and combinations thereof.

A reaction mixture may be a liquid reaction mixture (e.g., liquid sample+liquid additional reagents+agent of interest dissolved in a liquid), may be a solid reaction mixture (e.g., solid sample+solid reagents+solid agent of interest), or may be a combination thereof (e.g. slurried sample+liquid additional reagents+agent of interest in solution).

The volume of a reaction mixture may vary depending on, for example, the availability of sample, the size of available vessels in which to contain a reaction mixture, the availability of additional reagents, the requirements for sufficient detection of microbial taxa or taxon-identifying chemical species, conditions (e.g., temperature, oxygen-content, humidity, pH, incubation time, etc.) required for incubation, the particular microbial taxa or taxon-identifying chemical species of interest, the need for high-throughput methods, and combinations thereof. In some examples, the volume of a reaction mixture may be from about 0.01 milliliters ("mL") to about 10 mL. In other examples, the volume of a reaction mixture may be from about 0.1 mL to about 1 mL. In other examples, the volume of a reaction mixture may be from about 0.1 mL to about 0.5 mL. In still other examples, the volume of a reaction mixture may be about 0.01, 0.02, 0.03, 0.04, 0.05, 0.06, 0.07, 0.08, 0.09, 0.10, 0.15, 0.20, 0.25, 0.30, 0.35, 0.40, 0.45, 0.50, 0.55, 0.60, 0.65, 0.70, 0.75, 0.80, 0.85, 0.90, 0.95, 1.0, 2.0, 3.0, 4.0, 5.0, 6.0, 7.0, 8.0, 9.0, 10.0 mL, or more.

In some examples, the volume of a reaction mixture may be at least 0.01 mL. In other examples, the volume of a reaction mixture may be at least 0.1 mL. In other examples, the volume of a reaction mixture may be at least 1 mL. In still other examples, the volume of a reaction mixture may be at least 0.01, 0.02, 0.03, 0.04, 0.05, 0.06, 0.07, 0.08, 0.09, 0.10, 0.15, 0.20, 0.25, 0.30, 0.35, 0.40, 0.45, 0.50, 0.55, 0.60, 0.65, 0.70, 0.75, 0.80, 0.85, 0.90, 0.95, 1.0, 2.0, 3.0, 4.0, 5.0, 6.0, 7.0, 8.0, 9.0, 10.0 mL, or more.

In some examples, the volume of a reaction mixture may be at most 10 mL. In other examples, the volume of a reaction mixture may be at most 1 mL. In other examples, the volume of a reaction mixture may be at most 0.5 mL. In other examples, the volume of a reaction mixture may be at most 0.1 mL. In still other examples, the volume of a reaction mixture may be at most 0.01, 0.02, 0.03, 0.04, 0.05, 0.06, 0.07, 0.08, 0.09, 0.10, 0.15, 0.20, 0.25, 0.30, 0.35, 0.40, 0.45, 0.50, 0.55, 0.60, 0.65, 0.70, 0.75, 0.80, 0.85, 0.90, 0.95, 1.0, 2.0, 3.0, 4.0, 5.0, 6.0, 7.0, 8.0, 9.0, or 10.0 mL.

The amount of a solid sample in a reaction mixture may vary depending on, for example, the type of sample, the availability of sample, the abundance of microbial taxa or taxon-identifying chemical species of interest in the sample, the concentration at which a sample slurry comprising the solid sample was generated, the availability of an agent of interest, the necessary conditions for sufficient detection of microbial taxa or taxon-identifying chemical species of interest, conditions (e.g., temperature, oxygen-content, humidity, pH, incubation time, etc.) required for incubation, the type of additional reagents in a reaction mixture, the concentration of additional reagents in a reaction mixture, the particular microbial taxa or taxon-identifying chemical species of interest, and combinations thereof. The amount of a solid sample in a reaction mixture may be, for example, from about 1 nanogram ("ng") to about 100 milligrams ("mg"). In other examples, the amount of a solid sample in a reaction mixture may be from about 10 ng to about 100 mg. In other examples, the amount of a solid sample in a reaction mixture may be from about 10 ng to about 1 mg. In still other examples, the amount of a solid sample in a reaction mixture may be about 1, 10, 100, or 500 ng, 1, 10, 100, or 500 micrograms ("µg"), 1, 10, or 100 mg.

In some examples, the amount of a solid sample in a reaction mixture may be at least 1 ng. In other examples, the amount of a solid sample in a reaction mixture may be at least 1 µg. In other examples, the amount of a solid sample in a reaction mixture may be at least 1 mg. In other examples, the amount of a solid sample in a reaction mixture may be at least 10 mg. In still other examples, the amount of a solid sample in a reaction mixture may be at least 1, 10, 100, or 500 ng, 1, 10, 100, or 500 g, 1, 10, or 100 mg.

In some examples, the amount of a solid sample in a reaction mixture may be at most 100 mg. In other examples, the amount of a solid sample in a reaction mixture may be at most 10 mg. In other examples, the amount of a solid sample in a reaction mixture may be at most 1 mg. In other examples, the amount of a solid sample in a reaction mixture may be at most 1 g. In still other examples, the amount of a solid sample in a reaction mixture may be at most 1, 10, 100, or 500 ng, 1, 10, 100, or 500 g, 1, 10, or 100 mg.

In cases where a slurry is added to a reaction volume, the volume percentage of a slurry in a reaction mixture may vary depending on, for example, the concentration of the prepared slurry. For example, the volume percentage of slurry in a reaction mixture may be from about 0.1% to about 100%. In other examples, the volume percentage of slurry in a reaction mixture may be from about 0.1% to 10%. In other examples, the volume percentage of slurry in a reaction mixture may be from about 0.1% to 2%. In still other examples, the volume percentage of slurry in a reaction mixture may be at least about 0.1%, 0.2%, 0.3%, 0.4%, 0.5%, 0.6%, 0.7%, 0.8%, 0.9%, 1.0%, 1.2%, 1.4%, 1.6%, 1.8%, 2.0%, 2.5%, 3.0%, 3.5%, 4.0%, 4.5%, 5.0%, 5.5%, 6.0%, 6.5%, 7.0%, 7.5%, 8.0%, 8.5%, 9.0%, 9.5%, 10%, 15%, 20%, 30%, 40%, 50%, 60%, 70%, 80%, 90%, or 99%.

In some examples, the volume percentage of slurry in a reaction mixture may be at least about 0.1%. In other examples, the volume percentage of slurry in a reaction mixture may be at least about 1%. In other examples, the volume percentage of slurry in a reaction mixture may be at least about 10%. In other examples, the volume percentage of slurry in a reaction mixture may be at least about 50%. In still other examples, the volume percentage of slurry in a reaction mixture may be at least about 0.1%, 0.2%, 0.3%, 0.4%, 0.5%, 0.6%, 0.7%, 0.8%, 0.9%, 1.0%, 1.2%, 1.4%, 1.6%, 1.8%, 2.0%, 2.5%, 3.0%, 3.5%, 4.0%, 4.5%, 5.0%, 5.5%, 6.0%, 6.5%, 7.0%, 7.5%, 8.0%, 8.5%, 9.0%, 9.5%, 10%, 15%, 20%, 30%, 40%, 50%, 60%, 70%, 80%, 90%, or 99%.

In some examples, the volume percentage of slurry in a reaction mixture may be at most about 50%. In other examples, the volume percentage of slurry in a reaction mixture may be at most about 10%. In other examples, the volume percentage of slurry in a reaction mixture may be at most about 1%. In other examples, the volume percentage of slurry in a reaction mixture may be at most about 0.1%. In still other examples, the volume percentage of slurry in a reaction mixture may be at most about 0.1%, 0.2%, 0.3%, 0.4%, 0.5%, 0.6%, 0.7%, 0.8%, 0.9%, 1.0%, 1.2%, 1.4%, 1.6%, 1.8%, 2.0%, 2.5%, 3.0%, 3.5%, 4.0%, 4.5%, 5.0%, 5.5%, 6.0%, 6.5%, 7.0%, 7.5%, 8.0%, 8.5%, 9.0%, 9.5%, 10%, 15%, 20%, 30%, 40%, 50%, 60%, 70%, 80%, 90%, or 99%.

The concentration (referring to the percentage volume of liquid sample per unit volume of reaction mixture) of a liquid sample in a reaction mixture may vary depending on, for example, the type of sample, the availability of sample, the abundance of microbial taxa or taxon-identifying chemical species of interest in the sample, the availability of an agent of interest, the necessary conditions for sufficient detection of microbial taxa or taxon-identifying chemical species of interest, conditions (e.g., temperature, oxygen-content, humidity, pH, incubation time, etc.) required for incubation, the particular microbial taxa or taxon-identifying chemical species of interest, and combinations thereof. The concentration of a liquid sample in a reaction mixture may be, for example, from about 0.01% to about 50%. In other examples, the concentration of a liquid sample in a reaction mixture may be from about 0.05% to about 20%. In other examples, the concentration of a liquid sample in a reaction mixture may be from about 0.05% to 10%. In still other examples, the concentration of a liquid sample in a reaction mixture may be about 0.01%, 0.1%, 1%, 2%, 3%, 4%, 5%, 6%, 7%, 8%, 9%, 10%, 15%, 20%, 25%, 30%, 40%, or 50%.

In some examples, the concentration of a liquid sample in a reaction mixture may be at least 0.01%. In other examples, the concentration of a liquid sample in a reaction mixture may be at least 0.1%. In other examples, the concentration of a liquid sample in a reaction mixture may be at least 1%. In other examples, the concentration of a liquid sample in a reaction mixture may be at least 5%. In still other examples, the concentration of a liquid sample in a reaction mixture may be at least 0.01%, 0.1%, 1%, 2%, 3%, 4%, 5%, 6%, 7%, 8%, 9%, 10%, 15%, 20%, 25%, 30%, 40%, or 50%.

In some examples, the concentration of a liquid sample in a reaction mixture may be at most 5%. In other examples, the concentration of a liquid sample in a reaction mixture may be at most 1%. In other examples, the concentration of a liquid sample in a reaction mixture may be at most 0.1%. In other examples, the concentration of a liquid sample in a reaction mixture may be at most 0.01%. In still other examples, the concentration of a liquid sample in a reaction mixture may be at most 0.01%, 0.1%, 1%, 2%, 3%, 4%, 5%, 6%, 7%, 8%, 9%, 10%, 15%, 20%, 25%, 30%, 40%, or 50%.

The concentration (referring to the percentage weight of agent per unit volume of reaction mixture) of an agent of interest in a reaction mixture may vary depending on, for example, the type of agent, the availability of the agent of interest, the availability of sample, the concentration of an agent in a solution added to a reaction mixture, the abundance of microbial taxa or taxon-identifying chemical species of interest in a sample, the necessary conditions for sufficient detection of microbial taxa or taxon-identifying chemical species of interest, conditions (e.g., temperature, oxygen-content, humidity, pH, incubation time, etc.) required for incubation, the particular microbial taxa or taxon-identifying chemical species of interest, and combinations thereof. The concentration of an agent in a reaction mixture may be from about from about 0.01% to about 50%. In other examples, the concentration of an agent in a reaction mixture may be from about 0.05% to about 20%. In other examples, the concentration of an agent in a reaction mixture may be from about 0.05% to 10%. In still other examples, the concentration of an agent in a reaction mixture may be about 0.01%, 0.1%, 1%, 2%, 3%, 4%, 5%, 6%, 7%, 8%, 9%, 10%, 15%, 20%, 25%, 30%, 40%, or 50%.

In some examples, the concentration of an agent in a reaction mixture may be at least 0.01%. In other examples, the concentration of an agent in a reaction mixture may be at least 0.1%. In other examples, the concentration of an agent in a reaction mixture may be at least 1%. In other examples, the concentration of an agent in a reaction mixture may be at least 5%. In still other examples, the concentration of an agent in a reaction mixture may be at least 0.01%, 0.1%, 1%, 2%, 3%, 4%, 5%, 6%, 7%, 8%, 9%, 10%, 15%, 20%, 25%, 30%, 40%, or 50%.

In some examples, the concentration of an agent in a reaction mixture may be at most 5%. In other examples, the concentration of an agent in a reaction mixture may be at most 1%. In other examples, the concentration of an agent in a reaction mixture may be at most 0.1%. In other examples, the concentration of an agent in a reaction mixture may be at most 0.01%. In still other examples, the concentration of an agent in a reaction mixture may be at most 0.01%, 0.1%, 1%, 2%, 3%, 4%, 5%, 6%, 7%, 8%, 9%, 10%, 15%, 20%, 25%, 30%, 40%, or 50%.

A reaction mixture may be contained in a variety of different types of vessels. The vessel chosen to contain a reaction mixture may depend, for example, on the volume of a reaction mixture, available equipment for incubating the reaction mixture, the number of reaction mixtures desired for evaluation, and combinations thereof. Non-limiting examples of vessels that may be used to contain a reaction mixture include centrifuge tubes, beakers, flasks, graduated cylinders, bottles, micro-centrifuge tubes, test tubes, cuvettes, microwell plates (referred to herein as a "microplate"—e.g., comprising at least about 2 wells, 4 wells, 6, wells, 8 wells, 12 wells, 24 wells, 36 wells, 48 wells, 54 wells, 60 wells, 66 wells, 72 wells, 78 wells, 84 wells, 90 wells or 96 wells, 144 wells, 192 wells, 384 wells, 768, 1536 wells, 3072 wells, 6144 wells, 12228 wells, or more), capillary tubes, and tissue culture plates (e.g., at least 10 mm diameter, at least 35 mm diameter, at least 100 mm diameter, at least 150 mm diameter).

A single reaction mixture may be generated for a sample or multiple reaction mixtures may be generated for a given sample. Identical replicate reaction mixtures may be used for replicate incubations or differing incubations. For example, a sample slurry may be generated from a solid sample and aliquots of the sample slurry used to generate replicate reaction mixtures each comprising identical components in identical amounts. The replicate reaction mixtures may also be incubated at the same conditions. Alternatively, replicate aliquots of the sample slurry may be used to evaluate different conditions, such as, for example, differing incubation conditions, differing levels of an agent of interest in the reaction mixture, or entirely different types of agents in the reaction mixture. Moreover, in analogous fashion, a liquid sample may be obtained and aliquots of the sample may be used to generate replicate reaction mixtures.

In the case where replicate reaction mixtures are prepared for a sample, each reaction mixture may be contained, for example, in a well of a microplate or the like. Micronization of multiple reaction mixtures into a vessel designed to contain multiple reaction mixtures, such as a microplate, may be useful for achieving higher assay throughput, as a larger number of reaction mixtures may be more easily incubated and/or evaluated at once when compared to other means, such as, for example, single reaction mixture tubes.

Incubation Conditions

After a reaction mixture is prepared, the reaction mixture may then be incubated at a given set of conditions. In some cases, control reaction mixtures may not be subject to incubation. Conditions necessary for a given incubation may vary depending on, for example, the type of sample, the type of agent, the amount or concentration of sample in a reaction mixture, in interactions of an agent with microbial taxa of interest, the amount or concentration of an agent of interest in a reaction mixture, the abundance of microbial taxa or taxon-identifying chemical species of interest in a reaction mixture, the type of microbial taxa or taxon-identifying chemical species of interest, the size of a reaction mixture, the amount of additional reagents in a reaction mixture, the type of additional reagents in a reaction mixture, the availability of necessary equipment for incubation, the number of reaction mixtures, and combinations thereof. Moreover, non-limiting examples of conditions that may be included in executing an assay include time of incubation, temperature, relative humidity, levels of oxygen ($O_2$) in an incubation atmosphere, levels of carbon dioxide ($CO_2$) in an incubation atmosphere, and levels of nitrogen ($N_2$) in an incubation atmosphere.

The time for which a reaction mixture is incubated (herein referred to as "incubation time") may vary. For example, a reaction mixture may be subject to an incubation time from about 1 minute ("min") to about 5 days. In other examples, a reaction mixture may be subject to an incubation time from about 2 hours ("hr") to about 2 days. In other examples, a reaction mixture may be subject to an incubation time from about 12 hours to 2 days. In still other examples, a reaction mixture may be subject to an incubation time from about 1 min, or 1, 2, 3, 4, 5, 6, 7, 8, 9, 10, 11, 12, 13, 14, 15, 16, 17, 18, 19, 20, 21, 22, 23, or 24 hr, 1, 2, 3, 4, or 5 days.

In some examples, a reaction mixture may be subject to an incubation time of at least 1 min. In other examples, a reaction mixture may be subject to an incubation time of at least 1 hr. In other examples, a reaction mixture may be subject to an incubation time of at least 1 day. In still other examples, a reaction mixture may be subject to an incubation time of at least 1 min, or 1, 2, 3, 4, 5, 6, 7, 8, 9, 10, 11, 12, 13, 14, 15, 16, 17, 18, 19, 20, 21, 22, 23, or 24 hr, 1, 2, 3, 4, or 5 days.

In some examples, a reaction mixture may be subject to an incubation time of at most 2 days. In other examples, a reaction mixture may be subject to an incubation time of at most 12 hrs. In other examples, a reaction mixture may be subject to an incubation time of at most 6 hrs. In still other examples, a reaction mixture may be subject to an incubation time of at most 1 min, or 1, 2, 3, 4, 5, 6, 7, 8, 9, 10, 11, 12, 13, 14, 15, 16, 17, 18, 19, 20, 21, 22, 23, or 24 hr, 1, 2, 3, 4, or 5 days.

The temperature at which a reaction mixture is incubated (herein referred to as "incubation temperature") may vary. The incubation temperature may be held constant throughout the course of incubation or may be made to vary. For example, the incubation temperature may be from about 2 degrees Celsius ("° C.") to about 60° C. In other examples, the incubation temperature may be from about 4° C. to about 50° C. In other examples, the incubation temperature may be from about 4° C. to about 42° C. In still other examples, the incubation temperature may be about 1° C., 2° C., 3° C., 4° C., 5° C., 6° C., 7° C., 8° C., 9° C., 10° C., 11° C., 12° C., 13° C., 14° C., 15° C., 16° C., 17° C., 18° C., 19° C., 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., 45° C., 46° C., 47° C., 48° C., 49° C., 50° C. or 60° C.

In some examples, the incubation temperature is at least 1° C. In other examples, the incubation temperature is at least 10° C. In other examples, the incubation temperature is at least 20° C. In other examples, the incubation temperature is at least 30° C. In other examples, the incubation temperature is at least 40° C. In still other examples, the incubation temperature is at least 1° C., 2° C., 3° C., 4° C., 5° C., 6° C., 7° C., 8° C., 9° C., 10° C., 11° C., 12° C., 13° C., 14° C., 15° C., 16° C., 17° C., 18° C., 19° C., 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., 45° C., 46° C., 47° C., 48° C., 49° C., 50° C. or 60° C.

In some examples, the incubation temperature is at most 60° C. In other examples, the incubation temperature is at most 50° C. In other examples, the incubation temperature is at most 30° C. In other examples, the incubation temperature is at most 30° C. In other examples, the incubation temperature is at most 20° C. In still other examples, the incubation temperature is at most 1° C., 2° C., 3° C., 4° C., 5° C., 6° C., 7° C., 8° C., 9° C., 10° C., 11° C., 12° C., 13° C., 14° C., 15° C., 16° C., 17° C., 18° C., 19° C., 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., 45° C., 46° C., 47° C., 48° C., 49° C., 50° C. or 60° C.

The relative humidity at which a reaction mixture is incubated (herein referred to as "incubation humidity") may vary. The incubation humidity may be held constant throughout the course of incubation or may be made to vary. For example, the incubation humidity may be from about 0% to about 100%. In some examples, the incubation humidity may be from about 20% to 100%. In some examples, the incubation humidity may be from about 30% to about 100%. In still other examples, the incubation humidity may be about 0%, 5%, 10%, 20%, 30%, 40%, 50%, 60%, 70%, 80%, 90%, or 100%.

In some examples, the incubation humidity may be at least 0.1%. In some examples, the incubation humidity may be at least 10%. In some examples, the incubation humidity may be at least 30%. In still other examples, the incubation humidity may be at least 0.1%, 5%, 10%, 20%, 30%, 40%, 50%, 60%, 70%, 80%, 90%, or 99%.

In some examples, the incubation humidity may be at most 100%. In some examples, the incubation humidity may be at most 75%. In some examples, the incubation humidity may be at most 25%. In still other examples, the incubation humidity may be at most 0.1%, 5%, 10%, 20%, 30%, 40%, 50%, 60%, 70%, 80%, 90%, or 99%.

The levels of oxygen ($O_2$) in an incubation atmosphere may vary. An "incubation atmosphere" as used herein generally refers to the local environment in which the incubation of a reaction mixture takes place. In some cases, an incubation atmosphere is anaerobic in that the incubation atmosphere comprises no oxygen. Alternatively, an incubation atmosphere is aerobic. In some examples, an incubation atmosphere comprises a volume percentage of oxygen from about 0.5% oxygen to about 100% oxygen. In other examples, an incubation atmosphere comprises a volume percentage of oxygen from about 0.5% oxygen to about 50% oxygen. In other examples, an incubation atmosphere comprises a volume percentage of oxygen from about 0.5% oxygen to about 10% oxygen. In other examples, an incubation atmosphere comprises a volume percentage of oxygen from about 0.5% oxygen to about 5% oxygen. In still other examples, an incubation atmosphere comprises a volume percentage of oxygen of about 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, or 99% oxygen.

In some examples, an incubation atmosphere comprises a volume percentage of oxygen at least about 0.5% oxygen. In other examples, an incubation atmosphere comprises a volume percentage of oxygen at least about 5% oxygen. In other examples, an incubation atmosphere comprises a volume percentage of oxygen at least about 10% oxygen. In other examples, an incubation atmosphere comprises a volume percentage of oxygen at least about 50% oxygen. In still other examples, an incubation atmosphere comprises a volume percentage of oxygen at least about 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, or 99% oxygen.

In some examples, an incubation atmosphere comprises a volume percentage of oxygen at most about 50% oxygen. In other examples, an incubation atmosphere comprises a volume percentage of oxygen at most about 10% oxygen. In other examples, an incubation atmosphere comprises a volume percentage of oxygen at most about 5% oxygen. In other examples, an incubation atmosphere comprises a volume percentage of oxygen at most about 0.5% oxygen. In still other examples, an incubation atmosphere comprises a volume percentage of oxygen at most about 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, or 99% oxygen.

The levels of carbon dioxide ($CO_2$) in an incubation atmosphere may vary. In some cases, an incubation atmosphere comprises no carbon dioxide. In some examples, an incubation atmosphere comprises a volume percentage of carbon dioxide from about 0.5% carbon dioxide to about 100% carbon dioxide. In other examples, an incubation atmosphere comprises a volume percentage of carbon dioxide from about 0.5% carbon dioxide to about 50% carbon dioxide. In other examples, an incubation atmosphere comprises a volume percentage of carbon dioxide from about 0.5% carbon dioxide to about 10% carbon dioxide. In other examples, an incubation atmosphere comprises a volume percentage of carbon dioxide from about 0.5% carbon dioxide to about 5% carbon dioxide. In still other examples, an incubation atmosphere comprises a volume percentage of carbon dioxide of about 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, or 99% carbon dioxide.

In some examples, an incubation atmosphere comprises a volume percentage of carbon dioxide at least about 0.5% carbon dioxide. In other examples, an incubation atmosphere comprises a volume percentage of carbon dioxide at least about 5% carbon dioxide. In other examples, an incubation atmosphere comprises a volume percentage of carbon dioxide at least about 10% carbon dioxide. In other examples, an incubation atmosphere comprises a volume percentage of carbon dioxide at least about 50% carbon dioxide. In still other examples, an incubation atmosphere comprises a volume percentage of carbon dioxide at least about 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, or 99% carbon dioxide.

In some examples, an incubation atmosphere comprises a volume percentage of carbon dioxide at most about 50% carbon dioxide. In other examples, an incubation atmosphere comprises a volume percentage of carbon dioxide at most about 10% carbon dioxide. In other examples, an incubation atmosphere comprises a volume percentage of carbon dioxide at most about 5% carbon dioxide. In other examples, an incubation atmosphere comprises a volume percentage of carbon dioxide at most about 0.5% carbon dioxide. In still other examples, an incubation atmosphere comprises a volume percentage of carbon dioxide at most about 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, or 99% carbon dioxide.

The levels of nitrogen ($N_2$) in an incubation atmosphere may vary. In some cases, an incubation atmosphere comprises no nitrogen. In some examples, an incubation atmosphere comprises a volume percentage of nitrogen from about 0.5% nitrogen to about 100% nitrogen. In other examples, an incubation atmosphere comprises a volume percentage of nitrogen from about 0.5% nitrogen to about 50% nitrogen. In other examples, an incubation atmosphere comprises a volume percentage of nitrogen from about 0.5% nitrogen to about 10% nitrogen. In other examples, an incubation atmosphere comprises a volume percentage of nitrogen from about 0.5% nitrogen to about 5% nitrogen. In still other examples, an incubation atmosphere comprises a volume percentage of nitrogen of about 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, or 99% nitrogen.

In some examples, an incubation atmosphere comprises a volume percentage of nitrogen at least about 0.5% nitrogen. In other examples, an incubation atmosphere comprises a volume percentage of nitrogen at least about 5% nitrogen. In other examples, an incubation atmosphere comprises a volume percentage of nitrogen at least about 10% nitrogen. In other examples, an incubation atmosphere comprises a volume percentage of nitrogen at least about 50% nitrogen. In still other examples, an incubation atmosphere comprises a volume percentage of nitrogen at least about 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, or 99% nitrogen.

In some examples, an incubation atmosphere comprises a volume percentage of nitrogen at most about 50% nitrogen. In other examples, an incubation atmosphere comprises a volume percentage of nitrogen at most about 10% nitrogen. In other examples, an incubation atmosphere comprises a volume percentage of nitrogen at most about 5% nitrogen. In other examples, an incubation atmosphere comprises a volume percentage of nitrogen at most about 0.5% nitrogen. In still other examples, an incubation atmosphere comprises a volume percentage of nitrogen at most about 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, or 99% nitrogen.

Enumerating Microbial Taxa and/or Taxon-Identifying Chemical Species and Data Analysis Microbial taxa may be enumerated by a variety of means depending upon the desired route and/or available instrumentation. In some cases, microbial taxa may be enumerated by quantitatively detecting one or more taxon-identifying chemical species associated with a given microbial taxon in a sample. Moreover, enumerations of taxon-identifying chemical species may be used to indicate function of a given microbial taxon. Non-limiting examples of such chemical species include small-molecules (including metabolites), proteins, lipids, nucleic acids, and/or carbohydrates.

In some cases, a detected molecule may be a common structural component of a group of organisms comprised in a microbial taxon. For example, a protein type or lipid associated with the plasma membrane of a microbe may be detected. In addition, a molecule secreted may be detected. For example, some bacteria are known to produce short-chain fatty acids such as butyrate, propionate, valerate, and acetate. Secretion of a species such as butyrate, for example, may be the common characteristic used to group organisms into a given microbial taxon. The detection of butyrate may then be used to enumerate the abundance of the respective microbial taxon in a sample. Moreover, a molecule, for example, may be a common metabolite produced by organisms within a given microbial taxon. Detection of that metabolite may then be used to enumerate the abundance of that microbial taxon in a sample and/or the functionality of that taxon. Furthermore, detection of one or more molecules in combination may be used to enumerate a microbial taxon.

Detection of a molecule may be achieved with a variety of methods that include spectroscopic methods. Non-limiting examples of spectroscopic methods that may be used in enumerating microbial taxa include optical methods (e.g., UV-V is absorbance, fluorescence, bioluminescence, Fourier-transform infrared (FT-IR) spectroscopy), nuclear magnetic resonance (NMR) spectroscopy, dynamic light scattering, and mass spectrometry.

Nucleic acids may be detected and quantified in order to enumerate microbial taxa. Such methods may be especially useful in cases where microbial taxa are operational taxonomic units (OTUs) distinguished by one or more gene sequence homologies. Detected nucleic acids may be deoxyribonucleic acid (DNA), ribonucleic acid (RNA), or combinations thereof. Nucleic acids may be detected generically, without respect to sequence, or may be detected in a sequence specific manner. In cases where sequence specific detection is desired, detection of a nucleic acid may be completed by the detection of a full-length gene sequence or may be completed by the detection of a partial-length gene sequence.

Moreover, nucleic acids may be downstream molecules synthesized as the result of gene transcription and/or metagenomic molecules present in a living organism. In general, a metagenomic molecule may be a genetic molecule that may be recovered from an environmental sample, such as a living organism. For example, in the case of the 16S ribosomal RNA (rRNA) gene, genomic DNA corresponding, in whole or part, to regions of the 16S rRNA gene, messenger RNA (mRNA) transcripts, in whole or part, of the 16S rRNA gene, and/or functional 16S rRNA may be detected and used to enumerate the abundance of a microbial taxon characterized by sequence homology of a particular 16S rRNA gene sequence.

Nucleic acid sequencing methods may be used to detect and quantify sequence specific nucleic acids such that they are used to enumerate the abundance of a microbial taxon characterized by homology of the detected sequence amongst organisms clustered into the microbial taxon. Non-limiting examples of sequencing methods that may be used include shotgun sequencing, polymerase chain reaction, real-time polymerase chain reaction, ligase chain reaction, single-molecule real-time sequencing, ion torrent sequencing, pyrosequencing, sequencing by synthesis, sequencing by ligation, chain termination sequencing, massively parallel signature sequencing, polony sequencing, SOLiD sequencing, DNA nanoball sequencing, heliscope single molecule sequencing, single molecule real time sequencing, nanopore sequencing, mass spectrometry sequencing, microfluidic sequencing, high-throughput sequencing, Illumina sequencing, HiSeq sequencing, MiSeq sequencing, or combinations thereof. Sequencing may be completed such that full-length genes are sequenced or partial-length genes are sequenced.

Sequence-specific detection of nucleic acids may also be completed with oligonucleotide probes. An oligonucleotide probe may be capable of hybridizing with a full-length or partial-length gene sequence of interest. Moreover, an oligonucleotide probe may be labeled with a detectable tag, such as a fluorescent dye, that may be detected. Alternatively, nucleic acid to be probed may be labeled such that its binding with the oligonucleotide probe is detected (via an attached label). An oligonucleotide probe may be a primer or a longer, different type of oligonucleotide. The oligonucleotide probe may the same type of nucleic acid as the target (e.g., DNA target and DNA oligonucleotide) or the oligonucleotide probe may be a different type of nucleic acid than the target (e.g., DNA target and RNA probe). Non-limiting examples of a label linked to an oligonucleotide probe may be a fluorescent dye, absorbent chemical species, radiolabel, quantum dot, or nanoparticle. Moreover, an oligonucleotide probe may also include a quencher (a molecule used, for example, to inhibit fluorescence). Probes useful in real-time polymerase chain reactions may be useful in sequence specific detection. Non-limiting examples of such probes include TaqMan probes, TaqMan Tamara probes, TaqMan MGB probes, or Lion probes.

Prior to sequencing, nucleic acids to be sequenced may be amplified.

Oligonucleotide probes may be immobilized to an array such that the binding of a target nucleic acid sequence is detected. In some examples, such oligonucleotide probes may be immobilized in one or more arrays. Each oligonucleotide probe is assigned a specific position in the array such that the position corresponds to the oligonucleotide probe. Nucleic acids to-be-detected may be labeled with an agent capable of being detected. Hybridization of a labeled nucleic acids to a complementary, immobilized sequence results in accumulation of detectable label at the signal which can then be identified indirectly as presence of the a given sequence. Nucleic acids to-be-analyzed may be exposed to an oligonucleotide probe array without size reduction or may be fragmented in order to ensure that the size of the to-be-analyzed nucleic acid is more similar to the oligonucleotide probes arranged on the array. Size similarity may result in better nucleic acid binding to oligonucleotide probes of the array. Oligonucleotide probe arrays have been generated for taxonomic analyses based on the sequence-specific detection of nucleic acids. Non-limiting examples of such arrays include the G2 PhyloChip™ and G3 PhyloChip™. The selection of oligonucleotide probes, the construction of each array, methods for obtaining data, and methods for analysis of data obtained from each array are described in detail in U.S. Patent Application Publication No. 2009/0291858 and U.S. Patent Application Publication No. 2012/0165215 which are both incorporated in entirety herein by reference.

Oligonucleotide probes may be immobilized on microbeads. Binding of nucleic acids to oligonucleotide probes arranged on microbeads and detection of such nucleic acids is completed in an analogous fashion to that mentioned above for oligonucleotides, such that nucleic acids to-be-analyzed are labeled and their hybridization with an oligonucleotide probe results in the accumulation of detectable signal that can be indirectly interpreted as the presence of a sequence specific region of nucleic acid. Again, nucleic acids to-be-analyzed may be exposed to oligonucleotide probes on microbeads without size reduction or may be fragmented in order to ensure that the size of the to-be-analyzed nucleic acid is more similar to the oligonucleotide probes arranged on the microbeads.

DNA barcoding may aid in enumerating microbial taxa. DNA samples from multiple subjects and time points may be PCR amplified using primers that incorporate a unique DNA barcode in addition to the 16S rRNA priming sites. Produced amplicons may then be pooled together and sequenced in a single batch.

Enumeration of microbial taxa may also be achieved by other means such as analyzing proteomes, transcriptomes, metabolomes, or combinations thereof. For example, microbial RNA transcripts, proteins, non-16S genes, etc. may be profiled and their abundance used to determine the impact of the agent on the microbial communities.

An enumeration of microbial taxa and/or taxon-identifying chemical species in a reaction mixture (herein referred to as "enumeration") may be completed both prior to and at one or more time points after adding an agent to the reaction mixture. An aliquot of the reaction mixture may be used for enumerations at each desired time point or the entire reaction mixture may be used for a single time point. In one example, enumerations are completed at a time point immediately following the addition of an agent to a reaction mixture and at subsequent time points after addition of the agent. Moreover, enumerations determined for a reaction mixture may be back-calculated (using the appropriate assay protocol, reagent ratios, etc.) such that an enumeration is determined for the original sample.

The number of time points for which microbial taxa and/or taxon-identifying chemical species are enumerated may vary depending upon, for example, the number of microbial taxa to be enumerated, the duration of agent action (if any) on the microbial taxa and/or taxon-identifying chemical species of interest, incubation conditions, and combinations thereof. For example, the number of time points for which microbial taxa and/or taxon-identifying chemical species are enumerated is at least 1 time point. In other examples the number of time points for which microbial taxa and/or taxon-identifying chemical species are enumerated is at least 10 time points. In other examples, the number of time points for which microbial taxa and/or taxon-identifying chemical species are enumerated is at least 30 time points. In still other examples, the number of time points for which microbial taxa and/or taxon-identifying chemical species are enumerated is at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or more time points.

The time interval between time points for which microbial taxa and/or taxon-identifying chemical species are enumerated may vary. Intervals may be equally spaced between time points (e.g., for example, a time point is taken every 5 minutes) or intervals may be spaced such that intervals are different between different time points (e.g., a time point is taken at 5 minutes, 10 minutes, 20 minutes, 50 minutes, 100 minutes, etc.). Moreover, the duration of a time interval between time points may vary. In some examples, the duration of the time interval between time points may be at least about 1 second. In some examples, the duration of the time interval between time points may be at least about 1 minute. In other examples, the duration of the time interval between time points may be at least about 1 hour. In other examples, the duration of the time interval may be at least 1 day. In other examples, the duration of the time interval may be at least 5 days. In still other examples, the duration of the time interval may be about 0.01, 0.1, 1, 2, 3, 4, 5, 10, 20, 30, 40, 50, or 60 minutes or about 1, 2, 3, 4, 5, 6, 7, 8, 9, 10, 12, 15, or 20 hours, or 1, 1.2, 1.4, 1.6, 1.8, 2.0, 2.2, 2.4, 2.6, 2.8, 3.0, 3.2, 3.4, 3.6, 3.8, 4.0, 4.2, 4.4, 4.6, 4.8, 5.0, 6.0, 7.0, 8.0, 9.0, 10, 12, 14, 16, 18, or 20 days.

An enumeration may be determined once for a reaction mixture at a given time point or may be determined using replicate enumerations obtained from aliquots of the reaction mixture. In cases, where replicate enumerations are used, an average enumeration may be calculated for a time point. Moreover, enumerations may be completed for identical, replicate reaction mixtures and subsequently reported collectively as an average.

The number of microbial taxa or taxon-identifying chemical species that are enumerated may vary. Number variance may vary, for example, due to the number of species or taxon-identifying chemical species that are present in a microbial community of interest. Some microbial communities of interest may possess greater numbers of relevant taxa or taxon-identifying chemical species that are present. In some examples, the number of microbial taxa or taxon-identifying chemical species that are enumerated is from 1 microbial taxa or taxon-identifying chemical species to 1,000,000 microbial taxa or taxon-identifying chemical species. In other examples, the number of microbial taxa or taxon-identifying chemical species that are enumerated is from 1 microbial taxa or taxon-identifying chemical species to 100,000 microbial taxa or taxon-identifying chemical species. In other examples, the number of microbial taxa or taxon-identifying chemical species that are enumerated is from 1 microbial taxa or taxon-identifying chemical species to 10,000 microbial taxa or taxon-identifying chemical species. In other examples, the number of microbial taxa or taxon-identifying chemical species that are enumerated is from 1 microbial taxa or taxon-identifying chemical species to 100 microbial taxa or taxon-identifying chemical species. In other examples, a single microbial taxon or taxon-identifying chemical species is enumerated.

In some examples, the number of microbial taxa or taxon-identifying chemical species that are enumerated is at least 1 microbial taxon or taxon-identifying chemical species. In other examples, the number of microbial taxa or taxon-identifying chemical species that are enumerated at least 100 microbial taxa or taxon-identifying chemical species. In other examples, the number of microbial taxa or taxon-identifying chemical species that are enumerated is at least 1,000 microbial taxa or taxon-identifying chemical species. In other examples, the number of microbial taxa or taxon-identifying chemical species that are enumerated is at least 10,000 microbial taxa or taxon-identifying chemical species. In other examples, the number of microbial taxa or taxon-identifying chemical species that are enumerated is at least 100,000 microbial taxa or taxon-identifying chemical species. In still other examples, the number of microbial taxa or taxon-identifying chemical species enumerated is at least 1, 10, 100, 1000, 10,000, 100,000, or 1,000,000 microbial taxa or taxon-identifying chemical species.

Moreover, all possible microbial taxa within a given taxonomic classification scheme or all known taxon-identifying chemical species may be enumerated. Alternatively, one or more particular subsets of all possible microbial taxa within a given taxonomic classification scheme or taxon-identifying chemical species may be enumerated.

The particular microbial taxa and/or taxon-identifying chemical species that are enumerated may be derived from microbial taxa determined from experiments. Such experiments may include experiments that have identified certain microbial taxa that are important to a specific disease condition or general health of a subject.

Completed enumerations may be manipulated in order to better interpret the results of an assay and/or compare the results of an assay with that of another. Numerical manipulations may be made, for example, using an algorithm that may be useful in interpreting the results of an assay. Such numerical manipulations may be made for all enumerated microbial taxa and/or taxon-identifying chemical species, a subset of all enumerated microbial taxa and/or taxon-identifying chemical species, or a single enumerated microbial taxon and/or taxon-identifying chemical species. An example algorithm is a difference algorithm wherein an enumeration completed after adding an agent to a reaction mixture is subtracted from an enumeration completed prior to adding the agent to the reaction mixture. The magnitude of the calculated difference may quantitatively indicate the degree to which the agent affects the respective microbial taxon of interest in the subject of interest.

In another example, an algorithm may be used to compare an enumeration to one or more reference enumerations. For example, a first sample may be obtained from a subject afflicted with a condition and contacted with an agent of interest in a first reaction mixture. Microbial taxa or taxon-identifying chemical species of interest in the first reaction mixture are enumerated after the agent is added to the first reaction mixture. A second sample may be obtained from a normal (i.e., healthy) subject, prepared in a second reaction mixture, with no agent added to the second reaction mixture.

The appropriate microbial taxa and/or taxon-identifying chemical species of interest enumerated in the first reaction mixture may then also be enumerated in the second reaction mixture. An example algorithm whereby the two reaction mixtures are compared includes taking the difference between the enumerations for the two reaction mixtures. The magnitude of the calculated difference may quantitatively indicate the degree to which an agent drives the levels and/or function of the microbial taxon of interest in the afflicted subject toward the levels and/or function of the microbial taxon observed in the normal subject.

Enumerations of each microbial taxa and/or taxon-identifying chemical species may be collected and used for completing a principal component analysis (PCoA). A PCoA analysis may be used to generate UniFrac distances between different treatment groups (e.g., samples obtained from an afflicted subject and contacted with an agent vs. samples obtained from a normal subject and not contacted with the agent). A UniFrac distance generally refers to a metric that is a distance measure between organismal communities using phylogenetic information. Such a metric may be useful in quantitatively describing the degree of similarity/dissimilarity between different treatment groups. Such measures of similarity/dissimilarity may be used to identify shifts in microbiomes.

Dissimilarity measures are generally with respect to two samples with a result that is a matrix of all pair-wise sample dissimilarities. This matrix may be more manageable for creating an overview because statistical techniques such as hierarchical clustering or ordinations can be employed to visualize the important patterns of variation across samples. The particular dissimilarity measures used may depend on assessment of changes in the abundances of microbes, the incidence (presence/absence) of microbes, whether to consider information on phylogenetic relationships between microbial taxa or to treat the microbial taxa as unrelated bins, and combinations thereof.

In considering a pair of samples, the Sørensen index may be sensitive to overlap. Specifically, the Sorensen index is the ratio of the number of microbial taxa or metabolites simultaneously detected in both samples compared to the sum of the microbial taxa or metabolites in both samples. Moreover, the Sorensen index provides insights but stops short of using the phylogenetic relationships that exist among all bacteria, something that is offered by unweighted Unifrac calculations. Since bacteria are taxonomically classified into phyla, classes, orders, families, genera and species, differences between samples can incorporate the magnitude of the genetic difference between the microbes present in each sample. Using Unifrac, if two species are in the same family the pair-wise dissimilarity may be less than if those two species were in distinct families. In cases where phylogenetic relationships between taxa are known, unweighed Unifrac dissimilarity may be preferable over Sorensen dissimilarity.

The basic sample-to-sample dissimilarity measurement using the abundance of each microbial taxa is carried out by the Bray-Curtis index. The Bray-Curtis function performs a pair-wise normalization by dividing the sum of differences by the sum of all abundances which is helpful when abundance metrics across samples are imperfectly scaled. The index is sensitive to the difference in abundance observed between the same taxa across pairs of samples. To integrate both the relationships between taxa and the abundance fluctuations of those taxa across samples, the weighted Unifrac measure may be used. Unifrac can aid in resolving subtle variations in composition between microbial communities.

Combination with Additional Assays

Assays described herein may be used in combination with additional assays depending on need. In some instances, results from an assay described herein may be used execute an additional assay or results from an additional assay may be used to execute an assay described herein. Non-limiting examples of additional assays that may used with an assay described herein include a blood assay, a urine assay, a fecal assay, a cerebrospinal fluid assay, a saliva assay, a sputum assay, an assay performed on a biopsy, an assay performed on part of the reproductive system, a cardiovascular assay, a respiratory assay, a cognitive assay, a reproductive assay, a liver function assay, a kidney function assay, a thyroid assay, a locomotor assay, an ocular assay, and combinations thereof.

Functionality Assays

In addition to enumerating the abundance of one or more microbial taxa or taxon-identifying chemical species, functionality assays may be used to determine the effects of an agent on a sample, including the effects of microbial agents (e.g., bacterial agents) on tissue or cellular samples obtained from a subject. The tissue or cellular samples may be representative of a particular anatomical region of the subject (e.g., fecal samples may be representative of the gut). In such cases, a method may comprise the steps of: (a) obtaining a sample (e.g., a tissue sample or cell sample) from a first subject; (b) contacting the sample with an agent in a reaction mixture; and (c) evaluating the functionality of the sample upon contact with the agent. When contacting an agent with a sample, any suitable incubation condition(s) may be used, including incubation conditions (e.g., incubation temperature, incubation humidity, atmospheric oxygen content, atmospheric carbon dioxide content, atmospheric nitrogen content, incubation time, etc.) described elsewhere herein.

For example, an agent in a functionality assay may comprise one or more microbes, such as, for example bacteria. The microbes may be obtained from any sample type or sample source described herein, such as, for example, feces, cecal contents, or other matter (including others described herein) produced by a living organism. In some cases, the microbes may be microbes obtained from samples already contacted with another agent.

In cases where microbes are obtained from solid matter (e.g., feces or cecal contents) produced by a living organism, the solid matter may be obtained from the living organism, homogenized if necessary (e.g., in the case of tissue samples), and used as in agent. In some cases, solid matter may be optionally homogenized and slurried. The slurry may be incubated at appropriate conditions (e.g., incubation temperature, incubation time, incubation atmosphere, etc. as described elsewhere herein) in order to propagate microbes in the slurry. The solid content of the slurry may then be separated (e.g., via centrifugation) from the liquid component and the supernatant comprising microbes from the matter obtained from the living organism used as an agent. In some cases, the solid content of the slurry may be used as an agent.

The agent may then be contacted with a sample of interest (e.g., cell sample (e.g., HT29, HT29 MTX or CaCo2 cells), cells grown from tissue samples, tissue samples, organotypic cultures derived from a tissue (e.g., colon), etc.) and incubated with the agent at desired conditions (e.g., e.g., incubation temperature, incubation time, incubation atmosphere, etc. as described elsewhere herein). In some cases, antibiotics may be added to reaction mixtures in order to determine the effect of diminished microbial functionality in the assay.

After contact with the sample of interest, the functionality of the sample may be assessed to determine the effects of the agent on the sample. Functionality may be assessed, for example, via a barrier function assay (including assays where the permeation of high molecular weight, fluorescent labels, such as FITC-Dextran, are measured), a cell viability assay (e.g., via Live/Dead™ staining or DAPI staining), a cytokine production assay (including where cytokines are measured via an ELISA assay), and/or an immune response assay.

Results of a functionality assay may be used for any suitable purpose, including the various uses for the results of assays described elsewhere herein. In some cases, a sample in a functionality assay can serve as 'reporter' host to determine the effects of microbial agents (e.g., bacteria) on cellular functions. Where microbial agents (e.g., bacteria) are obtained from the products of another assay, the effects of the microbial agents in a functionality assay may be used to assess the functionality of the microbial agents. For example, in cases where a first agent is contacted with a first sample in a first assay in a reaction mixture, the microbes (e.g., bacteria) in the reaction mixture can then be used as second agents in a functionality assay. The observed effects of the microbes in the functionality assay may be used to assess the functionality of the microbes obtained after contacting the first agent with the first sample in the first assay.

Methods for Utilizing the Results of a MESA Assay

This disclosure provides methods for interpreting and/or utilizing the results of an assay described herein. The in vitro nature of assays may be especially beneficial to probing the effects of an agent on microbial taxa of interest, without the potential for agent toxicity when investigated in vivo. In one aspect, the results of assays may be used to make inferences about the effects of an agent for a population of subjects. In another aspect, assays may aid in decision-making regarding the utility of an agent in a variety of applications that include, for example, health care and health safety decision-making. This disclosure also provides methods for counseling such that healthcare and health safety decision-making may be disseminated to subjects in want or need.

Reference Enumerations

In general, an enumeration of an assay (referred to herein as a "test enumeration") or any numerical manipulation of the enumeration, may be considered in isolation or may be considered with respect to one or more reference enumerations or numerical manipulations of a reference enumeration. In general, a reference enumeration may be any enumeration used as a control for a test enumeration. A reference enumeration, for example, may be an enumeration generated for a sample(s) (or reaction mixture comprising a sample) obtained from a subject(s) of different type than that of the test enumeration; may be an enumeration generated for samples obtained from a subject not contacted with an agent of interest; may be an enumeration generated for a sample contacted with an agent different than that of interest; and combinations thereof.

In one example, a test enumeration is completed for a sample obtained from a subject afflicted with a particular condition and contacted with an agent of interest. The same enumeration is also completed for a sample obtained from a normal (i.e., healthy) subject and not contacted with the agent, and the enumerations serves as a reference enumeration. The reference enumeration may be used, with or without further data analysis, for example, to determine whether or not the agent can drive the level and/or function of the enumerated microbial taxa in the afflicted subject toward the level and/or function of the enumerated microbial taxa in the normal subject.

In another example, a first and second sample is obtained from a subject afflicted with a condition. A test enumeration is completed for the first sample, which is contacted with an agent of interest. The same enumeration is completed for the second sample, which is not contacted with the agent of interest, and the enumeration serves as a reference enumeration. The reference enumeration may be used, with or without further data analysis, for example, to determine whether or not the agent affects the level and/or function of the enumerated microbial taxa in the afflicted subject.

In yet another example, two samples are obtained from a subject afflicted with a condition and two samples are obtained from a normal (i.e., healthy) subject. One sample from each subject is contacted with an agent of interest and two respective test enumerations are generated. The remaining two samples are not contacted with the agent of interest and each serve as a reference enumeration for each test enumeration for the respective subject. The reference enumeration for each subject may be used, with or without further data analysis, for example, to determine whether or not the agent affects the level and/or function of the enumerated microbial taxa in each subject. Moreover, the comparisons of each reference enumeration to its respective test enumeration may be used to determine whether or not the agent affects the level and/or function of the enumerated microbial taxa in the subject afflicted with the condition differently than it does in the normal subject.

A reference enumeration may represent a threshold in a given application. A threshold value generally should be considered with respect to the particular microbial taxa evaluated and/or any other available information (e.g., additional assays). In some examples, higher-than-threshold values for a test enumeration may be desired. In other examples, lower-than-threshold values for a test enumeration may be desired.

Estimating Effects of an Agent on Subjects of a Subject Population

An assay described herein may be used to estimate the effects of an agent on subjects of a population. For example, assays may be completed with respect to an agent of interest for a collection of samples obtained from various subjects of a group selected to represent a population. The collection of results from the assays may then be used, with or without further analysis, to generalize the effects of the agent on any subject of the population. For example, assays with respect to an agent of interest may be completed for samples obtained from 100 subjects all afflicted with a condition. The set of assay results may used, with or without further analysis, to generalize the effect of the agent on the appropriate microbial taxa in any subjects afflicted with the condition.

A population may be, for example, subjects all afflicted with a condition, subjects not afflicted with a condition, subjects all of the same race, subjects all of the same ethnicity, subjects all of the same gender, subjects all of a particular age or age group, subjects all of a particular phenotype (e.g., subjects that all have red hair, subjects that all have blue eyes, subjects all of a certain height, etc.), subjects all of a particular level in a phylogenic classification scheme, and combinations thereof. Indeed, a population may be the totality of subjects in a group identified by a unifying feature. Moreover, a population may be divided into a plurality of sub-populations based on an additional unifying feature (e.g., subjects that all have red hair and blue eyes).

The number of subjects in a group selected to represent a population may vary. In some examples, the number of test subjects in a group selected to represent a population is 1 subject. In some examples, the number of test subjects in a group selected to represent a population is at least 2 subjects. In other examples, the number of test subjects in a group selected to represent a population is at least 100 subjects. In other examples, the number of test subjects in group selected to represent a population is at least 1000 subjects. In other examples, the number of test subjects in a group selected to represent a population is at least 10000 subjects. In still other examples, the number of test subjects in a group selected to represent a population is at least 2, 3, 4, 5, 6, 7, 8, 9, 10, 20, 30, 40, 50, 60, 70, 80, 90, 100, 150, 200, 250, 300, 350, 400, 450, 500, 550, 600, 650, 700, 750, 800, 850, 900, 950, 1000, 2000, 3000, 4000, 5000, 10000 or more subjects.

In some examples, the number of test subjects in a group selected to represent a population is from 2 subjects to 10000 subjects. In other examples, the number of test subjects in a group selected to represent a population is from 2 subjects to 1000 subjects. In other examples, the number of test subjects in group selected to represent a population is from 2 subjects to 100 subjects. In other examples, the number of test subjects in a group selected to represent a population is from 2 subjects to 10 subjects.

In some cases, an assay completed for one type of subject or population may be used to estimate the effects of an agent on one or more different types of subjects or population. For example, an assay for a subject of one species of a living organism (i.e., one type of subject) may be used to estimate the effects of the agent in a subject of another species of a living organism (i.e., another type of subject). Analogously, assays completed to estimate the effects of an agent in the population of subjects of one species of living organism may be used to estimate the effects of the agent in the population of subjects of another species of living organism.

Indeed, assays completed using a subject(s) of any of the species described herein may be used to estimate, with or without further analysis, the effects of an agent on a subject (s) of any other species described herein. For example, an assay completed for a species of a common laboratory animal such as a mouse or rat may be used to estimate the effects of an agent on a human. Non-limiting examples of additional species pairs include: a human and a species of mouse; a human and a species of rat; a human and a species of dog; a human and a species of monkey; a human and a species of rabbit; a human and a species of pig; a dog and a species of mouse; a dog and a species of rat; a cat and a species of mouse; a cat and a species of rat.

Healthcare and Health-Safety Decision-Making

An assay described herein may aid in healthcare and/or health-safety related decision-making with respect to an agent or a combination of agents. Samples may be obtained from a subject or a group of subjects, assayed with an agent or a combination of agents desired for healthcare-related use, and the results of an assay(s) used in making decisions regarding the acceptability of the agent or combination of agents and/or the use of such entities in the subject or group of subjects studied. Decisions made for a group of subjects may be extended to a population for which the subjects of the group are selected to represent. Moreover, decisions made for a subject, group of subjects, or population may be extended to one or more different types of subject, group of subjects, or population.

Healthcare decisions may include, for example, deciding upon the utility (e.g., efficacy, safety, etc.) of an agent or combination of agents in a subject or population; and selection of subjects for particular use(s) of an agent or combination of agents. More specific examples of healthcare related decisions include: determining the utility of an agent or combination of agents to be used as a drug(s); selecting subjects to use a drug or combination of drugs; determining the utility of an agent or combination of agents to be used as a supplement(s); selecting subjects to use a supplement or combination of supplements; determining the utility of a food or combination of foods (e.g., a diet); selecting subjects for a particular food or diet; determining the utility of a beauty product or a combination of beauty products; selecting subjects to use a beauty care product or combination of beauty care products; determining the utility of a personal hygiene product or combination of personal hygiene products; selecting subjects to use a personal hygiene product or combination of personal hygiene products; determining the propensity of an agent to cause a condition in a subject or population where the condition is associated with an undesirable shift in local microbial populations caused by the agent; determining the safety of a new chemical; determining the safety of a hazardous material, and combinations thereof.

Decision-Making with Respect to a Drug or Other Consumer Healthcare Product

An assay described herein may aid in determining the utility of an agent to be used as a drug or a plurality of agents to be used as a combination of drugs. Determining the utility of an agent to be used as a drug or a combination of agents to be used as a combination of drugs may include evaluating the potential therapeutic efficacy and/or safety of the agent or combination of agents. Such determinations may be made, for example, with respect to the capability of an agent or combination of agents to cause a desirable change in the levels and/or function of one or more microbial taxa in a subject(s) from which a sample(s) is obtained. In cases where a condition is thought to be linked to a microbiome, a desirable change with respect to a potential drug(s) generally refers to a shift in the levels and/or function of microbial taxa associated with a condition toward levels and/or function associated with a healthy state all while minimizing any unwanted and/or harmful changes (i.e., side-effects) to other microbial taxa. In cases where a condition is not thought to be linked to a microbiome, a desirable change with respect to a potential drug(s) generally refers to minimized disruption of a microbiome. In some cases, two or more agents may be considered in combination therapy such that one or more of the agents aids in ameliorating the deleterious effects of any others.

In some cases, it may be determined, based upon one or more assays described herein, that an agent or combination of agents may not alter or may unfavorably alter the levels and/or function of one or more microbial taxa to the extent that the agent or combination of agents is potentially inefficacious and/or unsafe (i.e. toxic). In other cases, it may be determined, based upon one or more assays described herein, that an agent or combination of agents favorably alters the levels and/or function of one or more microbial taxa to the extent that the agent or combination of agents is potentially efficacious and/or safe. In still other cases, it may be determined that assays or investigations in addition to one or more assays described herein may be required to determine the utility of an agent or combination of agents as a drug(s).

An agent studied for use as a drug may be any chemical species, including any example agent described herein. Moreover, an assay may be completed post-approval of a drug such that an already approved drug (prescription or over-the-counter) is further evaluated for utility, including efficacy with respect to an indication not yet approved for treatment with the drug and/or safety with respect to a microbiome. Analogously, previously approved drugs that have been withdrawn from the market may be further evaluated for utility using an assay described herein. Moreover, an agent that is currently in pre-clinical or clinical development, or an agent that is currently available but has not yet been considered for use as a drug may also be evaluated for utility as a drug.

In particular, antibiotic therapies may be of especially important interest as they are generally designed to stunt growth the growth of (e.g., bacteriostatic agents) and/or kill (e.g., bactericidal agents) bacteria. Unfortunately, an antibiotic designed to reduce the levels and/or function of harmful bacteria may also reduce the levels and/or function of bacterial populations considered to be beneficial. Thus, assays may be especially useful in decision-making with respect to the utility of an antibiotic or of an antibiotic used in combination with other drugs or agents.

An assay described herein may aid in utility determinations for agents implicated as potential or already-available other consumer healthcare products such as supplements, beauty products, and/or personal hygiene products in analogous fashion to that described above for drugs. Again, any chemical species may be considered for use as any of these types of agents. Assays may aid in making utility determinations when an agent or agents of any of these types is considered with respect to the use of a drug. For example, an assay described herein may be used to determine the utility of one or more supplements and/or drugs when the supplement(s) and drug(s) are used in combination.

An assay described herein may aid in determining the utility of an agent or a combination of agents during development and/or regulatory agency (e.g., the U.S. Food and Drug Administration (FDA)) evaluations of an agent. For example, during pre-clinical development and/or clinical trials of a drug, an assay described herein may be used by a drug research and development organization to make decisions regarding initiating or continuing development of a particular agent. In one example, it may be determined that a set of agents (novel, non-novel, or a combination thereof) may be useful as drugs to treat one or more conditions. At any point during development, an assay employing one or more agents of the set may be used to, for example, select agents from the set for initiating or continuing pre-clinical development; select agents from the set for initiating or continuing clinical trials; and/or determining the mechanism of action of one or more agents of the set. The use of high-throughput assays described herein may be especially useful in screening large groups of potential drugs.

Moreover, at any point during the development process of an agent, an assay described herein may be used (by either or both of a drug development organization or regulatory agency) to assess the acceptability of an agent to receive approval (e.g., for prescription use or for over-the-counter use in the case of a drug) for use in a population of subjects (e.g., for use in humans) and/or the dosage at which an agent or combination of agents can be safely and/or effectively administered. Additionally, an assay described herein may be used post-approval of an agent such that a regulatory agency makes a decision as to whether or not the approved agent should remain on the market and/or whether changes to an approved/recommended dosage should be made.

An assay described herein may be used to aid in selecting a subject for use of a drug, combination of drugs, other consumer healthcare product, combination of other consumer healthcare products, and combinations thereof. For example, a subject afflicted with a condition may be in want or need of a drug approved and available for the treatment of the condition. A sample may be obtained from the subject and assayed with respect to the drug using methods described herein. The results of the assay, with respect to drug efficacy and/or safety, may then be used to determine whether or not the subject may benefit from treatment with the drug and, thus, whether or not the subject should commence using the drug.

An assay described herein may be used to aid in selecting a population for use of a drug, combination of drugs, other consumer healthcare product, combination of other consumer healthcare products, and combinations thereof. For example, assays may be completed for samples obtained from a group of subjects selected to represent a population with respect to a drug or combination of drugs. The results of the assays may be used to aid in making decisions with respect to use of the drug or combination of drugs in the population. In one example, it may be observed, after completing an assay described herein, that key microbial taxa respond favorably in a group of human subjects selected for a clinical trial of an agent. Such an observation may be used in deciding whether humans in general. In another example, it may be observed that, after completing an assay described herein, key microbial taxa respond unfavorably to a drug in a group of women selected to represent the population of women, to the extent that the drug may not be useful in women. The results of the assay may then be used in deciding whether or not women in general should use the drug.

Decision-Making with Respect to Foods and Diets

An assay described herein may aid in determining a preference for a food (which may be a beverage) or a combination of foods, including a diet. The preference for a food or diet may be based upon a number of factors that include, for example, the safety of a food or diet and/or the propensity of a food or diet to cause a change in one or more microbial populations of a host subject that ingests the food or diet. Non-limiting examples of diets include a South Beach Diet, a Dukin diet, a Stillman diet, an Atkins Diet, a gluten-free diet, a ketogenic diet, a low-residue diet, a liquid diet, a vegetarian diet, a low-calorie diet (e.g., Weight Watchers™, Jenny Craig™ Nutrisystems™), a low-fat diet, a low-carbohydrate diet, a low-protein diet, a low-monosodium glutamate (MSG) diet, a detox diet, an elimination diet, a specific carbohydrate diet, a diabetic diet, a dietary approaches to stop hypertension diet (DASH) diet, a best bet diet, an organic diet, and combinations thereof.

Assays may be completed for virtually any type of food and/or diet. In some cases, determinations are made between the same type of food that is obtained from a plurality of sources (e.g., beef obtained from grass-fed livestock vs. beef obtained from livestock fed on a concentrated diet of grain, soy, corn and other supplements such as steroids and antibiotics). Foods or diets may include, for example, already available foods or diets that are available on the market, foods or diets that have been withdrawn for the market, foods or diets that are currently in development, foods or diets that have yet-to-be-developed; and agents that are currently available but have not yet been considered for use as foods or as foods in a diet. Moreover, an assay described herein may be used to make decisions regarding a food or combination of foods in a subject or group of subjects also treated with a drug or other agent.

The results of an assay evaluating a food or combination of foods may be used in analogous fashion to that described above for drugs and other consumer healthcare products, such that the results are used to decide whether a food or combination of foods should be consumed. Moreover, selection of a subject and/or population for a particular food or diet may also be completed analogous to subject/population selection described above for drugs and other consumer healthcare products.

Decision-Making with Respect to the Propensity to Cause a Condition

An assay described herein may aid in determining the propensity of an agent to cause one or more conditions. Indeed, an in vitro assay described herein may be of particular value in assessing any deleterious effects of an agent in a subject prior to actually administering the agent to the subject in vivo. A number of conditions are known to be associated with the presence and composition of particular microbial communities. For example, the intestinal gut microbiota provides many crucial functions to its host, including contribution to digestion, the development of the immune system, and resistance to pathogenic colonization. Even a slight fluctuation in the symbiotic balance may be deleterious to the host, leading to pathological conditions such as, for example, *Clostridium difficile* infection or inflammatory bowel disease (IBD). As a result, it is important to monitor the effects of agents on microbiota as they may cause conditions to arise in an administered host. Other non-limiting examples of conditions that may be caused by an agent include a condition of the gut, Crohn's Disease (CD), irritable bowel syndrome (IBS), stomach ulcers, colitis, neonatal necrotizing enterocolitis, or gastroesophageal reflux disease (GERD), cystic fibrosis, chronic obstructive pulmonary disease, rhinitis, atopy, asthma, acne, a food allergy, obesity, periodontal disease, diarrhea, constipation, functional bloating, gastritis, lactose intolerance, visceral hyperalgesia, colic, pouchitis, diverticulitis, allergies, asthma, sinusitis, chronic obstructive pulmonary disorder (COPD), depression, attention deficit hyperactivity disorder (ADHD), autism, Alzheimers, migraines, multiple sclerosis (MS), Lupus, arthritis, Type 2 diabetes, obesity, non alcoholic steato hepatitis (NASH), non alcoholic fatty liver disease (NAFLD), risk of infarction/cardiovascular risk, heart failure, cancer, dental caries, gingivitis, oral cancer, oral mucositis, bacterial vaginosis, fertility, sinusitis, allergies, cystic fibrosis, lung cancer, psoriasis, atopic dermatis, methicillin-resistant *staphylococcus aureus* (MRSA), colorectal cancer, acne, vancomycin resistant *enterococcus*, and combinations thereof.

The capability of an agent or combination of agents to cause a condition can be evaluated using an assay described herein for virtually any agent, including any of the example agents described herein. In cases where disease states are already present, the propensity of an agent to further exacerbate the symptoms and/or progression of a condition and/or cause a form of toxicity may also be evaluated.

Lists of Recommended Agents

An assay described herein may be used to aid in generating a list of preferred or recommended agents. A list may include, for example, the specific agents recommended and appropriate use regimens (e.g., dose, dosing frequency, exposure limits, etc.) and may also include agents not-recommended with or without a rationale for withholding recommendation. Lists may rank agents, categorize agents (e.g., by condition, drug-class, etc.), or may rank and categorize agents. Lists may be compiled such that recommended (or non-recommended) agents or combinations of agents are those that have assay results at or above (or below) a given threshold. Such a threshold may be determined, for example, from one or more reference enumerations.

Counseling

The results of an assay described herein may be used to provide counseling services to those in want or need. In general, counseling generally comprises the steps of: (a) obtaining a sample from a first subject; (b) contacting said sample with an agent in a reaction mixture; (c) obtaining an enumeration of the abundance of one or more microbial taxa or taxon-identifying chemical species in said reaction mixture after contacting the sample with the agent; and (d) providing counseling regarding the exposure of said agent to the first subject and/or one or more additional subjects using the enumeration or a numerical manipulation of the enumeration.

An additional subject may be of the same subject type as the first subject or may be of a different subject type. For example, counseling to a human subject may be provided based off of enumerations completed for a sample(s) obtained from another human subject. In another example, counseling to a human subject may be provided based off of enumerations completed for a sample(s) obtained from a common laboratory animal, such as, for example, a mouse or rat. In another example, counseling may be provided with respect to one species of dog using enumerations for a sample(s) obtained from subjects of another species of dog.

In some cases, enumerations of microbial taxa or taxon-identifying chemical species or numerical manipulations of such enumerations may be provided in a database and stored, for example, in a computer. The database may be accessed in order to provide counseling to subjects in want or need.

Counseling services may include deciding on a treatment regimen for a subject with a condition. In some examples, counseling may include deciding between two or more drugs available for treatment of the condition and/or the dosage of the chosen drug(s) that should be used for treatment.

In some examples, counseling may include advice for pursuing fecal transplants. A sample may be obtained from a subject of want or need of fecal transplant advice. The sample may be assayed with an aliquot of donor fecal matter (which may be used in a transplant) and the relevant microbial taxa or taxon-identifying chemical species enumerated. Obtained enumerations or numerical manipulations of such enumerations may then be used to counsel the subject on the utility of pursuing a fecal transplant.

Counseling services may include the communication of a variety of pieces of information with respect to use of an agent, including recommendations. Non-limiting examples of such information includes information regarding the results of an assay for samples obtained from the subject seeking counseling, the results of an assay for samples obtained from a subject different than the subject seeking counseling, the results of an assay for samples obtained from a group of subjects selected to represent a population, information regarding the safety of an agent, information regarding the efficacy of an agent, information regarding the safety of an agent when administered with one or more different agents, information regarding the efficacy of an agent when administered with one or more different agents, a recommendation to use or continue to use an agent or combination of agents, a recommendation to not use or discontinue use of an agent or combination of agents, providing a ranked list of possible agents or combination of agents for use or continued use, recommendations for the addition of one or more different agents to a regimen comprising an agent or combination of agents, recommendations for monitoring use of an agent over time, recommendations for doses of an agent, recommendations regarding the propensity of an agent to cause a condition, or combinations thereof.

Counseling may be provided, for example, by a person, a company, a representative of a health-care organization (e.g., a hospital, hospital system, medical group, etc.), a health-care organization, a government official, a government office, a consultant, via a subscription service, via an online vendor, via a printed publication, via live audio or an audio recording, via postal mail, via email, via telephone, via the internet, and combinations thereof. Counseling may be provided, for example, to a person, a company, a representative of a health-care organization, a consultant, a government official, a government office, and combinations thereof.

Counseling may be provided on demand, in a single counseling session, or in multiple counseling sessions. For example, on demand counseling may be necessary where immediate intervention is necessary to treat a condition.

Counseling may be provided for a pet or other subject under to the ownership and/or care of another subject.

Counseling may be completed by or provided to a company or organization. For example, an assay may be completed by an organization (e.g., a business, a company, a special interest group, an educational institution, etc.) and the results used to counsel another subject, group of subjects, or organization.

Counseling may be provided by a public health organization. For example, the results of assays completed for a group of subjects selected to represent a population may be disseminated to members of the population via government-sponsored advertisements.

Counseling services may also include the generation of one or more reports. Such reports may be given to a subject in want or need in hard-copy form or may be transmitted electronically, such as by email. Reports may include raw data obtained from detecting microbial taxa or taxon-identifying chemical species, enumerating microbial taxa or relating chemical species, any numerical manipulations of an enumeration, changes of abundance of one or more microbial taxa enumerated after contact with an agent, an algorithm used to enumerate microbial taxa, an algorithm used to numerically manipulate an enumeration, and combinations thereof. A report may also include summaries of provided counseling, including any of the various example pieces of information described above.

Systems to Implement Methods

The disclosure provides specialized computer systems that are configured to implement methods described herein, including the execution of any part of an assay, enumerating microbial taxa and/or taxon-identifying chemical species, further analysis of such enumerations, and/or aiding in providing counseling services. Specialized computer systems are generally capable of any of the following: (a) controlling any equipment used to execute an assay; (b) accepting raw data obtained from executing an assay; (c) pre-processing raw data such that it is acceptable for entry into algorithms used to enumerate microbial taxa and/or taxon-identifying chemical species; (d) numerical manipulation of an enumeration (e); interpreting, in whole or part, the results of an assay; (f) storing any assay protocol, enumeration, numerical manipulation of an enumeration, and/or interpretation of the results of an assay; (g) generating and storing a report; and (h) aiding in providing counseling. The system may include a computer server ("server") that is programmed to implement the methods described herein. FIG. 1 depicts a system 100 adapted to enable a user to detect, analyze, and process raw data obtained an assay. The system 100 includes a central computer server 101 that is programmed to implement exemplary methods described herein. The server 101 includes a central processing unit (CPU, also "processor") 105 which can be a single core processor, a multi core processor, or plurality of processors for parallel processing. The server 101 also includes memory 110 (e.g. random access memory, read-only memory, flash memory); electronic storage unit 115 (e.g. hard disk); communications interface 120 (e.g. network adaptor) for communicating with one or more other systems; and peripheral devices 125 which may include cache, other memory, data storage, and/or electronic display adaptors. The memory 110, storage unit 115, interface 120, and peripheral devices 125 are in communication with the processor 105 through a communications bus (solid lines), such as a motherboard. The storage unit 115 can be a data storage unit for storing data. The server 101 may be operatively coupled to a computer network ("network") 130 with the aid of the communications interface 120. The network 130 can be the Internet, an intranet and/or an extranet, an intranet and/or extranet that is in communication with the Internet, a telecommunication or data network. The network 130 in some cases, with the aid of the server 101, can implement a peer-to-peer network, which may enable devices coupled to the server 101 to behave as a client or a server.

The storage unit 115 can store files, such as raw data files from assays, assay protocols, databases of reference enumerations, nucleic acid sequences used to enumerate microbial taxa, databases of microbial taxa classification schemes, instructions to execute numerical manipulations, enumerations, numerical manipulations of enumerations, interpretations (e.g., reports, input notes, etc.) of assay results, or any aspect of data associated with the executing methods described herein.

The server can communicate with one or more remote computer systems through the network 130. The one or more remote computer systems may be, for example, personal computers, laptops, tablets, telephones, Smart phones, or personal digital assistants. Moreover, system 100 may be capable of accepting instructions over network 130 from one or more remote computer systems such that its data is accessed (either by the remote computer systems or system 100). Alternatively, system 100 is capable of accepting data stored, analyzed, and/or interpreted on a remote system that is transmitted to system 100 over network 130. Moreover, system 100 is also capable of transmitting data stored, analyzed, and/or interpreted by system 100 to one or more remote computers over network 130.

In some situations the system 100 includes a single server 101. In other situations, the system includes multiple servers in communication with one another through an intranet, extranet and/or the Internet.

The server 101 can be adapted to store raw data files from assays, assay protocols, databases of reference enumerations, nucleic acid sequences used to enumerate microbial taxa, databases of microbial taxa classification schemes, instructions to execute numerical manipulations, enumerations, numerical manipulations of enumerations, interpretations (e.g., reports, input notes, etc.) of assay results, or any aspect of data associated with the executing methods described herein. Such information can be stored on the storage unit 115 or the server 101 and such data can be transmitted through a network, such as network 130.

Methods as described herein can be implemented by way of machine (or computer processor) executable code (or software) stored on an electronic storage location of the server 101, such as, for example, on the memory 110, or electronic storage unit 115. During use, the code can be executed by the processor 105. In some cases, the code can be retrieved from the storage unit 115 and stored on the memory 110 for ready access by the processor 105. In some situations, the electronic storage unit 115 can be precluded, and machine-executable instructions are stored on memory 110. Alternatively, the code can be executed on a second computer system 140.

Aspects of the systems and methods provided herein, such as the server 101, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such memory (e.g. read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical, and electromagnetic waves, such as used across physical interfaces between local devices, through wired and optical landline networks and over various air-links. The physical elements that carry such waves, such as wired or wireless likes, optical links, or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, tangible storage medium, a carrier wave medium, or physical transmission medium. Non-volatile storage media can include, for example, optical or magnetic disks, such as any of the storage devices in any computer(s) or the like, such may be used to implement the system. Tangible transmission media can include: coaxial cables, copper wires, and fiber optics (including the wires that comprise a bus within a computer system). Carrier-wave transmission media may take the form of electric or electromagnetic signals, or acoustic or light waves such as those generated during radio frequency (RF) and infrared (IR) data communications. Common forms of computer-readable media therefore include, for example: a floppy disk, a flexible disk, hard disk, magnetic tape, any other magnetic medium, a CD-ROM, DVD, DVD-ROM, any other optical medium, punch cards, paper tame, any other physical storage medium with patterns of holes, a RAM, a ROM, a PROM and EPROM, a FLASH-EPROM, any other memory chip or cartridge, a carrier wave transporting data or instructions, cables, or links transporting such carrier wave, or any other medium from which a computer may read programming code and/or data. Many of these forms of computer readable media may be involved in carrying one or more sequences of one or more instructions to a processor for execution.

Interpretation of the results of an assay, such as the generation of a report, may be presented to a user with the aid of a user interface, such as a graphical user interface (GUI). Moreover, systems may be coupled to a printer device (not shown in FIG. 1) that is capable of producing paper hard copies of any information displayed to a user. Non-limiting examples of paper hard copies that may be generated by the printer include reports that summarize the experimental protocol for an assay, the results of an assay, interpretations of the results of an assay, recommendations based on the results of an assay, and/or producing ranked lists of agents or groupings of agents based on the results of an assay.

Microbial Taxa Classification Schemes

Microbial taxa may be classified according to a variety of different schemes. Different classification schemes may result in taxa of different microbial compositions. Moreover, a particular taxon may comprise varied numbers of microbial species. In some examples, a microbial taxon may comprise a single microbial species. In other examples, a taxon may comprise from about 1 microbial species to about 1,000,000 microbial species. In other examples, a taxon may comprise from about 1 microbial species to about 10,000 microbial species. In other examples, a taxon may comprise from about 1 microbial species to about 100 microbial species. In other examples, a taxon may comprise from about 1 microbial species to about 10 microbial species. In still other examples, a taxon may comprise about 1, 10, 100, 1,000, 10,000, 100,000, or 1,000,000 microbial species. Moreover, microbial taxa may vary in the number of component microbial species comprised in each microbial taxon.

Microbial taxa may be arranged according to parsimonious trees such that nodes of the trees are species ordered in an evolutionary hierarchy. Taxa may be grouped, for example, in clades according to descendants of a node in the tree, such that all descendants from a common ancestor (or node) are grouped within a microbial taxon. Sub-taxa may also be derived for nodes at lower levels of the tree in an analogous fashion. Alternatively, more complicated schemes may be used to distinguish taxa within a parsimonious tree.

Microbial taxa may be arranged according to classical Linnaean taxonomy. Linnaean taxonomy generally relies on ordering species at various ranks such that organisms at a given rank all share one or more common characteristic. A common characteristic, for example, may be a common anatomical or structural feature shared by members of a given taxon. Non-limiting examples of classical Linnaean taxonomy, in order of highest rank to lowest rank, include: domains, kingdoms, phyla, classes, orders, families, genera, or single species. In general, a genus name and species name indicates a unique species using classical Linnaean taxonomy.

Microbial taxa may be arranged as operational taxonomic units (OTUs). For a thorough description of arrangement of microbial taxa into OTUs, see U.S. Patent Application Publication No. 2012/0165215 and U.S. Patent Application Publication No. 2009/0291858 which are both incorporated in their entirety herein by reference. An operational taxon unit (OTU) refers to a group of one or more organisms that can be represented as a node in a clustering tree. The level of a cluster is determined by its hierarchical order. In some examples, an OTU is a group tentatively assumed to be a valid taxon for purposes of phylogenetic analysis. In other examples, an OTU is any of the extant taxonomic units under study. In other examples, an OTU is given a name and a rank. For example, an OTU can represent a domain, a sub-domain, a kingdom, a sub-kingdom, a phylum, a sub-phylum, a class, a sub-class, an order, a sub-order, a family, a subfamily, a genus, a subgenus, or a species. In some cases, OTUs can represent one or more organisms from the kingdoms eubacteria, protista, or fungi at any level of a hierarchal order. In other cases, an OTU represents a prokaryotic or fungal order. Moreover, OTUs may be derived for example by a common physical attribute shared by its component organisms or may be derived from evolutionary hierarchy.

Alternatively, OTUs may be derived by other means such as by clustering organisms into OTUs by identifying of one or more conserved genes and/or polynucleotide sequence homologies for shared genes comprised in a plurality of organisms to-be-clustered. Highly conserved polynucleotides usually show at least about 80%, 85%, 90%, 92%, 94%, 95%, or 97% homology across a domain, kingdom, phylum, class, order, family or genus, respectively. The sequences of these polynucleotides can be used for determining evolutionary lineage or making a phylogenetic determination and are also known as phylogenetic markers.

A database of nucleic acid sequences may be used to organize organisms into particular OTUs based on one or more conserved genes and/or highly homologous nucleic acid sequences shared by a group of organisms. The choice of database that is used to assign organisms to OTUs is dependent on a number of factors with non-limiting examples that include the total number of sequences within the database, the length of the overall sequences or the length of highly conserved regions within the sequences listed in the database, and the quality of the sequences therein. Typically, databases with longer target regions of conserved sequence may generally contain a larger total number of possible sequences that can be compared. In some examples, the sequences in a database are at least about 10, 50, 100, 200, 300, 400, 500, 600, 700, 800, 900, 1,000, 1,200, 1,400, 1,600, 1,800, 2,000, 4,000, 8,000, 16,000 or 24,000 nucleotides long. Moreover, databases with a larger number of sequences may generally provide greater numbers of sequences from which to choose. In some examples, a database contains at least about 10,000, 20,000, 30,000, 40,000, 50,000, 60,000, 70,000, 80,000, 100,000, 200,000, 500,000, 1,000,000 or 2,000,000 sequences.

A database used for the selection of OTUs may comprise at least about 50%, 60%, 70%, 80%, 90%, 95%, 96%, 97%, 98%, 99% or up to 100% of the known sequences of the organisms to be clustered into OTUs. The sequences for each individual organism in the database can include more than about 20%, 30%, 40%, 50%, 60%, 70%, 80%, 90%, 95%, or 100% of the genome of the organism, or of the non-redundant regions thereof.

A variety of existing databases may be used to assign organisms to an OTU based on nucleic acid sequences. A listing of almost 40,000 aligned 16S rRNA gene sequences greater than 1250 nucleotides in length can be found on the Greengenes web application (greengenes.secondgenome.com), a publicly accessible database run by the Greengenes Consortium. Other publicly accessible databases include GenBank, Michigan State University's ribosomal database project, the Max Planck Institute for Marine Microbiology's Silva database, and the National Institute of Health's NCBI. Proprietary sequence databases or combinations created by amalgamating the contents of two or more private and/or public databases can also be used to assign organisms to a given OTU.

As noted above, OTUs may be arranged by sequence homology of a conserved polynucleotide. The conserved polynucleotide may be from a highly conserved gene or the conserved polynucleotide may be from a highly conserved region of a gene with moderate or large sequence variation. Moreover, the highly conserved polynucleotide may be an intron, exon, or a linking section of nucleic acid that separates two genes.

The highly conserved polynucleotide used to assign organisms to OTUs may be a phylogenetic gene. Non-limiting examples of a phylogenetic gene includes the 5.8S ribosomal ribonucleic acid (rRNA) gene, 12S rRNA gene, 16S rRNA gene-prokaryotic, 16S rRNA gene-mitochondrial, 18S rRNA gene, 23S rRNA gene, 28S rRNA gene, gyrB gene, rpoB gene, fusA gene, recA gene, coxI gene, and the nifD gene. For eukaryotic species, rRNA genes can be nuclear, mitochondrial, or both. In some cases, the spacer region between highly conserved segments of two genes can be used. For example, the internal transcribed spacer (ITS) region between 16S and 23S rRNA genes can be used to differentiate closely related taxa with or without consideration of other rRNA genes, including conserved sections of either the 16S or 23S rRNA gene.

Due to structural constraints necessary for proper functioning of 16S rRNA when comprised in protein synthesis machinery (e.g., ribosomes), specific regions throughout the gene have a highly conserved polynucleotide sequence although non-structural segments may have a high degree of variability. Regions of the 16S rRNA gene that possess high levels of variability include the V1, V2, V3, V4, V5, V6, V7, V8, and V9 regions of the gene. These and other regions of high variability may be detected, for example, to distinguish/enumerate OTUs at a single species level, while regions of less variability might be used to distinguish OTUs that represent a subgenus, a genus, a subfamily, a family, a sub-order, an order, a sub-class, a class, a sub-phylum, a phylum, a sub-kingdom, or a kingdom. Such a classification scheme may be useful for identifying closely related microorganisms and OTUs from a background or pool of closely related organisms.

Microbial taxa may be arranged by virtue of other descriptors with non-limiting examples that include transcriptomes, proteomes, metabolomes, and metagenomes. Such descriptors may be both indicators of microbial compositions and functionality. In some examples, microbial organisms may be arranged into taxa via clusters of organisms with similar, full or partial transcriptomes. Transcriptomes generally refer to a set of ribonucleic acid (RNA) molecules of a living organism. RNA molecules may include mRNA, rRNA, transfer RNA (tRNA), and other non-coding RNA. Transcriptomes may be an entire set of all RNA molecules of a living organism or may be a particular subset of RNA molecules. Moreover, taxa may be arranged based on full organism transcriptomes or may be based on partial transcriptomes.

In some examples, microbial organisms may be arranged into taxa via clusters of organisms with similar proteomes. A proteome generally refers to a set of proteins expressed by a living organism. Proteomes may be an entire set of all proteins of a living organism or may be a particular subset of proteins. Moreover, taxa may be arranged based on full organism proteomes or may be based on partial proteomes.

In some examples, microbial organisms may be arranged into taxa via clusters of organisms with similar metabolomes. A metabolome generally refers to a set of small-molecule metabolites (such as metabolic intermediates, hormones and other signaling molecules, and secondary metabolites) found within a living organism. Metabolomes may be an entire set of all metabolites found within a living organism or may be a particular subset of metabolites. Moreover, taxa may be arranged based on full organism metabolomes or may be based on partial metabolomes.

In some examples, microbial organisms may be arranged into taxa via clusters of organisms with similar metagenomes. A metagenome generally refers to genetic material recovered directly from environmental samples, such as for example a living organism. Metagenomes may be an entire set of all genetic material found within a living organism or may be a particular subset of genetic material. Moreover, taxa may be arranged based on full metagenomes or may be arranged based on partial metagenomes.

EXAMPLES

Example 1—MESA Assay

Experiments were carried out using three human donor fecal samples. Samples were incubated in a micro-well plates as well as larger volume tubes, in the presence of various carbon sources. 16S rRNA sequencing was performed to determine shifts in microbiota profiles across time and donor. Principle component analysis and relative taxa frequency were determined to assess whether changes occurred according to donor, carbon source addition, and time.

Assay Setup and DNA Extraction

A fecal sample was obtained from a human donor. 1 gram of the fecal sample was added to 10 mL phosphate buffered saline (PBS) to form a slurry of 10% (w/v) fecal sample. In triplicate, 40 µL of the above slurry was added to each of three wells in a 48 well plate. 360 µL of minimal bacterial broth medium (comprising 2 grams ("g")/liter ("L") of peptone water, 1 g/L of yeast extract, 0.1 g/L of NaCl, 0.04 g/L of $K_2HPO_4$, 0.01 g/liter of $MgSO_4.7H_2O$, 0.01 g/L of $CaCl_2 \cdot 2H_2O$, 2 g/L of $NaHCO_3$, 0.5 g/L of bile salts, 0.5 g/L of L-cysteine hydrochloride, 50 mg/L of hemin, 10 µL/L of vitamin K1, 2 mL/L of Tween 80, and 0.05% (wt/vol) resazurin solution, pH 7) was then added to each well to form a 400 µL culture comprising 1% w/v fecal slurry. 100 µL culture is then collected for 16S rRNA gene sequencing.

In triplicate, 200 µL of the above slurry was added to each of three tubes. 1.8 mL of minimal broth medium was then added to each well to form a 2 mL culture comprising 1% w/v fecal slurry. 0.5 mL of the culture is then collected for 16S rRNA gene sequencing.

DNA extraction of 100 µL aliquots obtained from microplate experiments revealed that 100 µL of culture was not a sufficient aliquot for obtaining sufficient amounts of DNA. Instead, it was determined that all 400 µL the total culture volume was required.

DNA extraction of 0.5 mL aliquots obtained from tube experiments revealed that 0.5 mL of culture was a sufficient aliquot for obtaining sufficient amounts of DNA. However, it was determined that a 1 mL aliquot was a better for DNA sequencing.

MESA Experiment

A fecal sample was obtained from each of three human donors, Donor 1, Donor 2, and Donor 3. 1 gram of each fecal sample was added to 10 mL phosphate buffered saline (PBS) to form three separate slurries of 10% (w/v) fecal sample.

A total of 36 experiments was setup on a 48-well plate (referred to herein as "microplate experiments"). For each slurry obtained from Donor 1 Donor 2, or Donor 3, 40 µL of the respective slurry was added to each of twelve wells of the plate. For each of these 12 wells, 360 µL of water (control), water comprising fructose, or water comprising fructose oligosaccharide (FOS) were added. After addition of water, three of the twelve wells comprised slurry+water; three of the twelve wells comprised slurry+2% w/v fructose+water; three of the twelve wells comprised slurry+0.5% w/v FOS+water; and three of the twelve wells comprised slurry+2% w/v FOS+water. A summary of the experiments is shown in Table 1. In Table 1, "Donor 1" represents slurry from Donor 1, "Donor 2" represents slurry from Donor 2, and "Donor 3" represents slurry from Donor 3. The microplate was then incubated for 24 hours in an anaerobic chamber under 80% nitrogen, 10% carbon dioxide, and 10% hydrogen ($H_2$). A total of 8 experiments were prepared each in a vial (referred to herein as "tube experiments"). 200 µL of slurry from Donor 1 was added to each of the 8 vials. In 4 of the vials, 1.8 mL of water comprising FOS was added for a final concentration of 2% w/v FOS. For the other four vials, 1.8 mL of water (control) was added. Two of the vials comprising FOS and the two vials comprising water are incubated for 24 hours in an anaerobic chamber (comprising 80% nitrogen, 10% carbon dioxide, and 10% hydrogen ($H_2$)) at 37° C. The other four vials are incubated for 16 hours.

DNA was extracted from each sample (well or tube) and quantified using a PicoGreen method. DNA is also extracted from an aliquot of each slurry obtained from Donor 1, Donor 2, and Donor 3. DNA comprising the variable region (V4) region of the 16S rRNA gene was amplified and sequenced using the MiSeq platform from Ilumina. Principle component analyses (PCoA) were performed to identify Unifrac distances (degree of similarity/dissimilarity) of the different treatment groups. Relative taxa representation for the various treatment groups was determined at the phylum, class, order, family, genus and species levels using operational taxonomic units (OTUs) by comparing results to the Green-Genes database.

Results

Figure 2:
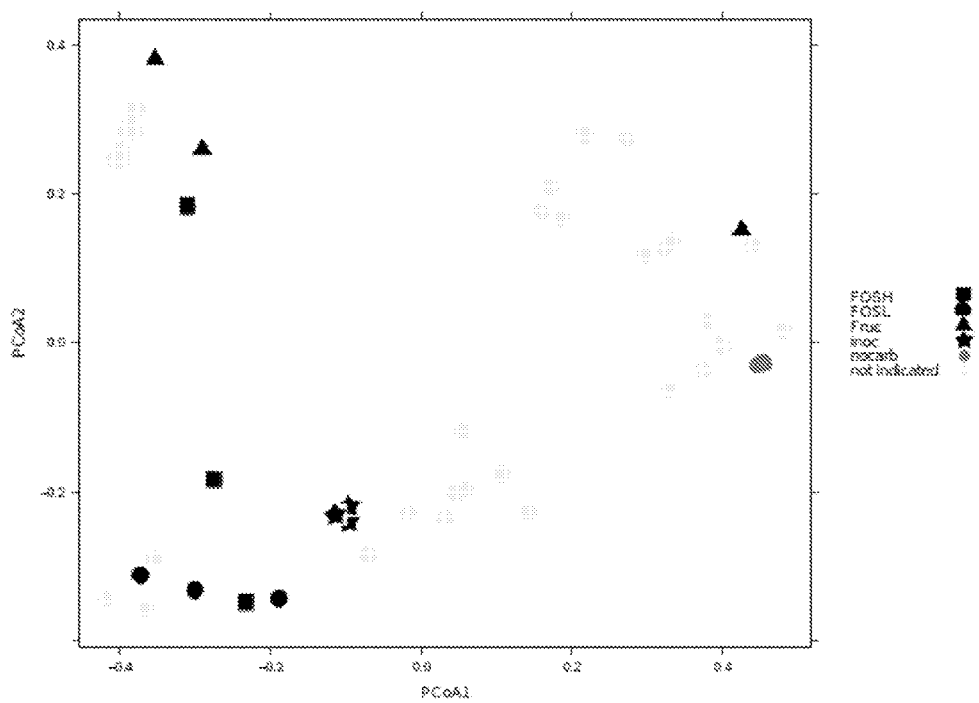
FIG. 2 is a plot summarizing a principal component analysis (PCoA) for microplate experiments with respect to Donor 1 as described in Example 1.

In FIG. 2, PCoA and calculation of Unifrac distances shows microbiota profiles of experiments related to Donor 1 in the microplate experiments (n=3 for each experimental condition (e.g., no agent (control), 2% fructose, 0.5% FOS, 2% FOS)). As shown, a difference in the microbiota profile of control experiments is noticeable after the 24-hour incubation period ("nocarb"—dark gray circles) when compared to non-incubated slurry ("inoc"—stars). Hence, a "shift" in the profile can be observed. Also shown are shifts in microbiota profiles for 2% fructose experiments ("fruc"—triangles), 0.5% FOS experiments ("FOSL"—black circles), or 2% FOS experiments ("FOSH"—squares). As shown in FIG. 2, test agents appear to shift microbiota differently from controls, indicating that the tested agents may have an effect on the evaluated microbial communities in Donor 1.

Figure 3:
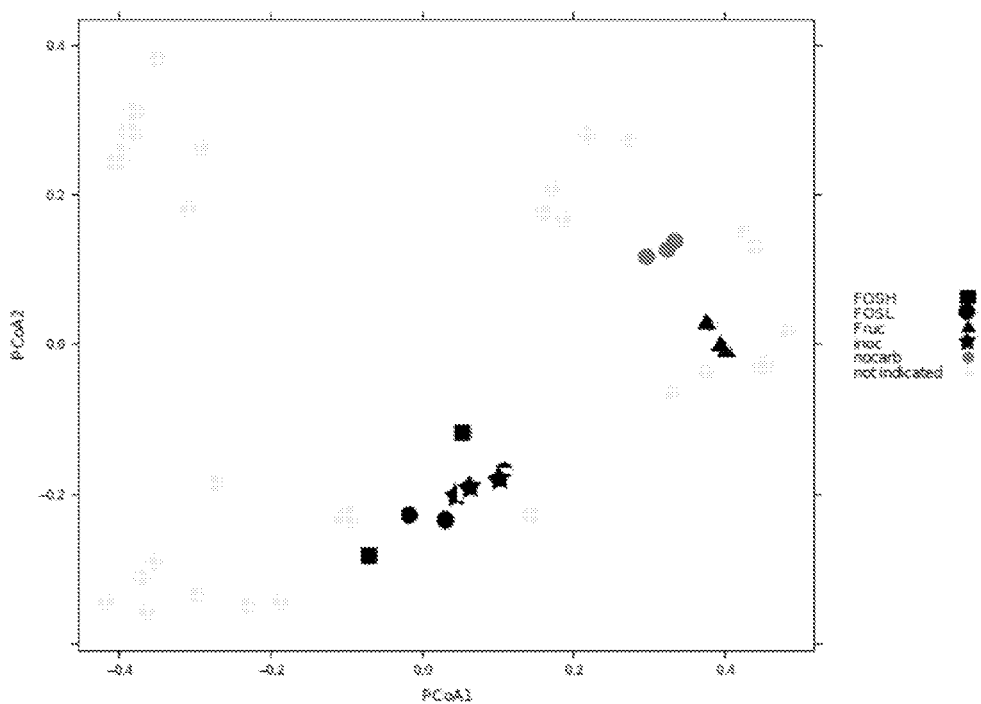
FIG. 3 is a plot summarizing a principal component analysis (PCoA) for microplate experiments with respect to Donor 2 as described in Example 1.

In FIG. 3, PCoA and calculation of Unifrac distances shows microbiota profiles of experiments related to Donor 2 in the microplate experiments (n=3 for each experimental condition). As shown, a difference in the microbiota profile of control experiments is noticeable after the 24-hour incubation period ("nocarb"—dark gray circles) when compared to non-incubated slurry ("inoc"—stars). Also shown are shifts in microbiota profiles for 2% fructose experiments ("fruc"—triangles), 0.5% FOS experiments ("FOSL"—black circles), or 2% FOS experiments ("FOSH"—squares).

As shown in FIG. 3, test agents appear to shift microbiota differently from controls, indicating that the tested agents may have an effect on the evaluated microbial communities in Donor 2.

Figure 4:
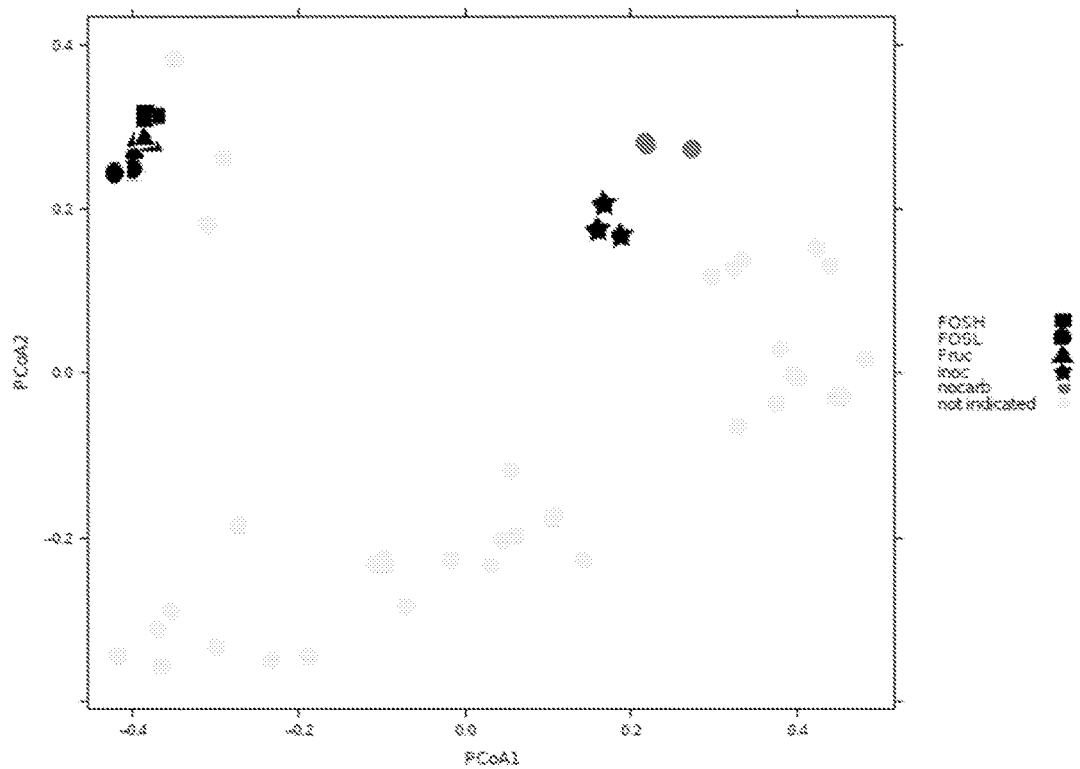
FIG. 4 is a plot summarizing a principal component analysis (PCoA) for microplate experiments with respect to Donor 3 as described in Example 1.

In FIG. 4, PCoA and calculation of Unifrac distances shows microbiota profiles of experiments related to Donor 2 in the microplate experiments (n=3 for each experimental condition). As shown, a difference in the microbiota profile of control experiments is noticeable after the 24-hour incubation period ("nocarb"—dark gray circles) when compared to non-incubated slurry ("inoc"—stars). However, when compared to results from Donor 1 (FIG. 2) and/or Donor 2 (FIG. 3) shifts between control experiments and non-incubated slurry occur to a lesser degree. Also shown are shifts in microbiota profiles for 2% fructose experiments ("fruc"-triangles), 0.5% FOS experiments ("FOSL"—black circles), or 2% FOS experiments ("FOSH"-squares). As shown in FIG. 4, test agents appear to shift microbiota differently from controls, indicating that the tested agents may have an effect on the evaluated microbial communities in Donor 3. Also, test agents appear to shift the microbiome from controls similarly in Donor 3. Comparison of results between Donor 1 (FIG. 2), Donor 2 (FIG. 3), and Donor 3 (FIG. 4), however, indicates that shifts of microbiota when in contact with the set of test agents were noticeably different between the three different donors.

Figure 5:
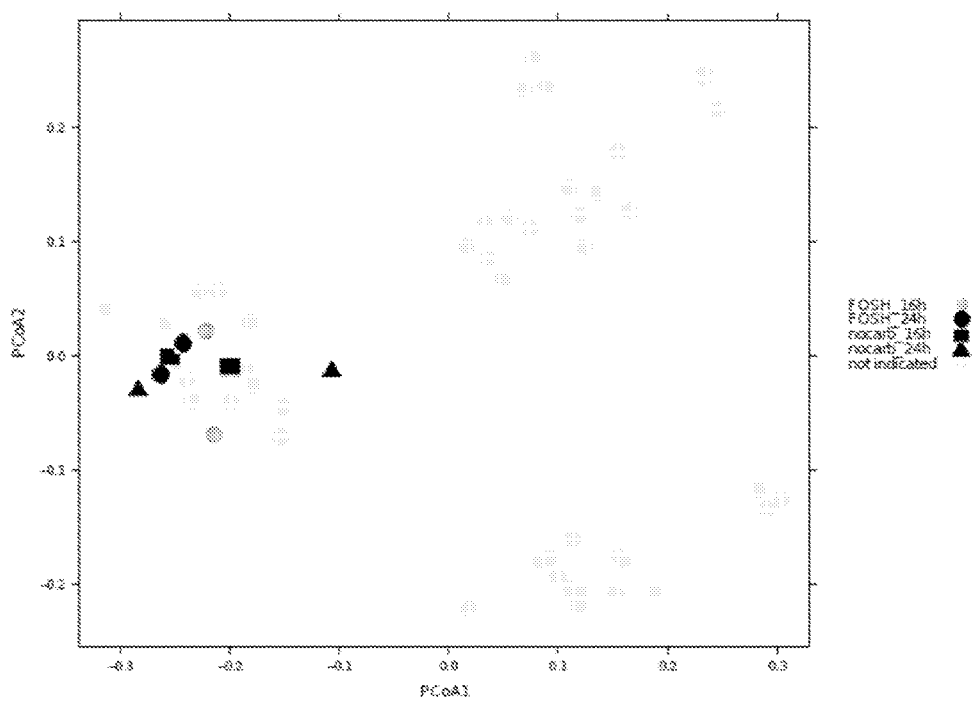
FIG. 5 is a plot summarizing a principal component analysis (PCoA) for tube experiments with respect to differing incubation times as described in Example 1.

In FIG. 5, PCoA and calculation of Unifrac distances shows microbiota profiles of experiments in the tube experiments (n=2 for each experimental condition (e.g., no agent (control)+16 hour incubation ("nocarb_16 h"—squares); no agent (control)+24 hour incubation ("nocarb_24 h"—triangles); 2% FOS+16 hour incubation ("FOSH_16 h"—dark gray circles); 2% FOS+24 hour incubation ("FOSH_24 h"—black circles))). As shown, shifts in microbial communities in control experiments between the two incubation times are similar as are shifts in microbial communities in experiments using FOS. Results suggest that a 16 hr or 24 hr incubation time may both give similar results.

Figure 6:
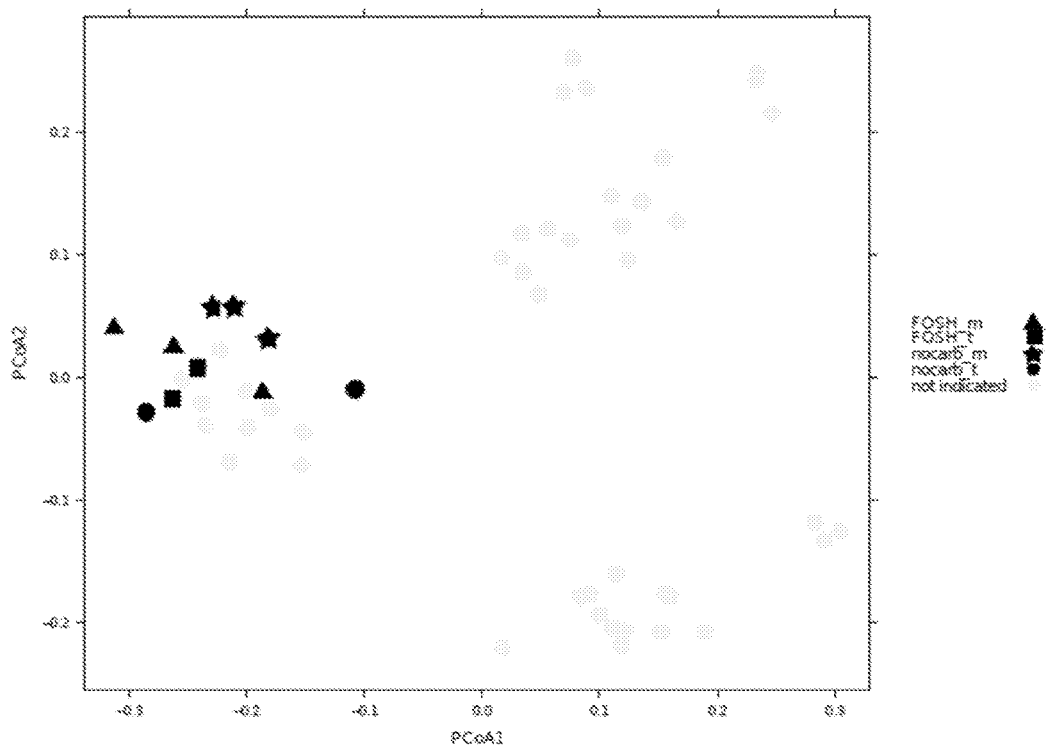
FIG. 6 is a plot summarizing a principal component analysis (PCoA) for microplate and tube and experiments comparing micronized assays to those of larger volume as described in Example 1.

In FIG. 6, PCoA and calculation of Unifrac distances shows microbiota profiles of 24 hour incubation time control ("nocarb_t"—black circles) and 2% FOS experiments ("FOSH_t"-squares) in the tube experiments and the control ("nocarb_m"—stars) and 2% FOS experiments ("FOSHm"—triangles) in microplate experiments (n=2 for tube experiments and n=3 for microplate experiments). As shown, shifts in microbial communities in control experiments between the two assay formats are similar as are shifts in microbial communities in experiments using FOS. Results suggest that a micronized version of an assay may give similar results to an assay completed with larger volumes.

Figure 7:
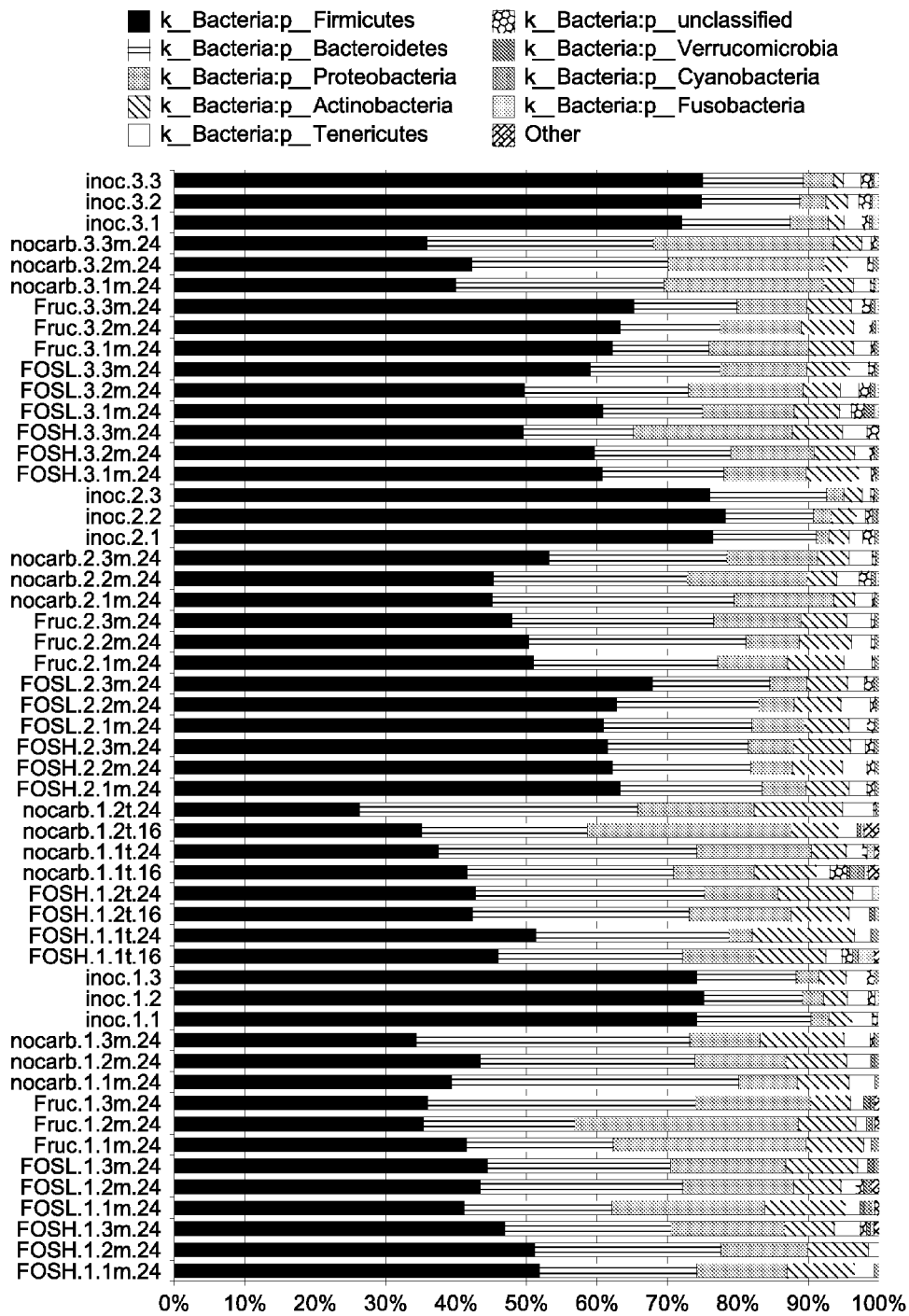
FIG. 7 is a bar chart summarizing the proportions of OTUs classified at the phylum level for experiments described in Example 1.

In FIG. 7, proportions of OTUs classified at the phylum level are shown for all donors, experiment sets (e.g., tube or microplate), and experimental conditions. FIG. 7 shows the top nine richest taxa at the phylum rank and the relative proportion of OTUs unclassified at either the phylum level or at all levels. Although PCoA in FIG. 2, FIG. 3, and FIG. 4 show differences in microbiome shifts between the three donors, the relative proportions of the major phyla are similar between donors across experimental conditions tested.

Figure 8:
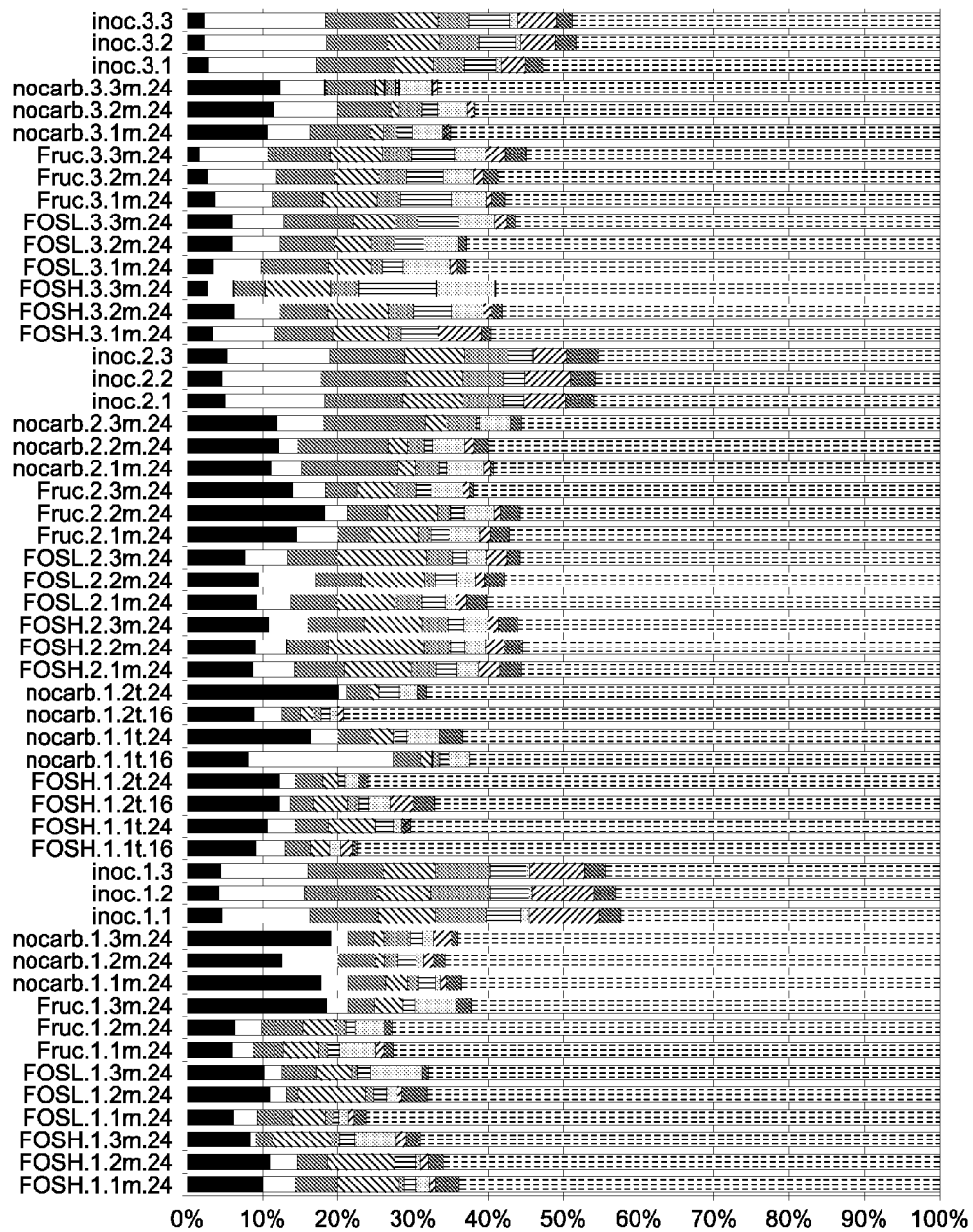
FIG. 8 is a bar chart summarizing the proportions of OTUs classified at the species level for experiments described in Example 1.

In FIG. 8, proportions of OTUs classified at the species level are shown for all donors, experiment sets (e.g., tube or microplate), and experimental conditions. FIG. 8 shows the top nine richest taxa at the species rank and the relative proportion of OTUs unclassified at either the species or at all levels. Although PCoA in FIG. 2, FIG. 3, and FIG. 4 show differences in microbiome shifts between the three donors, the relative proportions of the major species are similar between donors across experimental conditions tested.

Similar results (not shown) were obtained for analyses conducted on OTUs classified at the class, order, family, and genus levels.

Figure 9:
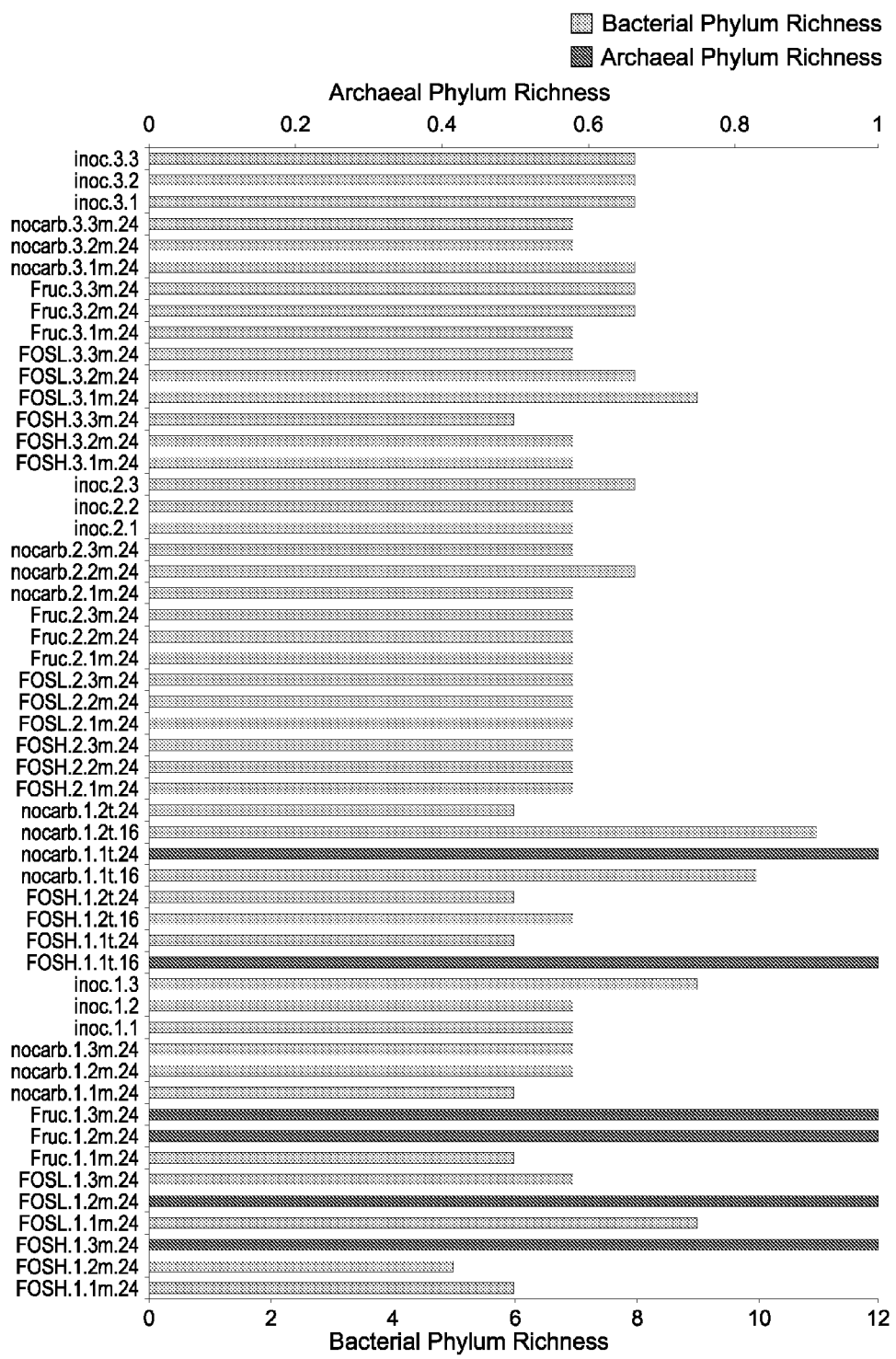
FIG. 9 is a bar chart summarizing the bacterial and archael richness for OTUs classified at the phylum level for experiments described in Example 1.

In FIG. 9, the bacterial (gray) and archael (black) taxon richness for OTUs classified at the phylum level is shown for all donors, experiment sets, and experimental conditions. Taxon richness refers to the number of unique phyla detected by V4 16S rRNA gene sequencing. As shown in FIG. 9 and in cases where both bacterial and archael taxon richness was evaluated for a sample, the richness of bacterial and archael taxa at the phyla level are similar.

Figure 10:
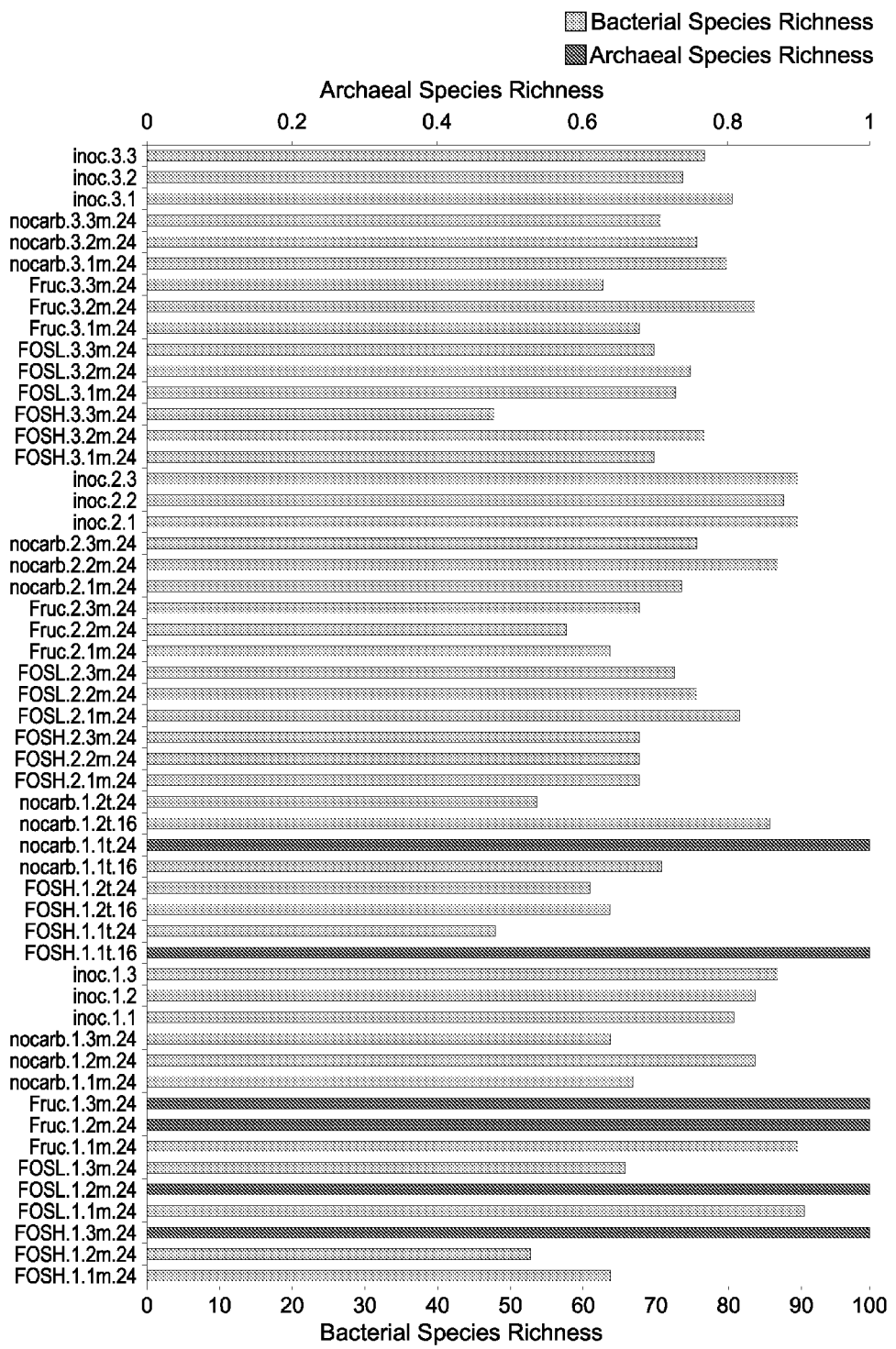
FIG. 10 is a bar chart summarizing the bacterial and archael richness for OTUs classified at the species level for experiments described in Example 1.

In FIG. 10, the bacterial (gray) and archael (black) taxon richness for OTUs classified at the species level is shown for all donors, experiment sets, and experimental conditions. Taxon richness refers to the number of unique species detected by V4 16S rRNA gene sequencing. As shown in FIG. 10 and in cases where both bacterial and archael taxon richness was evaluated for a sample, the richness of bacterial and archael taxa at the species level are similar.

TABLE 1

Setup of Microplate Experiments in Example 1

| Donor1 + Control | Donor1 + 2% Fructose | Donor1 + 0.5% FOS | Donor1 + 2% FOS | Donor3 + Control | Donor3 + 2% Fructose | Donor3 + 0.5% FOS | Donor 3 + 2% FOS |
|---|---|---|---|---|---|---|---|
| Donor1 + Control | Donor1 + 2% Fructose | Donor1 + 0.5% FOS | Donor1 + 2% FOS | Donor3 + Control | Donor3 + 2% Fructose | Donor3 + 0.5% FOS | Donor3 + 2% FOS |
| Donor1 + Control | Donor1 + 2% Fructose | Donor1 + 0.5% FOS | Donor1 + 2% FOS | Donor3 + Control | Donor3 + 2% Fructose | Donor3 + 0.5% FOS | Donor3 + 2% FOS |
| Donor2 + Control | Donor2 + 2% Fructose | Donor2 + 0.5% FOS | Donor2 + 2% FOS | | | | |
| Donor2 + Control | Donor2 + 2% Fructose | Donor2 + 0.5% FOS | Donor2 + 2% FOS | | | | |
| Donor2 + Control | Donor2 + 2% Fructose | Donor2 + 0.5% FOS | Donor2 + 2% FOS | | | | |

Example 2—Counseling and Subject Selection for Use of an Agent

A human subject is diagnosed with ulcerative colitis. A fecal sample is obtained from the subject and pre-processed into a slurry. The slurry is combined with an agent, approved for the treatment of ulcerative colitis, and additional reagents to form a reaction mixture. The reaction mixture is incubated at appropriate conditions. After incubation, DNA is extracted from the reaction mixture and the V4 region of the 16S rRNA gene is amplified sequenced. Via sequencing, appropriate microbial taxa (e.g., microbial taxa determined to be associated with ulcerative colitis, microbial known to be at risk for unwanted alteration, etc.) are enumerated and numerically manipulated. A numerical manipulation from an enumeration obtained from a group of subjects not afflicted with ulcerative colitis (a reference enumeration) is obtained from a stored database. A processor is used to compare the two numerical manipulations and determines that contacting samples obtained from the subject with the agent results in a shift in microbial taxa abundance in the direction of that observed from the reference enumeration. The results are thus used to select the subject for use of the agent to treat the subject's ulcerative colitis. These results are communicated to the subject in the form of counseling administered at a healthcare facility by a health care practitioner. During counseling the use of the agent as a therapy for ulcerative colitis and a dosing regimen of the agent are recommended. A summary of the results of the assay and the recommendations provided during counseling are provided to the subject on a printed report.

Example 3—Counseling and Subject Selection for Use of an Agent

A human subject is working with a new chemical process in a chemical production facility. The process produces a new chemical that may be potentially hazardous to microbiota of the human subject. A fecal sample is obtained from the subject and pre-processed into a slurry. An aliquot of the slurry is combined with the chemical and additional reagents to form a reaction mixture. A separate aliquot of the slurry is combined with just the additional reagents. The reaction mixtures are incubated at appropriate conditions. After incubation, DNA is extracted from both reaction mixtures and the V4 region of the 16S rRNA gene is amplified and sequenced. Via sequencing, appropriate microbial taxa are enumerated for each reaction mixture and the obtained enumerations numerically manipulated. A processor is used to compare the two numerical manipulations and determines that exposure of a sample obtained from the subject to the new chemical results in no appreciable shift in microbial taxa abundance in the direction of that observed for the sample not contacted with the new chemical. The results are thus used to approve the subject's use of and exposure to the new chemical. Results of the assay are communicated to the subject in the form of counseling administered at a healthcare facility by a health care practitioner. During counseling, it is communicated to the subject that the use of and exposure to the new chemical is cleared and an exposure limit is recommended based on the results of the assay. A summary of the results of the assay and the recommendations provided during counseling are provided to the subject on a printed report.

Example 4—Functionality Assays

Methods

Cecal/fecal slurry preparation: Briefly, cecal or fecal contents from human or mouse subjects were homogenized in anoxic (e.g., oxygen-free) phosphate buffered saline (PBS) as a 10% mixture, weight:volume. After centrifugation, slurries were diluted to 1% in a minimal medium ("MESA medium") equilibrated in 10% $H_2$, 10% $CO_2$, and 80% $N_2$, consisting of 2 g/liter of peptone water, 1 g/liter of yeast extract, 0.1 g/liter of NaCl, 0.04 g/liter of $K_2HPO4$, 0.04 g/liter of $KH_2PO_4$, 0.01 g/liter of $MgSO_4$-$7H_2O$, 0.01 g/liter of $CaCl_2$-$2H_2O$, 2 g/liter of $NaHCO_3$, 0.5 g/liter of bile salts, 0.5 g/liter of L-cysteine hydrochloride, 50 mg/liter of hemin, 10 microliter of vitamin K1, 2 ml/liter of Tween 80, and 0.05%$_0$ (wt/vol) resazurin solution, and at pH 7.0. Slurries were cultured in an anaerobic cabinet for 4-48 hr under anaerobic conditions. After incubation, slurries were pelleted and processed for genomic DNA purification and amplicon library production, followed by 16S rRNA gene sequencing using Ilumina MiSeq sequencing technology.

A portion of supernatants obtained from pelleting were placed on either HT29 MTX human epithelial cells or on mouse colon organotypic cultures. In a parallel set of experiments, supernatants were diluted 1:2 with phosphate buffered saline (PBS) and added to cultures. MESA medium and diluted MESA medium (1:2 dilution) not containing homogenized material were also added to either HT29 MTX human epithelial cells or mouse colon organotypic cultures as a control.

HT29 MTX cells were grown as monolayer cultures in trans-well plates. Organotypic cultures were obtained by splaying mouse colon tissue and flushing with PBS containing Pen/Strep. Three millimeter ("mm") sections were punched out using a skin biopsy tool to obtain explants. Explants were placed in trans-well plates with DMEM medium supplemented with calf serum. Cells or organotypic cultures were incubated with supernatants or basal medium for 24 hours. At the conclusion of incubation, barrier function, cellular viability, and cytokine release were measured in the cultures.

For HT29 MTX cells grown in monolayer, barrier function was measured by quantifying the penetration of a 70 kDa FITC-Dextran label through the monolayer. Increased penetration of fluorescence through the monolayer was used as a measure of increased permeability/barrier breakdown. Viability was measured by quantifying DAPI label incorporation into the cultures and the fluorescence signal quantified. Cytokines were measured in the media of cultures by ELISA.

For organotypic cultures, barrier function was measured by incorporation and quantification of 70 kDa FITC-Dextran into the explant. Viability was measured by quantifying incorporation of the Live/Dead™ fluorescence marker into the explant; increased fluorescence served as an index of decreased viability of the explant in response to supernatant additions. Cytokines were measured in the media of cultures by ELISA. In parallel experiments, antibiotics were added with supernatants to determine the effect of diminished bacterial viability (e.g., due to antibiotic treatment) on the various readouts.

In another set of experiments, live bacteria (e.g., cecum-derived bacteria) were placed on either the HT29 MTX cells or the organotypic cultures for various times, and barrier function, viability, and cytokines measured as described above for supernatant additions. In parallel experiments, antibiotics were added with the bacteria to determine the effect of diminished bacterial viability on the various readouts.

Results

Barrier Function and Viability—HT29 MTX Cells

Figure 11:
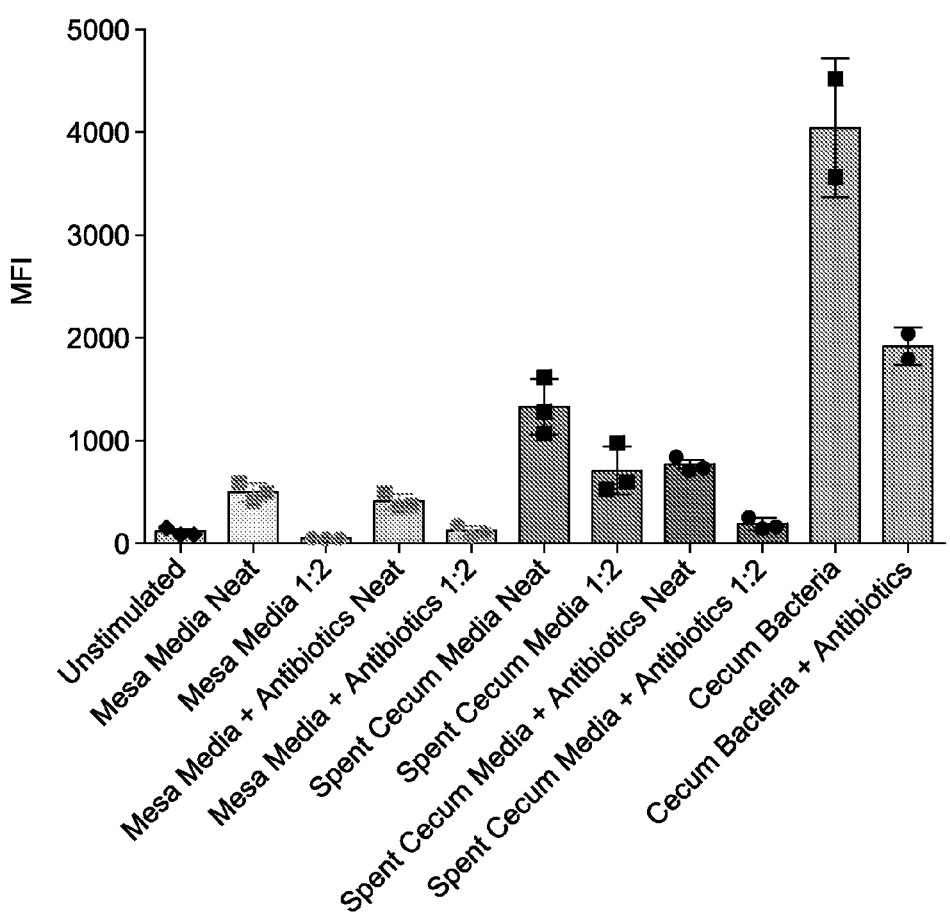
FIG. 11 is a bar chart summarizing the results of experiments described in Example 4.
Figure 12:
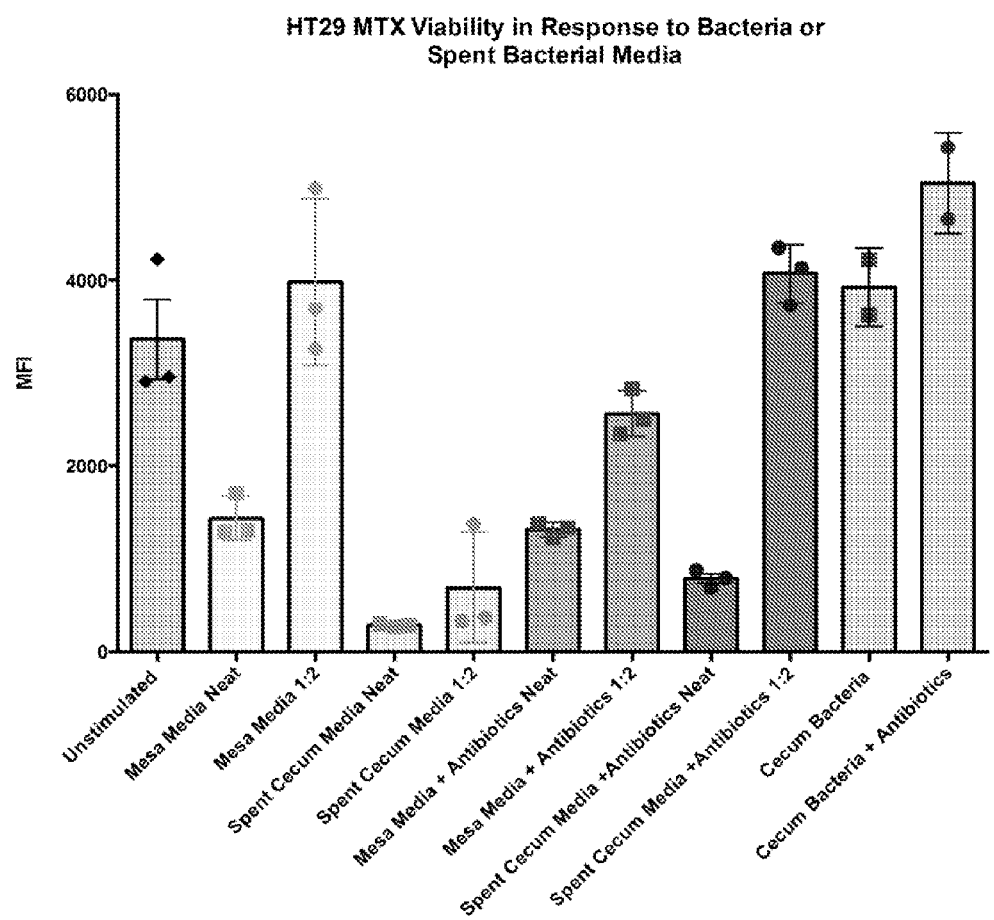
FIG. 12 is a bar chart summarizing the results of experiments described in Example 4.

FIG. 11 shows the effect of various cecal-derived supernatants or bacteria on barrier permeability in HT29 MTX cells. FIG. 12 is a companion figure showing viability of HT29 MTX cultures. Spent bacterial supernatants induced cell loss and dextran leakage; while bacterial components induced barrier breakdown in the absence of cell loss. Addition of antibiotics into the cecal cultures mitigated the effect of both bacteria and their spent supernatants on host function. "MESA Media" in FIGS. 11 and 12 refers to control basal medium used to generate slurries and "Spent Cecum Media" refers to supernatants generated from cecal slurries subject to anaerobic culture.

Cytokines—HT29 MTX Cells

Figure 13:
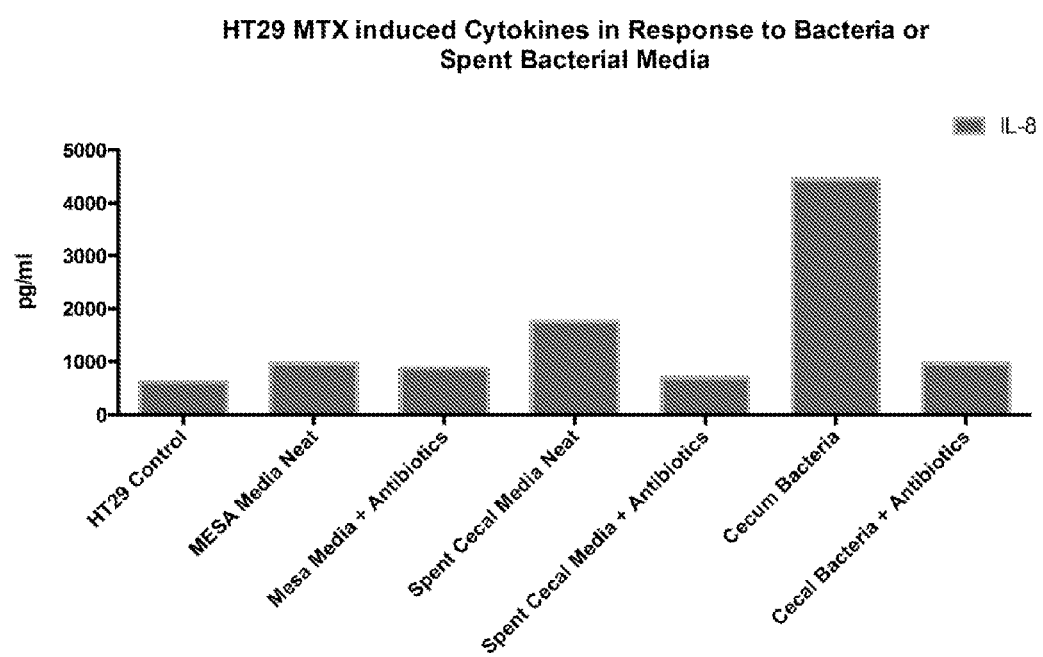
FIG. 13 is a bar chart summarizing the results of experiments described in Example 4.

FIG. 13 shows the effect of various cecal-derived supernatants or bacteria on IL-8 cytokine production in HT29 MTX cells. Spent bacterial supernatants (e.g., supernatants obtained from cecal slurries subject to anaerobic conditions) and bacteria induced IL-8 production from HT-29 MTX cells. Addition of antibiotics into the cecal cultures mitigated the effect of both bacteria and their spent supernatants on IL-8 responses. "MESA Media" in FIG. 13 refers to control basal medium used to generate slurries and "Spent Cecum Media" refers to supernatants generated from cecal contents and subject to anaerobic culture.

Barrier Function and Viability—Organotypic Cultures

Figure 14:
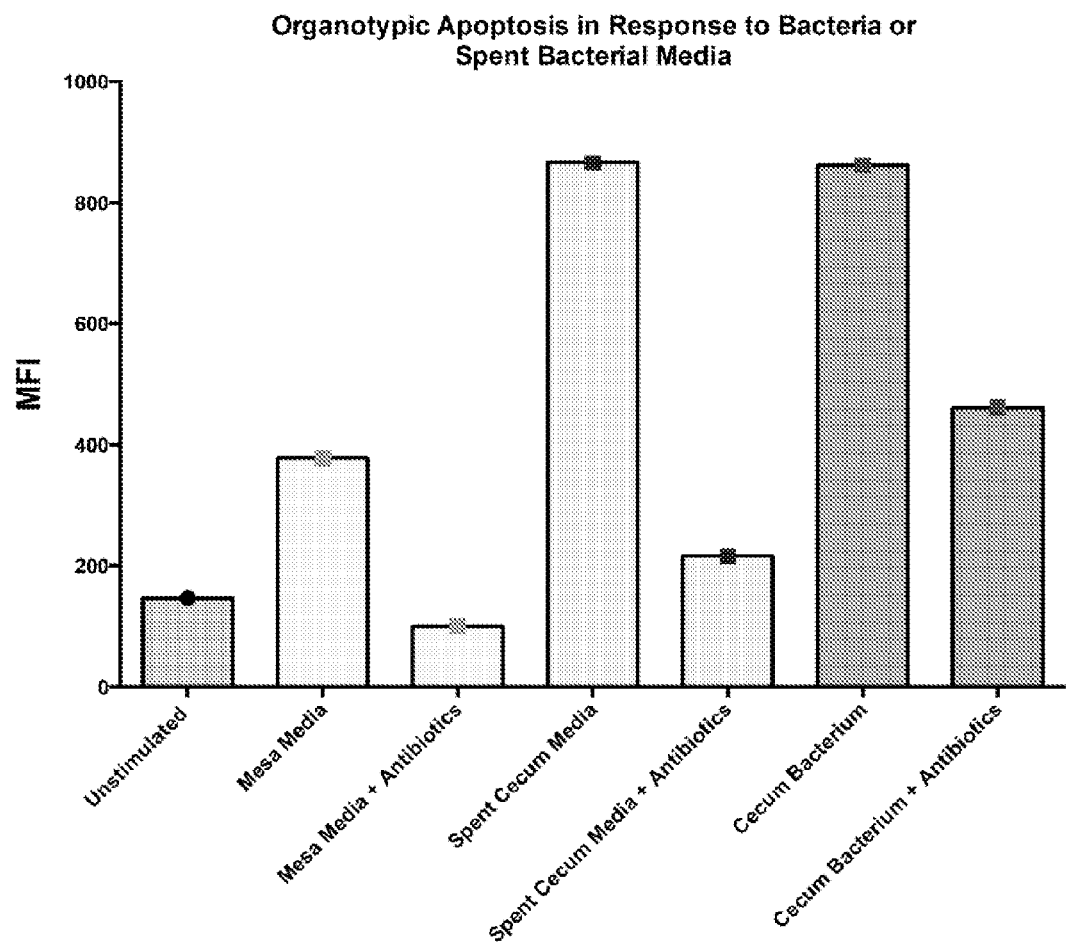
FIG. 14 is a bar chart summarizing the results of experiments described in Example 4.

FIG. 14 shows the effect of various cecal-derived supernatants or bacteria on barrier permeability in mouse organotypic cultures. Spent bacterial supernatants (e.g., supernatants obtained from cecal slurries subject to anaerobic conditions) induced dextran leakage; while bacterial components induced barrier breakdown in the absence of cell loss. Addition of antibiotics into the cecal cultures mitigated the affect of both bacteria and their spent supernatants on host function.

Figure 15:
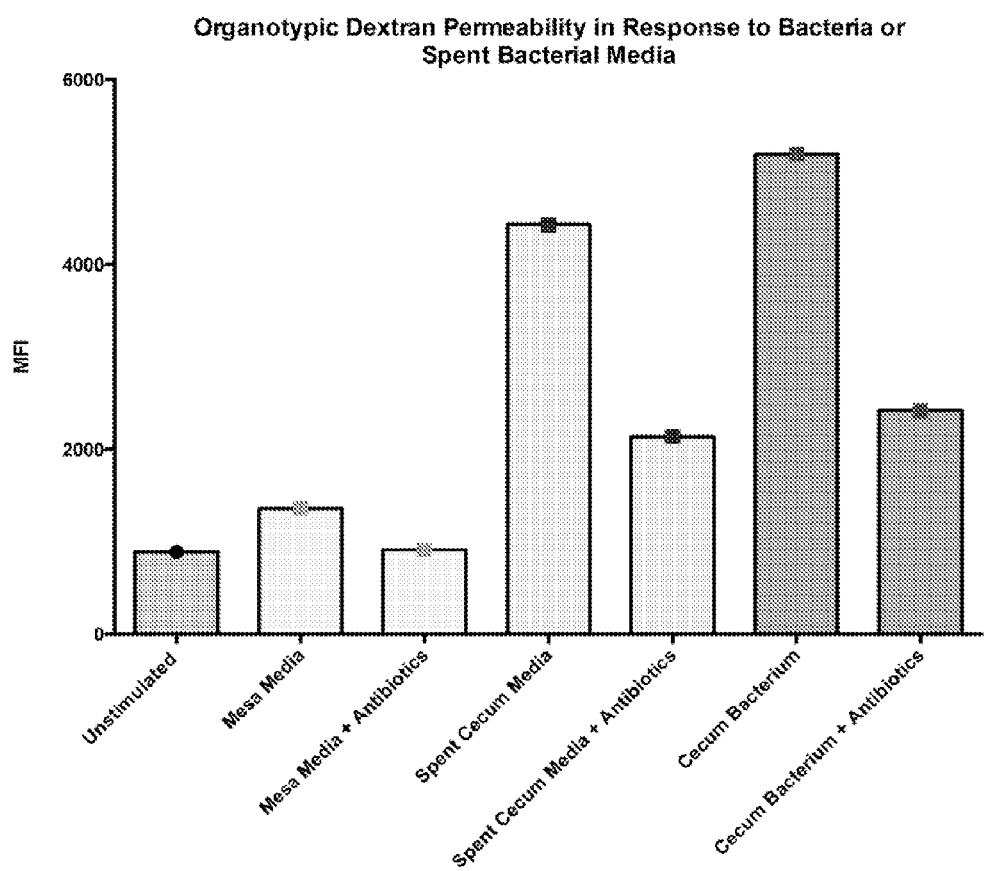
FIG. 15 is a bar chart summarizing the results of experiments described in Example 4.

FIG. 15 shows the effect of various cecal-derived supernatants or bacteria on viability in mouse organotypic cultures. Spent bacterial supernatants (e.g., supernatants obtained from cecal slurries subject to anaerobic conditions) decreased viability while bacterial components induced breakdown in the absence of cell loss. Addition of antibiotics into the cecal cultures mitigated the effect of both bacteria and their spent supernatants on host function.

Cytokines—Organotypic Cultures

Figure 16:
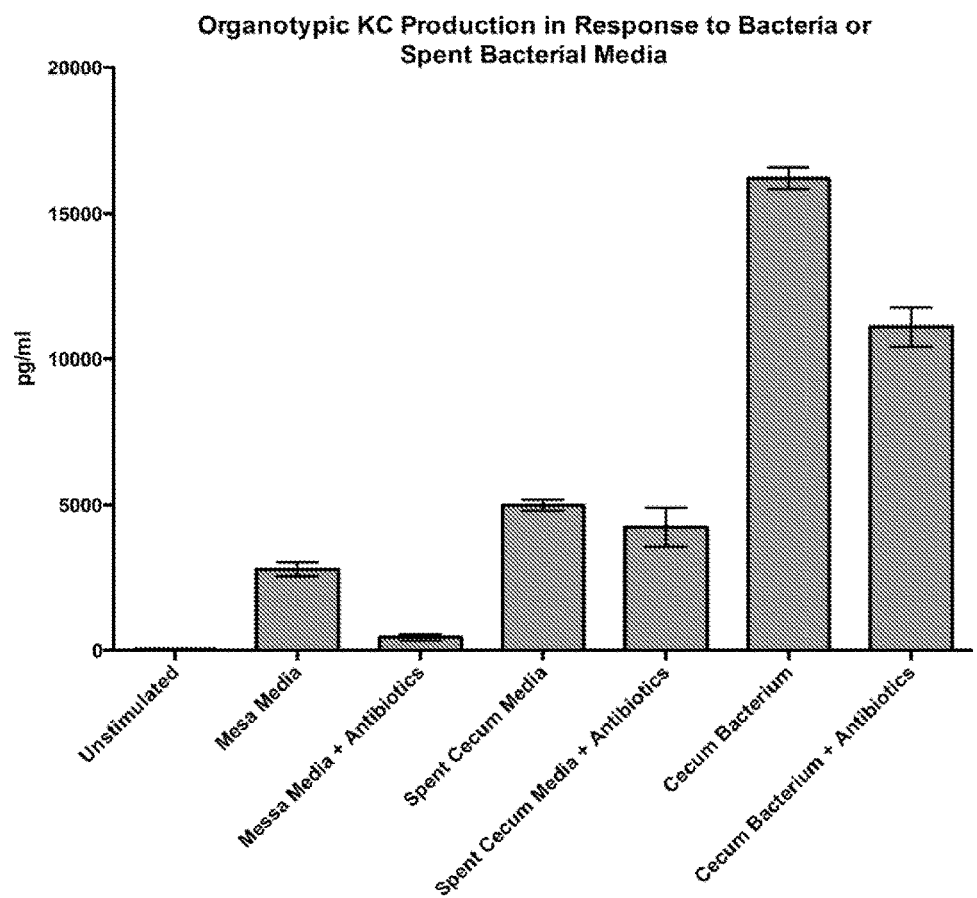
FIG. 16 is a bar chart summarizing the results of experiments described in Example 4.

FIG. 16 shows the effect of various cecal-derived MESA media or bacteria on KC (e.g., mouse IL-8) production in organotypic cultures. Spent bacterial supernatants (e.g., supernatants obtained from cecal slurries subject to anaerobic conditions) and bacteria induced KC production in the explant cultures. Addition of antibiotics into the cecal cultures mitigated the effect of both bacteria and their spent supernatants on KC responses.

It should be understood from the foregoing that, while particular implementations have been illustrated and described, various modifications may be made thereto and are contemplated herein. It is also not intended that the invention be limited by the specific examples provided within the specification. While the invention has been described with reference to the aforementioned specification, the descriptions and illustrations of the preferable embodiments herein are not meant to be construed in a limiting sense. Furthermore, it shall be understood that all aspects of the invention are not limited to the specific depictions, configurations or relative proportions set forth herein which depend upon a variety of conditions and variables. Various modifications in form and detail of the embodiments of the invention will be apparent to a person skilled in the art. It is therefore contemplated that the invention shall also cover any such modifications, variations and equivalents. It is intended that the following claims define the scope of the invention and that methods and structures within the scope of these claims and their equivalents be covered thereby.

What is claimed is:

1. A method for determining the effects of an agent on microbiota of a first subject, the method comprising:
   a) preparing a first reaction mixture that comprises a first portion of a sample from a first subject in contact with an agent and preparing a second reaction mixture that comprises a second portion of said sample, wherein said second reaction mixture does not comprise said agent,
      wherein said agent is an antibiotic,
      wherein said sample is from the gut of the first subject and/or comprises fecal or cecal material from the first subject,
      wherein said sample comprises microbiota of the first subject, and
      wherein the volumes of said first and second reaction mixtures are at most 1 milliliter (mL);
   b) obtaining an enumeration of the abundance of one or more microbial taxa in said first and second reaction mixtures, wherein said enumeration of the abundance comprises amplifying and sequencing DNA comprising the variable region of the 16S rRNA gene from said first and second reaction mixtures;
   c) determining the effects of the agent on the microbiota of the first subject, based on a comparison of the enumeration of the abundance of said one or more microbial taxa in said first and second reaction mixtures;
   d) performing a functionality assay on said first and second reaction mixtures, wherein said functionality assay comprises a cell viability assay, a barrier function assay, or a cytokine assay;
   e) determining the effects of the agent on the microbiota of the first subject, based on a comparison of the results of the functionality assays on the first and second reaction mixtures; and
   f) selecting said first subject and/or additional subjects for use of said agent in a method of treatment for a *Clostridium difficile* infection.

2. The method of claim 1, further comprising using said agent to treat said *Clostridium difficile* infection in said first subject and/or said additional subjects.

3. The method of claim 1, wherein said first subject is of a different species than said additional subjects.

4. The method of claim 1, wherein said first subject and said additional subjects are human.

5. A method for determining the effects of an agent on microbiota of a subject, comprising:
   a) preparing a first reaction mixture that comprises a first portion of a sample from a first subject in contact with an agent and a second reaction mixture that comprises a second portion of said sample and does not comprise said agent,
      wherein said agent is an antibiotic,
      wherein said sample is from the gut of the first subject and/or comprises fecal or cecal material from the first subject, and
      wherein said sample comprises microbiota of the first subject;
   b) obtaining an enumeration of the abundance of at least 60 microbial taxa in said first and second reaction mixtures, wherein said enumeration of the abundance comprises amplifying and sequencing DNA comprising the variable region of the 16S rRNA gene from said first and second reaction mixtures;
   c) determining the effects of the agent on the microbiota of the first subject, based on a comparison of the enumeration of the abundance of said at least 60 microbial taxa in said first and second reaction mixtures; and d) selecting said first subject and/or additional subjects for use of said agent in a method of treatment for a *Clostridium difficile* infection.

6. A method for determining the effects of an agent on microbiota of a subject, comprising:
   a) preparing a first reaction mixture that comprises a first portion of a sample from a first subject in contact with an agent and a second reaction mixture that comprises a second portion of said sample and does not comprise said agent,
      wherein said agent is an antibiotic,
      wherein said sample is from the gut of the first subject and/or comprises fecal or cecal material from the first subject, and
      wherein said sample comprises microbiota of the first subject;
   b) obtaining an enumeration of the abundance of one or more microbial taxa in said first and second reaction mixtures, wherein said enumeration of the abundance comprises amplifying and sequencing DNA comprising the variable region of the 16S rRNA gene from said first and second reaction mixtures, and
      wherein the volumes of said first and second reaction mixtures are at most 1 milliliter (mL);
   c) determining the effects of the agent on the microbiota of the first subject, based on a comparison of the enumeration of the abundance of said one or more microbial taxa in said first and second reaction mixtures; and
   d) selecting said first subject and/or additional subjects for use of said antibiotic agent in a method of treatment for a *Clostridium difficile* infection.

7. A method for screening test antibiotic agents for use in treatment of a *Clostridium difficile* infection, the method comprising:
   a) preparing at least ten individual first reaction mixtures that each comprises an aliquot of a first portion of a sample from a first subject who has a *Clostridium difficile* infection, wherein said first portion in each individual reaction mixture is in contact with a chemically distinct test antibiotic agent and preparing a second reaction mixture that comprises a second portion of said sample and does not comprise said antibiotic agents,
      wherein said sample is from the gut of the first subject and/or comprises fecal or cecal material from the first subject,
      wherein said sample comprises microbiota of the first subject, and
      wherein the volumes of said first reaction mixtures and said second reaction mixture are at most 1 milliliter (mL);
   b) obtaining an enumeration of the abundance of one or more microbial taxa in said first and second reaction mixtures, wherein said enumeration of the abundance comprises amplifying and sequencing DNA comprising the variable region of the 16S rRNA gene from each of said first individual reaction mixtures and said second reaction mixture;
   c) determining the effects of each of said test antibiotic agents on the microbiota of the first subject, based on a comparison of the enumeration of the abundance of said one or more microbial taxa in said first and second reaction mixtures;
   d) performing a functionality assay on each of said first individual reaction mixtures and said second reaction mixture, wherein said functionality assay comprises a cell viability assay, a barrier function assay, or a cytokine assay;
   e) determining the effects of the each of said test antibiotic agents on the microbiota of the first subject, based on a comparison of the results of the functionality assays on the first and second reaction mixtures; and
   f) making a decision regarding the utility of each of said at least ten antibiotic agents to be used as a drug for treatment of said infection based upon a comparison of the results of the enumeration of the abundance of said one or more microbial taxa and the functionality assays on the microbiota in the first and second reaction mixtures.

8. A method for determining the suitability of an agent to be used as ft an antibiotic, the method comprising:
   a) preparing a first reaction mixture that comprises a first sample from a first subject who has a *Clostridium difficile* infection, wherein said first sample is in contact with an agent,
      wherein said first sample is from the gut of the first subject and/or comprises fecal or cecal material from the first subject,
      wherein said sample comprises microbiota of the first subject, and
      wherein the volume of said first reaction mixture is at most 1 milliliter (mL);
   b) obtaining an enumeration of the abundance of one or more microbial taxa in said first reaction mixture, wherein said enumeration of the abundance comprises amplifying and sequencing DNA comprising the variable region of the 16S rRNA gene from said first reaction mixture;
   c) determining the effects of the agent on the microbiota of the first subject, based on a comparison of the enumeration of the abundance of said one or more microbial taxa in said first reaction mixture;
   d) performing a functionality assay on said first reaction mixture, wherein said functionality assay comprises a cell viability assay, a barrier function assay, or a cytokine assay;
   e) preparing a second reaction mixture that comprises a second sample from a second subject who does not have said infection, wherein said second sample is in contact with said agent,
      wherein said second sample is from the gut of the second subject and/or comprises fecal or cecal material from the second subject
      wherein said sample comprises microbiota of the second subject, and
      wherein the volume of said second reaction mixture is at most 1 milliliter (mL);
   f) obtaining an enumeration of the abundance of one or more microbial taxa in said second reaction mixture, wherein said enumeration of the abundance comprises amplifying and sequencing DNA comprising the variable region of the 16S rRNA gene from said second reaction mixture;
   g) determining the effects of the agent on the microbiota of the first subject, based on a comparison of the enumeration of the abundance of said one or more microbial taxa in said second reaction mixture;
   h) performing a functionality assay on said second reaction mixture, wherein said functionality assay comprises a cell viability assay, a barrier function assay, or a cytokine assay; and i) making a decision regarding the suitability of said agent to be used as a therapeutic antibiotic drug for treatment of said infection based upon a comparison of the results of the enumeration of the abundance of said one or more microbial taxa and the functionality assays on the microbiota of the first and second subjects in the first and second reaction mixtures, respectively.

9. The method as in claim 5, wherein said microbial taxa are operational taxonomic units (OTUs).

10. The method as in claim 1, wherein said sample is processed into a slurry.

11. The method as in claim 1, wherein said reaction mixture is incubated in an anaerobic atmosphere.

12. The method of claim 1, wherein said functionality assay comprises contacting and incubating said first and second reaction mixtures with HT29, HT29 MTX, or CaCo2 cells, or mouse colon organotypic colon cells.

13. The method of claim 1, wherein said barrier function assay comprises incubating said first and second reaction mixtures with a labeled Dextran.

14. The method of claim 1, wherein said cytokine assay comprises detection of IL-8 production.

15. The method of claim 1, wherein said cell viability assay comprises incorporation and quantification of a fluorescently labeled compound.

16. The method of claim 8, further comprising using said agent to treat said *Clostridium difficile* infection in said first subject and/or said additional subjects.

17. The method of claim 5, further comprising, prior to step (d):
   i) performing a functionality assay on said first and second reaction mixtures, wherein said functionality assay comprises a cell viability assay, a barrier function assay, or a cytokine assay; and
   ii) determining the effects of the agent on the microbiota of the first subject, based on a comparison of the results of the functionality assays on the first and second reaction mixtures.

18. The method as in claim 1, wherein said microbial taxa are operational taxonomic units (OTUs).

19. The method as in claim 6, wherein said microbial taxa are operational taxonomic units (OTUs).

20. The method as in claim 7, wherein said microbial taxa are operational taxonomic units (OTUs).

21. The method as in claim 8, wherein said microbial taxa are operational taxonomic units (OTUs).

* * * * *